(12) United States Patent
Smith et al.

(10) Patent No.: US 10,925,639 B2
(45) Date of Patent: Feb. 23, 2021

(54) IMPLANT PLACEMENT AND REMOVAL SYSTEMS

(71) Applicant: Intarcia Therapeutics, Inc., Boston, MA (US)

(72) Inventors: Jay S. Smith, Wellesley Hills, MA (US); Michael R. Cole, Stratham, NH (US); James M. Sellers, Eliot, ME (US); Scott D. Lautenbach, San Mateo, CA (US); Amy K. Whitson, Columbus, OH (US); Matthew Weber, Berkley, MA (US)

(73) Assignee: Intarcia Therapeutics, Inc., Boston, MA (US)

( * ) Notice: Subject to any disclaimer, the term of this patent is extended or adjusted under 35 U.S.C. 154(b) by 131 days.

(21) Appl. No.: 15/172,132

(22) Filed: Jun. 2, 2016

(65) Prior Publication Data

US 2016/0354115 A1     Dec. 8, 2016

Related U.S. Application Data

(60) Provisional application No. 62/170,561, filed on Jun. 3, 2015, provisional application No. 62/170,994, filed on Jun. 4, 2015.

(51) Int. Cl.
*A61B 17/34*     (2006.01)
*A61M 37/00*     (2006.01)
(Continued)

(52) U.S. Cl.
CPC ...... *A61B 17/3468* (2013.01); *A61B 17/3403* (2013.01); *A61B 17/3494* (2013.01); *A61B 17/50* (2013.01); *A61B 17/28* (2013.01); *A61B 17/282* (2013.01); *A61B 17/2833* (2013.01); *A61B 2017/2808* (2013.01); *A61B 2017/2837* (2013.01); *A61B 2017/2845* (2013.01);
(Continued)

(58) Field of Classification Search
CPC .......... A61B 17/3468; A61B 17/00491; A61B 17/3403; A61B 2017/3407; A61M 5/425; A61M 19/00; A61M 37/0069
See application file for complete search history.

(56) References Cited

U.S. PATENT DOCUMENTS 2,110,208 A     3/1938    Eggert
2,168,437 A     8/1939    Buercklin
(Continued)

FOREIGN PATENT DOCUMENTS

EP     0079405     5/1983
EP     0254394     1/1988
(Continued)

OTHER PUBLICATIONS

Gonzalez, et al., "Hemoglobin A1c: A Reliable and Accurate Test for Diabetes Care? A Prospective Study in Mexico," Salud Publica Mex 55:462-468 (2013).
(Continued)

*Primary Examiner* — Kami A Bosworth
*Assistant Examiner* — Tezita Z Watts
(74) *Attorney, Agent, or Firm* — Lathrop GPM LLP; Brian C. Trinque, Esq.

(57) ABSTRACT

Devices, methods, and systems are provided for placing an implant into a patient and removing it therefrom.

26 Claims, 16 Drawing Sheets

(51) Int. Cl.
*A61B 17/50* (2006.01)
*A61M 19/00* (2006.01)
*A61M 5/42* (2006.01)
*A61B 17/28* (2006.01)
*A61B 90/00* (2016.01)

(52) U.S. Cl.
CPC .......... *A61B 2017/3407* (2013.01); *A61B 2090/0811* (2016.02); *A61M 5/425* (2013.01); *A61M 19/00* (2013.01); *A61M 37/0069* (2013.01)

(56) References Cited

U.S. PATENT DOCUMENTS

| | | |
|---|---|---|
| 2,531,724 A | 11/1950 | Cevasco |
| D179,537 S | 1/1957 | Floyd et al. |
| 3,025,991 A | 3/1962 | Gillon |
| 3,122,162 A | 2/1964 | Sands |
| 3,523,906 A | 8/1970 | Vracken et al. |
| 3,625,214 A | 12/1971 | Higuchi |
| 3,632,768 A | 1/1972 | Bergy et al. |
| 3,691,090 A | 9/1972 | Kitajima et al. |
| D226,915 S | 5/1973 | Huggins |
| 3,732,865 A | 5/1973 | Higuchi et al. |
| 3,737,337 A | 6/1973 | Schnoring et al. |
| 3,773,919 A | 11/1973 | Boswell et al. |
| 3,797,492 A | 3/1974 | Place |
| 3,869,549 A | 3/1975 | Geller |
| 3,891,570 A | 6/1975 | Fukushima et al. |
| D236,035 S | 7/1975 | Ciencewicki |
| 3,960,757 A | 6/1976 | Morishita et al. |
| 3,987,790 A | 10/1976 | Eckenhoff et al. |
| 3,995,631 A | 12/1976 | Higuchi et al. |
| 3,995,632 A | 12/1976 | Nakano et al. |
| 4,008,719 A | 2/1977 | Theeuwes et al. |
| 4,034,756 A | 7/1977 | Higuchi et al. |
| 4,078,060 A | 3/1978 | Benson et al. |
| 4,111,201 A | 9/1978 | Theeuwes |
| 4,111,202 A | 9/1978 | Theeuwes |
| 4,111,203 A | 9/1978 | Theeuwes |
| 4,203,439 A | 5/1980 | Theeuwes |
| 4,211,771 A | 7/1980 | Witkowski et al. |
| 4,221,862 A | 9/1980 | Naito et al. |
| 4,243,030 A | 1/1981 | Lynch et al. |
| D258,837 S | 4/1981 | Spranger et al. |
| D259,458 S | 6/1981 | Fuller et al. |
| 4,305,927 A | 12/1981 | Theeuwes et al. |
| 4,310,516 A | 1/1982 | Chang et al. |
| 4,340,054 A | 7/1982 | Michaels |
| 4,350,271 A | 9/1982 | Eckenhoff |
| 4,373,527 A | 2/1983 | Fischell |
| 4,376,118 A | 3/1983 | Daher |
| 4,384,975 A | 5/1983 | Fong |
| 4,389,330 A | 6/1983 | Tice et al. |
| 4,439,196 A | 3/1984 | Higuchi |
| 4,444,498 A | 4/1984 | Heinemann |
| 4,455,143 A | 6/1984 | Theeuwes et al. |
| 4,455,145 A | 6/1984 | Theeuwes |
| 4,530,840 A | 7/1985 | Tice et al. |
| 4,552,561 A | 11/1985 | Eckenhoff et al. |
| 4,588,614 A | 5/1986 | Lauchenauer |
| 4,594,108 A | 6/1986 | Greminger, Jr. et al. |
| 4,609,374 A | 9/1986 | Ayer |
| 4,639,244 A | 1/1987 | Rizk et al. |
| 4,655,462 A | 4/1987 | Balsells |
| 4,673,405 A | 6/1987 | Guittard et al. |
| 4,675,184 A | 6/1987 | Hasegawa et al. |
| 4,695,623 A | 9/1987 | Stabinsky |
| 4,727,138 A | 2/1988 | Goeddel et al. |
| 4,734,284 A | 3/1988 | Terada et al. |
| 4,737,437 A | 4/1988 | Gutsell, Jr. et al. |
| 4,743,449 A | 5/1988 | Yoshida et al. |
| 4,753,651 A | 6/1988 | Eckenhoff |
| 4,762,791 A | 8/1988 | Goeddel et al. |
| 4,765,989 A | 8/1988 | Wong et al. |
| 4,783,337 A | 11/1988 | Wong et al. |
| 4,818,517 A | 4/1989 | Kwee et al. |
| 4,820,638 A | 4/1989 | Swetly et al. |
| 4,826,144 A | 5/1989 | Balsells |
| 4,830,344 A | 5/1989 | Balsells |
| 4,840,896 A | 6/1989 | Reddy et al. |
| 4,845,196 A | 7/1989 | Cowling |
| 4,847,079 A | 7/1989 | Kwan |
| 4,851,228 A | 7/1989 | Zentner et al. |
| 4,865,845 A | 9/1989 | Eckenhoff et al. |
| 4,873,080 A | 10/1989 | Brickl et al. |
| 4,874,388 A | 10/1989 | Wong et al. |
| 4,876,781 A | 10/1989 | Balsells |
| 4,885,166 A | 12/1989 | Meyer et al. |
| 4,886,668 A | 12/1989 | Haslam et al. |
| 4,892,778 A | 1/1990 | Theeuwes et al. |
| 4,893,795 A | 1/1990 | Balsells |
| 4,897,471 A | 1/1990 | Stabinsky |
| 4,907,788 A | 3/1990 | Balsells |
| 4,915,366 A | 4/1990 | Balsells |
| 4,915,949 A | 4/1990 | Wong et al. |
| 4,915,954 A | 4/1990 | Ayer et al. |
| 4,917,887 A | 4/1990 | Hauptmann et al. |
| 4,917,895 A | 4/1990 | Lee et al. |
| 4,923,805 A | 5/1990 | Reddy et al. |
| 4,927,687 A | 5/1990 | Nuwayser |
| 4,929,554 A | 5/1990 | Goeddel et al. |
| 4,931,285 A | 6/1990 | Edgren et al. |
| 4,934,666 A | 6/1990 | Balsells |
| 4,940,465 A | 7/1990 | Theeuwes et al. |
| 4,940,588 A | 7/1990 | Sparks et al. |
| 4,952,402 A | 8/1990 | Sparks et al. |
| 4,957,119 A | 9/1990 | de Nijs |
| 4,961,253 A | 10/1990 | Balsells |
| 4,964,204 A | 10/1990 | Balsells |
| 4,969,884 A | 11/1990 | Yum |
| 4,974,821 A | 12/1990 | Balsells |
| 4,976,966 A | 12/1990 | Theeuwes et al. |
| 5,004,689 A | 4/1991 | Fiers et al. |
| 5,006,346 A | 4/1991 | Theeuwes et al. |
| 5,019,382 A | 5/1991 | Cummins, Jr. |
| 5,019,400 A | 5/1991 | Gombotz et al. |
| 5,023,088 A | 6/1991 | Wong et al. |
| 5,024,842 A | 6/1991 | Edgren et al. |
| 5,030,216 A | 7/1991 | Theeuwes et al. |
| 5,034,229 A | 7/1991 | Magruder et al. |
| 5,057,318 A | 10/1991 | Magruder et al. |
| 5,059,423 A | 10/1991 | Magruder et al. |
| 5,066,436 A | 11/1991 | Komen et al. |
| 5,071,642 A | 12/1991 | Lahr et al. |
| 5,072,070 A | 12/1991 | Balsells |
| 5,079,388 A | 1/1992 | Balsells |
| 5,091,188 A | 2/1992 | Haynes |
| 5,108,078 A | 4/1992 | Balsells |
| 5,110,596 A | 5/1992 | Magruder et al. |
| 5,112,614 A | 5/1992 | Magruder et al. |
| 5,113,938 A | 5/1992 | Clayton |
| 5,117,066 A | 5/1992 | Balsells |
| D326,718 S | 6/1992 | Maxwell |
| 5,118,666 A | 6/1992 | Habener |
| 5,120,306 A | 6/1992 | Gosselin |
| 5,120,712 A | 6/1992 | Habener |
| 5,120,832 A | 6/1992 | Goeddel et al. |
| 5,122,128 A | 6/1992 | Cardinal et al. |
| 5,122,377 A | 6/1992 | Miller |
| 5,126,142 A | 6/1992 | Ayer et al. |
| 5,126,147 A | 6/1992 | Silvestri et al. |
| 5,134,244 A | 7/1992 | Balsells |
| 5,137,727 A | 8/1992 | Eckenhoff |
| D329,278 S | 9/1992 | Gallup |
| 5,151,093 A | 9/1992 | Theeuwes et al. |
| 5,160,122 A | 11/1992 | Balsells |
| 5,160,743 A | 11/1992 | Edgren et al. |
| 5,161,806 A | 11/1992 | Balsells |
| 5,180,591 A | 1/1993 | Margruder et al. |
| 5,190,765 A | 3/1993 | Jao et al. |
| 5,203,849 A | 4/1993 | Balsells |
| 5,204,108 A | 4/1993 | Ilium |
| 5,207,752 A | 5/1993 | Sorensen et al. |

(56) References Cited

U.S. PATENT DOCUMENTS

| | | |
|---|---|---|
| 5,209,746 A | 5/1993 | Balaban et al. |
| 5,213,809 A | 5/1993 | Wright et al. |
| 5,213,810 A | 5/1993 | Steber |
| 5,219,572 A | 6/1993 | Sivaramakrishnan |
| 5,221,278 A | 6/1993 | Linkwitz et al. |
| 5,223,265 A | 6/1993 | Wong |
| 5,225,205 A | 7/1993 | Orsolini |
| 5,231,176 A | 7/1993 | Goeddel et al. |
| 5,234,424 A | 8/1993 | Yum et al. |
| 5,234,692 A | 8/1993 | Magruder et al. |
| 5,234,693 A | 8/1993 | Magruder et al. |
| 5,234,695 A | 8/1993 | Hobbs et al. |
| 5,252,338 A | 10/1993 | Jao et al. |
| 5,260,069 A | 11/1993 | Chen |
| D342,855 S | 1/1994 | Butler, II |
| 5,278,151 A | 1/1994 | Korb et al. |
| 5,279,608 A | 1/1994 | Cherif Cheikh |
| 5,284,655 A | 2/1994 | Bogdansky et al. |
| 5,288,501 A | 2/1994 | Nürnberg et al. |
| 5,288,502 A | 2/1994 | Mcginity et al. |
| 5,290,271 A | 3/1994 | Jernberg |
| 5,300,079 A | 4/1994 | Niezink et al. |
| 5,300,302 A | 4/1994 | Tachon et al. |
| 5,308,348 A | 5/1994 | Balaban et al. |
| 5,312,335 A | 5/1994 | McKinnon et al. |
| 5,312,389 A | 5/1994 | Theeuwes et al. |
| 5,312,390 A | 5/1994 | Wong |
| 5,318,558 A | 6/1994 | Linkwitz et al. |
| 5,318,780 A | 6/1994 | Viegas et al. |
| 5,320,616 A | 6/1994 | Magndu et al. |
| 5,324,280 A | 6/1994 | Wong et al. |
| 5,336,057 A | 8/1994 | Fukuda et al. |
| 5,336,505 A | 8/1994 | Ng et al. |
| 5,352,662 A | 10/1994 | Brooks et al. |
| 5,368,588 A | 11/1994 | Bettinger |
| 5,368,863 A | 11/1994 | Eckenhoff et al. |
| 5,371,089 A | 12/1994 | Rattan |
| 5,374,620 A | 12/1994 | Clark et al. |
| 5,385,738 A | 1/1995 | Yamahira et al. |
| 5,385,887 A | 1/1995 | Yim et al. |
| 5,407,609 A | 4/1995 | Tice et al. |
| D358,644 S | 5/1995 | Park |
| 5,411,951 A | 5/1995 | Mitchell |
| 5,413,572 A | 5/1995 | Wong et al. |
| 5,413,672 A | 5/1995 | Hirotsuji et al. |
| 5,424,286 A | 6/1995 | Eng |
| 5,428,024 A | 6/1995 | Chu et al. |
| 5,429,602 A | 7/1995 | Hauser |
| 5,439,688 A | 8/1995 | Orsolini et al. |
| 5,443,459 A | 8/1995 | Wong et al. |
| 5,445,829 A | 8/1995 | Paradissis et al. |
| 5,456,679 A | 10/1995 | Balaban et al. |
| 5,458,888 A | 10/1995 | Chen |
| 5,464,929 A | 11/1995 | Bezwada et al. |
| 5,472,708 A | 12/1995 | Chen |
| 5,478,564 A | 12/1995 | Wantier et al. |
| 5,486,365 A | 1/1996 | Takado et al. |
| 5,498,255 A | 3/1996 | Wong et al. |
| 5,511,355 A | 4/1996 | Dingier |
| 5,512,293 A | 4/1996 | Landrau et al. |
| 5,512,549 A | 4/1996 | Chen et al. |
| 5,514,110 A | 5/1996 | Teh |
| 5,529,914 A | 6/1996 | Hubbell et al. |
| 5,531,736 A | 7/1996 | Wong et al. |
| 5,540,665 A | 7/1996 | Mercado et al. |
| 5,540,912 A | 7/1996 | Roorda et al. |
| 5,541,172 A | 7/1996 | Labrie et al. |
| 5,542,682 A | 8/1996 | Goldstein et al. |
| 5,543,156 A | 8/1996 | Roorda et al. |
| 5,545,618 A | 8/1996 | Buckley et al. |
| 5,556,642 A | 9/1996 | Kobayashi |
| 5,557,318 A | 9/1996 | Gabriel |
| 5,571,525 A | 11/1996 | Roorda et al. |
| 5,574,008 A | 11/1996 | Johnson et al. |
| 5,574,137 A | 11/1996 | Gray et al. |
| 5,580,578 A | 12/1996 | Oshlack et al. |
| 5,589,167 A | 12/1996 | Cleland et al. |
| 5,595,751 A | 1/1997 | Bezwada |
| 5,595,759 A | 1/1997 | Wright et al. |
| 5,597,579 A | 1/1997 | Bezwada et al. |
| 5,602,010 A | 2/1997 | Hauptmann et al. |
| 5,605,688 A | 2/1997 | Himmler et al. |
| 5,607,687 A | 3/1997 | Bezwada et al. |
| 5,609,885 A | 3/1997 | Rivera et al. |
| 5,614,221 A | 3/1997 | Fjellstrom |
| 5,614,492 A | 3/1997 | Habener |
| 5,618,552 A | 4/1997 | Bezwada et al. |
| 5,620,698 A | 4/1997 | Bezwada et al. |
| 5,620,705 A | 4/1997 | Dong et al. |
| 5,630,796 A | 5/1997 | Bellhouse et al. |
| 5,633,011 A | 5/1997 | Dong et al. |
| 5,635,213 A | 6/1997 | Nystrom et al. |
| 5,639,477 A | 6/1997 | Maruyama et al. |
| 5,639,640 A | 6/1997 | Reddy et al. |
| 5,645,850 A | 7/1997 | Bezwada et al. |
| 5,648,088 A | 7/1997 | Bezwada et al. |
| 5,650,173 A | 7/1997 | Ramstack et al. |
| 5,654,008 A | 8/1997 | Herbert et al. |
| 5,654,010 A | 8/1997 | Johnson et al. |
| 5,656,297 A | 8/1997 | Bernstein et al. |
| 5,656,299 A | 8/1997 | Kino et al. |
| 5,658,593 A | 8/1997 | Orly et al. |
| 5,660,847 A | 8/1997 | Magruder et al. |
| 5,660,858 A | 8/1997 | Parikh et al. |
| 5,660,861 A | 8/1997 | Jao et al. |
| 5,667,808 A | 9/1997 | Johnson et al. |
| 5,668,170 A | 9/1997 | Gyory |
| 5,672,549 A | 9/1997 | Minami et al. |
| 5,676,942 A | 10/1997 | Testa et al. |
| 5,686,097 A | 11/1997 | Taskovich et al. |
| 5,688,801 A | 11/1997 | Mesens |
| 5,690,925 A | 11/1997 | Gray et al. |
| 5,690,952 A | 11/1997 | Magruder et al. |
| 5,697,113 A | 12/1997 | Shatz et al. |
| 5,698,213 A | 12/1997 | Jamiolkowski et al. |
| 5,700,486 A | 12/1997 | Canal et al. |
| 5,700,583 A | 12/1997 | Jamiolkowski et al. |
| 5,703,200 A | 12/1997 | Bezwada et al. |
| 5,707,644 A | 1/1998 | Ilium |
| 5,711,967 A | 1/1998 | Juch |
| 5,713,847 A | 2/1998 | Howard, III et al. |
| 5,718,922 A | 2/1998 | Herrero-Vanrell |
| 5,728,088 A | 3/1998 | Margruder et al. |
| 5,728,396 A | 3/1998 | Peery et al. |
| 5,733,572 A | 3/1998 | Unger et al. |
| 5,736,159 A | 4/1998 | Chen et al. |
| 5,738,845 A | 4/1998 | Imakawa |
| 5,747,058 A | 5/1998 | Tipton et al. |
| 5,756,450 A | 5/1998 | Lorenz et al. |
| 5,767,251 A | 6/1998 | Reddy et al. |
| 5,770,231 A | 6/1998 | Mesens et al. |
| 5,782,396 A | 7/1998 | Mastri et al. |
| 5,792,477 A | 8/1998 | Rickey et al. |
| 5,795,591 A | 8/1998 | Lee et al. |
| 5,795,779 A | 8/1998 | McCormick et al. |
| 5,807,876 A | 9/1998 | Armistead et al. |
| 5,814,323 A | 9/1998 | Lyle |
| D399,821 S | 10/1998 | Tyneski et al. |
| 5,817,129 A | 10/1998 | Labrecque et al. |
| 5,830,501 A | 11/1998 | Dong et al. |
| 5,836,935 A | 11/1998 | Ashton et al. |
| 5,843,891 A | 12/1998 | Sherman |
| 5,844,017 A | 12/1998 | Jamiolkowski et al. |
| 5,851,451 A | 12/1998 | Takechi et al. |
| 5,858,746 A | 1/1999 | Hubbell et al. |
| 5,859,150 A | 1/1999 | Jamiolkowski et al. |
| 5,861,166 A | 1/1999 | Eckenhoff |
| 5,871,770 A | 2/1999 | Margruder et al. |
| 5,871,778 A | 2/1999 | Kino et al. |
| 5,874,388 A | 2/1999 | Hsu |
| 5,876,746 A | 3/1999 | Jona et al. |
| 5,882,676 A | 3/1999 | Lee et al. |
| D408,917 S | 4/1999 | Hacker |
| 5,904,935 A | 5/1999 | Eckenhoff et al. |

(56) References Cited

U.S. PATENT DOCUMENTS

| | | |
|---|---|---|
| 5,906,816 A | 5/1999 | Soos et al. |
| 5,906,830 A | 5/1999 | Farinas et al. |
| 5,908,621 A | 6/1999 | Glue et al. |
| 5,916,598 A | 6/1999 | Rickey et al. |
| 5,922,253 A | 7/1999 | Herbert et al. |
| 5,928,666 A | 7/1999 | Farinas et al. |
| 5,932,547 A | 8/1999 | Stevenson et al. |
| 5,938,654 A | 8/1999 | Wong et al. |
| 5,939,286 A | 8/1999 | Johnson et al. |
| 5,942,223 A | 8/1999 | Bazer et al. |
| 5,942,253 A | 8/1999 | Gombotz et al. |
| 5,945,126 A | 8/1999 | Thanoo et al. |
| 5,948,430 A | 9/1999 | Zerbe et al. |
| 5,951,521 A | 9/1999 | Mastrototaro et al. |
| 5,958,909 A | 9/1999 | Habener |
| D415,073 S | 10/1999 | Meehan et al. |
| 5,962,023 A | 10/1999 | Jamiolkowski et al. |
| 5,965,168 A | 10/1999 | Mesens et al. |
| 5,972,370 A | 10/1999 | Eckenhoff et al. |
| 5,972,373 A | 10/1999 | Yajima et al. |
| 5,976,109 A | 11/1999 | Heruth |
| 5,980,945 A | 11/1999 | Ruiz |
| 5,981,719 A | 11/1999 | Wolszwillo et al. |
| 5,984,890 A | 11/1999 | Gast et al. |
| 5,985,305 A | 11/1999 | Peery et al. |
| 5,989,463 A | 11/1999 | Tracy et al. |
| 5,997,527 A | 12/1999 | Gumucio et al. |
| 5,997,902 A | 12/1999 | Maruyama et al. |
| 6,007,805 A | 12/1999 | Foster et al. |
| 6,017,545 A | 1/2000 | Modi |
| 6,022,561 A | 2/2000 | Carlsson et al. |
| 6,023,802 A | 2/2000 | King |
| 6,029,361 A | 2/2000 | Newman |
| 6,056,718 A | 5/2000 | Funderburk et al. |
| 6,060,450 A | 5/2000 | Soos et al. |
| 6,069,133 A | 5/2000 | Carlo et al. |
| 6,074,377 A | 6/2000 | Sanfilippo, II |
| 6,074,660 A | 6/2000 | Jamiolkowski et al. |
| 6,074,673 A | 6/2000 | Guillen |
| 6,100,346 A | 8/2000 | Jamiolkowski et al. |
| 6,110,503 A | 8/2000 | Rickey et al. |
| D430,671 S | 9/2000 | Shute |
| 6,113,938 A | 9/2000 | Chen et al. |
| 6,113,947 A | 9/2000 | Cleland et al. |
| 6,120,787 A | 9/2000 | Gustafsson et al. |
| 6,124,261 A | 9/2000 | Stevenson et al. |
| 6,124,281 A | 9/2000 | Lewis et al. |
| 6,127,520 A | 10/2000 | Ueda et al. |
| 6,129,761 A | 10/2000 | Hubbell |
| 6,130,200 A | 10/2000 | Brodbeck et al. |
| 6,132,420 A | 10/2000 | Dionne et al. |
| 6,133,249 A | 10/2000 | Hills |
| 6,133,429 A | 10/2000 | Davis et al. |
| 6,147,168 A | 11/2000 | Jamiolkowski et al. |
| 6,156,331 A | 12/2000 | Peery et al. |
| 6,172,046 B1 | 1/2001 | Albrecht |
| 6,174,547 B1 | 1/2001 | Dong et al. |
| 6,177,096 B1 | 1/2001 | Zerbe et al. |
| 6,183,461 B1 | 2/2001 | Matsuura et al. |
| 6,187,095 B1 | 2/2001 | Labrecque et al. |
| 6,190,350 B1 | 2/2001 | Davis et al. |
| 6,190,700 B1 | 2/2001 | Okada et al. |
| 6,190,702 B1 | 2/2001 | Takada et al. |
| 6,191,102 B1 | 2/2001 | DiMarchi et al. |
| 6,204,022 B1 | 3/2001 | Johnson et al. |
| 6,217,893 B1 | 4/2001 | Pellet et al. |
| 6,217,906 B1 | 4/2001 | Gumucio et al. |
| 6,217,908 B1 | 4/2001 | Mathiowitz et al. |
| 6,218,431 B1 | 4/2001 | Schoen et al. |
| 6,224,894 B1 | 5/2001 | Jamiolkowski et al. |
| 6,235,712 B1 | 5/2001 | Stevenson et al. |
| 6,245,349 B1 | 6/2001 | Yiv et al. |
| 6,245,357 B1 | 6/2001 | Edgren et al. |
| 6,248,112 B1 | 6/2001 | Gambale et al. |
| 6,251,435 B1 | 6/2001 | Jamiolkowski et al. |
| D445,975 S | 7/2001 | Stratford |
| 6,258,377 B1 | 7/2001 | New et al. |
| 6,261,584 B1 | 7/2001 | Peery et al. |
| 6,268,343 B1 | 7/2001 | Knudsen et al. |
| 6,270,700 B1 | 8/2001 | Ignatious |
| 6,270,787 B1 | 8/2001 | Ayer |
| 6,277,413 B1 | 8/2001 | Sankaram |
| 6,283,949 B1 | 9/2001 | Roorda |
| 6,284,264 B1 | 9/2001 | Zerbe et al. |
| 6,284,727 B1 | 9/2001 | Kim et al. |
| 6,287,295 B1 | 9/2001 | Chen et al. |
| 6,284,725 B1 | 12/2001 | Coolidge et al. |
| 6,329,336 B1 | 12/2001 | Bridon et al. |
| 6,331,311 B1 | 12/2001 | Brodbeck et al. |
| 6,372,218 B1 | 4/2002 | Cummins, Jr. |
| 6,372,256 B2 | 4/2002 | Jamiolkowski et al. |
| 6,375,978 B1 | 4/2002 | Kleiner et al. |
| 6,395,292 B2 | 5/2002 | Peery et al. |
| 6,403,655 B1 | 6/2002 | Bezwada et al. |
| 6,419,952 B2 | 7/2002 | Wong et al. |
| 6,433,144 B1 | 8/2002 | Morris et al. |
| 6,436,091 B1 | 8/2002 | Harper et al. |
| 6,447,522 B2 | 9/2002 | Gambale et al. |
| 6,451,974 B1 | 9/2002 | Hansen |
| 6,458,385 B2 | 10/2002 | Jamiolkowski et al. |
| 6,458,387 B1 | 10/2002 | Scott et al. |
| 6,458,924 B2 | 10/2002 | Knudsen et al. |
| 6,461,605 B1 | 10/2002 | Cutler et al. |
| 6,464,688 B1 | 10/2002 | Harper et al. |
| 6,468,961 B1 | 10/2002 | Brodbeck et al. |
| 6,471,688 B1 | 10/2002 | Harper et al. |
| 6,472,512 B1 | 10/2002 | LaFleur et al. |
| 6,485,706 B1 | 11/2002 | McCoy et al. |
| 6,495,164 B1 | 12/2002 | Ramstack et al. |
| 6,506,724 B1 | 1/2003 | Hiles et al. |
| 6,508,808 B1 | 1/2003 | Carr et al. |
| 6,514,500 B1 | 2/2003 | Bridon et al. |
| 6,514,517 B2 | 2/2003 | Jamiolkowski et al. |
| 6,524,305 B1 | 2/2003 | Peterson et al. |
| 6,528,093 B1 | 3/2003 | Kamei et al. |
| 6,528,486 B1 | 3/2003 | Larsen et al. |
| D472,896 S | 4/2003 | Peiker |
| 6,541,021 B1 | 4/2003 | Johnson et al. |
| 6,544,252 B1 | 4/2003 | Theeuwes et al. |
| 6,547,250 B1 | 4/2003 | Noble |
| 6,551,613 B1 | 4/2003 | Dong et al. |
| 6,569,420 B2 | 5/2003 | Chen et al. |
| 6,572,890 B2 | 6/2003 | Faour et al. |
| 6,579,851 B2 | 6/2003 | Goeke et al. |
| 6,592,887 B2 | 7/2003 | Zerbe et al. |
| 6,593,295 B2 | 7/2003 | Bridon et al. |
| 6,635,268 B2 | 10/2003 | Peery et al. |
| 6,645,192 B2 | 11/2003 | Kenison et al. |
| 6,667,061 B2 | 12/2003 | Ramstack et al. |
| 6,670,368 B1 | 12/2003 | Breault et al. |
| 6,673,767 B1 | 1/2004 | Brodbeck et al. |
| 6,682,522 B2 | 1/2004 | Carr et al. |
| 6,703,225 B1 | 3/2004 | Kojima et al. |
| 6,703,359 B1 | 3/2004 | Young et al. |
| 6,706,689 B2 | 3/2004 | Coolidge et al. |
| 6,709,671 B2 | 3/2004 | Zerbe et al. |
| 6,720,407 B1 | 4/2004 | Hughes et al. |
| 6,730,328 B2 | 5/2004 | Maskiwicz et al. |
| 6,741,688 B1 * | 5/2004 | Yau ............ H04M 3/4228 379/142.01 |
| 6,752,753 B1 * | 6/2004 | Hoskins ............ A61M 37/0069 600/7 |
| 6,767,887 B1 | 7/2004 | Hoffmann et al. |
| 6,821,949 B2 | 11/2004 | Bridon et al. |
| 6,833,256 B1 | 12/2004 | Pontzer et al. |
| 6,835,194 B2 | 12/2004 | Johnson et al. |
| 6,840,931 B1 | 1/2005 | Peterson et al. |
| 6,849,708 B1 | 2/2005 | Habener |
| 6,849,714 B1 | 2/2005 | Bridon et al. |
| 6,858,576 B1 | 2/2005 | Young et al. |
| 6,872,700 B1 | 3/2005 | Young et al. |
| 6,875,748 B2 | 4/2005 | Manthorpe et al. |
| 6,887,470 B1 | 5/2005 | Bridon et al. |
| 6,887,849 B2 | 5/2005 | Bridon et al. |

(56) References Cited

U.S. PATENT DOCUMENTS

| | | |
|---|---|---|
| 6,899,887 B2 | 5/2005 | Ayer |
| 6,899,898 B2 | 5/2005 | Albayrak |
| 6,902,744 B1 | 6/2005 | Kolterman et al. |
| 6,903,186 B1 | 6/2005 | Dong |
| 6,913,767 B1 | 7/2005 | Cleland et al. |
| 6,923,800 B2 | 8/2005 | Chen et al. |
| 6,924,264 B1 | 8/2005 | Prickett et al. |
| 6,939,556 B2 | 9/2005 | Lautenbach |
| 6,956,026 B2 | 10/2005 | Beeley et al. |
| 6,969,702 B2 | 11/2005 | Bertilsson et al. |
| 6,976,981 B2 | 12/2005 | Ayer |
| 6,989,366 B2 | 1/2006 | Beeley et al. |
| 6,992,065 B2 | 1/2006 | Okumu |
| 6,997,922 B2 | 2/2006 | Theeuwes et al. |
| 7,014,636 B2 | 3/2006 | Gilbert |
| 7,022,674 B2 | 4/2006 | DeFelippis et al. |
| 7,041,646 B2 | 5/2006 | Pan et al. |
| 7,074,423 B2 | 7/2006 | Fereira et al. |
| 7,084,243 B2 | 8/2006 | Glaesner et al. |
| 7,090,681 B2 * | 8/2006 | Weber .................... A61F 2/167 606/107 |
| 7,101,567 B1 | 9/2006 | Sano et al. |
| 7,101,843 B2 | 9/2006 | Glaesner et al. |
| 7,112,335 B2 | 9/2006 | Lautenbach |
| 7,115,569 B2 | 10/2006 | Beeley et al. |
| 7,138,375 B2 | 11/2006 | Beeley et al. |
| 7,138,486 B2 | 11/2006 | Habener et al. |
| 7,141,547 B2 | 11/2006 | Rosen et al. |
| 7,144,863 B2 | 12/2006 | DeFelippis et al. |
| 7,153,825 B2 | 12/2006 | Young et al. |
| 7,157,555 B1 | 1/2007 | Beeley et al. |
| 7,163,688 B2 | 1/2007 | Peery et al. |
| 7,163,697 B2 | 1/2007 | Hanes et al. |
| 7,199,217 B2 | 4/2007 | DiMarchi et al. |
| 7,205,409 B2 | 4/2007 | Pei et al. |
| 7,207,982 B2 | 4/2007 | Dionne et al. |
| 7,241,457 B2 | 7/2007 | Chen et al. |
| 7,258,869 B1 | 8/2007 | Berry et al. |
| D555,589 S | 11/2007 | Hussaini et al. |
| 7,297,761 B2 | 11/2007 | Beeley et al. |
| 7,316,680 B2 | 1/2008 | Gilbert |
| 7,393,827 B2 | 7/2008 | Nadler |
| 7,407,499 B2 | 8/2008 | Trautman |
| 7,442,682 B2 | 10/2008 | Kitaura et al. |
| 7,456,254 B2 | 11/2008 | Wright et al. |
| 7,459,432 B2 | 12/2008 | Cowley et al. |
| 7,521,423 B2 | 4/2009 | Young et al. |
| 7,563,871 B2 | 7/2009 | Wright et al. |
| 7,589,169 B2 | 9/2009 | Bolotin |
| 7,612,176 B2 | 11/2009 | Wright et al. |
| 7,635,463 B2 | 12/2009 | Bolotin et al. |
| D608,447 S | 1/2010 | Meyer et al. |
| 7,655,254 B2 | 2/2010 | Dennis et al. |
| 7,655,257 B2 | 2/2010 | Peery et al. |
| 7,666,835 B2 | 2/2010 | Bloom et al. |
| 7,682,356 B2 | 3/2010 | Alessi et al. |
| 7,727,519 B2 | 6/2010 | Moran |
| 7,731,947 B2 | 6/2010 | Eliaz et al. |
| 7,736,665 B2 | 6/2010 | Patel et al. |
| 7,741,269 B2 | 6/2010 | Young et al. |
| 7,790,140 B2 | 9/2010 | Bolotin |
| 7,825,091 B2 | 11/2010 | Bloom et al. |
| 7,829,109 B2 | 11/2010 | Chen et al. |
| 7,833,543 B2 | 11/2010 | Gilson et al. |
| 7,879,028 B2 | 2/2011 | Alessi et al. |
| 7,914,512 B2 | 3/2011 | Orth et al. |
| 7,879,794 B2 | 4/2011 | Berry et al. |
| 7,919,109 B2 | 4/2011 | Berry et al. |
| D638,478 S | 5/2011 | Block |
| 7,928,065 B2 | 6/2011 | Rohloff et al. |
| 7,964,183 B2 | 6/2011 | Eliaz et al. |
| 8,029,458 B2 | 10/2011 | Cherif-Cheikh et al. |
| 8,039,432 B2 | 10/2011 | Bridon et al. |
| 7,959,938 B2 | 11/2011 | Lautenbach et al. |
| 8,048,438 B2 | 11/2011 | Berry et al. |
| 8,052,996 B2 | 11/2011 | Lautenbach et al. |
| 8,058,233 B2 | 11/2011 | Cowley et al. |
| 8,101,576 B2 | 1/2012 | Bloom |
| 8,114,430 B2 | 2/2012 | Rohloff et al. |
| 8,114,437 B2 | 2/2012 | Rohloff et al. |
| 8,158,150 B2 | 4/2012 | Lautenbach et al. |
| 8,173,150 B2 | 5/2012 | Berry et al. |
| 8,202,836 B2 | 6/2012 | Rohloff et al. |
| 8,206,745 B2 | 6/2012 | Rohloff et al. |
| 8,211,467 B2 | 7/2012 | Rohloff et al. |
| 8,217,001 B2 | 7/2012 | Cowley et al. |
| 8,231,859 B2 | 7/2012 | Bolotin et al. |
| 8,251,946 B2 | 8/2012 | Bardy |
| 8,257,682 B2 | 9/2012 | Bolotin et al. |
| 8,257,691 B2 | 9/2012 | Eliaz et al. |
| 8,262,667 B1 | 9/2012 | Silver et al. |
| 8,263,545 B2 | 9/2012 | Bloom |
| 8,263,736 B2 | 9/2012 | Berry |
| 8,268,341 B2 | 9/2012 | Berry |
| 8,273,365 B2 | 9/2012 | Lautenbach et al. |
| 8,273,713 B2 | 9/2012 | Pittner et al. |
| D669,589 S | 10/2012 | Delaey |
| 8,277,776 B2 | 10/2012 | Bolotin et al. |
| 8,278,267 B2 | 10/2012 | Weyer et al. |
| 8,288,338 B2 | 10/2012 | Alessi et al. |
| 8,298,561 B2 | 10/2012 | Alessi et al. |
| 8,299,025 B2 | 10/2012 | Alessi et al. |
| 8,343,140 B2 | 1/2013 | Alessi et al. |
| 8,367,095 B2 | 2/2013 | Lautenbach et al. |
| 8,372,424 B2 | 2/2013 | Berry et al. |
| D678,889 S | 3/2013 | Chiu |
| 8,398,967 B2 | 3/2013 | Eliaz et al. |
| 8,440,226 B2 | 5/2013 | Rohloff et al. |
| 8,454,552 B2 | 6/2013 | Bardy |
| 8,460,694 B2 | 6/2013 | Rohloff et al. |
| 8,470,353 B2 | 6/2013 | Lautenbach et al. |
| 8,747,412 B2 | 6/2014 | Bae et al. |
| 8,801,700 B2 | 8/2014 | Alessi et al. |
| 8,815,802 B2 | 8/2014 | Kalthoff et al. |
| 8,858,621 B2 | 10/2014 | Oba et al. |
| 8,865,202 B2 | 10/2014 | Zerbe et al. |
| 8,888,745 B2 | 11/2014 | Van Der Graaf et al. |
| 8,926,595 B2 | 1/2015 | Alessi et al. |
| 8,940,316 B2 | 1/2015 | Alessi et al. |
| 8,992,961 B2 | 3/2015 | Lautenbach et al. |
| 8,992,962 B2 | 3/2015 | Lautenbach et al. |
| 9,044,209 B2 | 6/2015 | Dayton et al. |
| 9,078,900 B2 | 7/2015 | Kuzma et al. |
| 9,095,553 B2 | 8/2015 | Rohloff et al. |
| 9,241,722 B2 | 1/2016 | Yu |
| D750,764 S | 3/2016 | Desocio |
| 9,332,995 B2 | 5/2016 | Russo |
| 9,526,763 B2 | 12/2016 | Rohloff et al. |
| 9,539,200 B2 | 1/2017 | Lautenbach |
| 9,572,889 B2 | 2/2017 | Alessi et al. |
| D789,539 S | 6/2017 | Kleiner et al. |
| D789,540 S | 6/2017 | Gyorgy |
| 9,682,127 B2 | 6/2017 | Alessi et al. |
| RE46,577 E | 10/2017 | Collins et al. |
| 9,889,085 B1 | 2/2018 | Alessi et al. |
| 10,314,617 B2 | 6/2019 | Bratlie |
| 2001/0012511 A1 | 8/2001 | Bezwada et al. |
| 2001/0021377 A1 | 9/2001 | Jamiolkowski et al. |
| 2001/0021822 A1 | 9/2001 | Ayer |
| 2001/0022974 A1 | 9/2001 | Ayer |
| 2001/0026793 A1 | 10/2001 | Jamiolkowski et al. |
| 2001/0027311 A1 | 10/2001 | Chen et al. |
| 2001/0036472 A1 | 11/2001 | Wong et al. |
| 2001/0037190 A1 | 11/2001 | Beisswenger |
| 2001/0040326 A1 | 11/2001 | Balczun |
| 2002/0001631 A1 | 1/2002 | Okumu |
| 2002/0004481 A1 | 1/2002 | Cleland et al. |
| 2002/0012818 A1 | 1/2002 | Ruppi et al. |
| 2002/0034532 A1 | 3/2002 | Brodbeck et al. |
| 2002/0037309 A1 | 3/2002 | Jamiolkowski et al. |
| 2002/0048600 A1 | 4/2002 | Bhatt et al. |
| 2002/0098180 A1 | 7/2002 | Lei |
| 2002/0136848 A1 | 9/2002 | Yoshii et al. |
| 2002/0137666 A1 | 9/2002 | Beeley et al. |

(56) References Cited

U.S. PATENT DOCUMENTS

| | | |
|---|---|---|
| 2002/0141985 A1 | 10/2002 | Pittner et al. |
| 2002/0197185 A1 | 12/2002 | Jamiolkowski et al. |
| 2002/0197235 A1 | 12/2002 | Moran |
| 2003/0032947 A1 | 2/2003 | Harper et al. |
| 2003/0044467 A1 | 3/2003 | Brodbeck et al. |
| 2003/0045454 A1 | 3/2003 | Okumu et al. |
| 2003/0059376 A1 | 3/2003 | Libbey et al. |
| 2003/0060425 A1 | 3/2003 | Ahlem et al. |
| 2003/0078618 A1 | 4/2003 | Fey et al. |
| 2003/0097121 A1 | 6/2003 | Babcock et al. |
| 2003/0104063 A1 | 6/2003 | Babcock et al. |
| 2003/0108608 A1 | 6/2003 | Berry et al. |
| 2003/0108609 A1 | 6/2003 | Berry et al. |
| 2003/0113380 A1 | 6/2003 | Ramstack et al. |
| 2003/0118660 A1 | 6/2003 | Rickey et al. |
| 2003/0114837 A1 | 7/2003 | Drustrup |
| 2003/0138403 A1 | 7/2003 | Drustrup |
| 2003/0138491 A1 | 7/2003 | Tracy et al. |
| 2003/0157178 A1 | 8/2003 | Chen et al. |
| 2003/0170289 A1 | 9/2003 | Chen et al. |
| 2003/0180364 A1 | 9/2003 | Chen et al. |
| 2003/0186858 A1 | 10/2003 | Arentsen |
| 2003/0191099 A1 | 10/2003 | Bohlmann et al. |
| 2003/0211974 A1 | 11/2003 | Brodbeck et al. |
| 2003/0215515 A1 | 11/2003 | Truong-Le et al. |
| 2004/0001689 A1 | 1/2004 | Goldsmith et al. |
| 2004/0001889 A1 | 1/2004 | Chen et al. |
| 2004/0002442 A1 | 1/2004 | Pan et al. |
| 2004/0022859 A1 | 2/2004 | Chen et al. |
| 2004/0024068 A1 | 2/2004 | Chen et al. |
| 2004/0024069 A1 | 2/2004 | Chen et al. |
| 2004/0029784 A1 | 2/2004 | Hathaway |
| 2004/0039376 A1 | 2/2004 | Peery et al. |
| 2004/0047888 A1 | 3/2004 | Kenison et al. |
| 2004/0157951 A1 | 3/2004 | Glaesner et al. |
| 2004/0097906 A1 | 5/2004 | Fereira et al. |
| 2004/0101557 A1 | 5/2004 | Gibson et al. |
| 2004/0102762 A1 | 5/2004 | Gilbert |
| 2004/0115236 A1 | 6/2004 | Chan et al. |
| 2004/0142867 A1 | 7/2004 | Oi et al. |
| 2004/0142902 A1 | 8/2004 | Chen et al. |
| 2004/0151753 A1 | 8/2004 | Chen et al. |
| 2004/0198654 A1 | 10/2004 | Glaesner et al. |
| 2004/0209801 A1 | 10/2004 | Berry et al. |
| 2004/0224903 A1 | 11/2004 | Berry et al. |
| 2004/0225113 A1 | 11/2004 | LaFleur et al. |
| 2004/0243106 A1 | 12/2004 | Ayer |
| 2004/0265273 A1 | 12/2004 | Li et al. |
| 2004/0266683 A1 | 12/2004 | Hathaway et al. |
| 2004/0266692 A1 | 12/2004 | Young et al. |
| 2005/0004557 A1 | 1/2005 | Russell |
| 2005/0008661 A1 | 1/2005 | Fereira et al. |
| 2005/0009742 A1 | 1/2005 | Bertilsson et al. |
| 2005/0010196 A1 | 1/2005 | Fereira et al. |
| 2005/0070883 A1 | 3/2005 | Brown et al. |
| 2005/0070927 A1 | 3/2005 | Feinberg |
| 2005/0079200 A1 | 4/2005 | Rathenow et al. |
| 2005/0079202 A1 | 4/2005 | Chen et al. |
| 2005/0010942 A1 | 5/2005 | Eliaz et al. |
| 2005/0095284 A1 | 5/2005 | Trautman |
| 2005/0101943 A1 | 5/2005 | Ayer et al. |
| 2005/0106214 A1 | 5/2005 | Chen |
| 2005/0112188 A1 | 5/2005 | Eliaz et al. |
| 2005/0118206 A1 | 6/2005 | Luk et al. |
| 2005/0118221 A1 | 6/2005 | Blakely et al. |
| 2005/0131386 A1 | 6/2005 | Freeman et al. |
| 2005/0143749 A1 | 6/2005 | Zalenski et al. |
| 2005/0131389 A1 | 8/2005 | Pan et al. |
| 2005/0175701 A1 | 8/2005 | Pan et al. |
| 2005/0201980 A1 | 9/2005 | Moran |
| 2005/0215475 A1 | 9/2005 | Ong et al. |
| 2005/0216087 A1 | 9/2005 | Zucherman et al. |
| 2005/0266087 A1 | 12/2005 | Junnarkar et al. |
| 2005/0271702 A1 | 12/2005 | Wright et al. |
| 2005/0276856 A1 | 12/2005 | Fereira et al. |
| 2005/0281879 A1 | 12/2005 | Chen et al. |
| 2006/0013879 A9 | 1/2006 | Brodbeck et al. |
| 2006/0014678 A1 | 1/2006 | Cowley et al. |
| 2006/0030526 A1 | 2/2006 | Liu et al. |
| 2006/0069029 A1 | 3/2006 | Kolterman et al. |
| 2006/0073182 A1 | 4/2006 | Wong et al. |
| 2006/0084604 A1 | 4/2006 | Kitaura et al. |
| 2006/0084922 A1 | 4/2006 | Botha |
| 2006/0094652 A1 | 5/2006 | Levy et al. |
| 2006/0094693 A1 | 5/2006 | Aziz et al. |
| 2006/0106399 A1 | 5/2006 | Taras et al. |
| 2006/0141040 A1 | 6/2006 | Chen et al. |
| 2006/0142234 A1 | 6/2006 | Chen et al. |
| 2006/0160736 A1 | 7/2006 | Nadler |
| 2006/0178304 A1 | 8/2006 | Juul-Mortensen et al. |
| 2006/0193918 A1 | 8/2006 | Rohloff et al. |
| 2006/0216242 A1 | 9/2006 | Rohloff et al. |
| 2006/0224145 A1 | 10/2006 | Gills |
| 2006/0233841 A1 | 10/2006 | Brodbeck et al. |
| 2006/0246138 A1 | 11/2006 | Rohloff et al. |
| 2006/0251618 A1 | 11/2006 | Dennis et al. |
| 2006/0263433 A1 | 11/2006 | Ayer et al. |
| 2006/0264890 A1 | 11/2006 | Moberg et al. |
| 2006/0280795 A1 | 12/2006 | Penhasi et al. |
| 2006/0293232 A1 | 12/2006 | Levy et al. |
| 2007/0027105 A1 | 2/2007 | Junnarkar et al. |
| 2007/0149011 A1 | 6/2007 | Kent et al. |
| 2007/0166352 A1 | 7/2007 | Wright et al. |
| 2007/0248572 A1 | 10/2007 | Moran et al. |
| 2007/0281024 A1 | 12/2007 | Lautenbach et al. |
| 2008/0020016 A1 | 1/2008 | Li et al. |
| 2008/0038316 A1 | 2/2008 | Wong et al. |
| 2008/0064636 A1 | 3/2008 | Bloom et al. |
| 2008/0091176 A1 | 4/2008 | Alessi et al. |
| 2008/0065090 A1 | 5/2008 | Scribner et al. |
| 2008/0110515 A1 | 5/2008 | Angelosanto et al. |
| 2008/0112994 A1 | 5/2008 | Junnarkar et al. |
| 2008/0194985 A1* | 8/2008 | Nicoson ............ A61M 1/0084 600/566 |
| 2008/0200383 A1 | 8/2008 | Jennings et al. |
| 2008/0207512 A1 | 8/2008 | Roth et al. |
| 2008/0208194 A1 | 8/2008 | Bickenbach |
| 2008/0226625 A1 | 9/2008 | Berry et al. |
| 2008/0226689 A1 | 9/2008 | Berry et al. |
| 2008/0260838 A1 | 10/2008 | Hokenson et al. |
| 2008/0260840 A1 | 10/2008 | Alessi et al. |
| 2008/0269725 A1 | 10/2008 | Deem et al. |
| 2008/0312157 A1 | 12/2008 | Levy et al. |
| 2009/0022727 A1 | 1/2009 | Houston et al. |
| 2009/0036364 A1 | 2/2009 | Levy et al. |
| 2009/0042781 A1 | 2/2009 | Petersen et al. |
| 2009/0074734 A1 | 3/2009 | Rottiers |
| 2009/0087408 A1 | 4/2009 | Berry et al. |
| 2009/0156474 A1 | 6/2009 | Roth et al. |
| 2009/0163447 A1 | 6/2009 | Maggio |
| 2009/0186817 A1 | 7/2009 | Ghosh et al. |
| 2009/0202481 A1 | 8/2009 | Li et al. |
| 2009/0202608 A1 | 8/2009 | Alessi et al. |
| 2009/0209460 A1 | 8/2009 | Young et al. |
| 2009/0210019 A1 | 8/2009 | Kim et al. |
| 2009/0215694 A1 | 8/2009 | Kolterman et al. |
| 2009/0234392 A1 | 9/2009 | Dziedzic |
| 2009/0247463 A1 | 10/2009 | Wright et al. |
| 2009/0254143 A1 | 10/2009 | Tweden et al. |
| 2009/0286723 A1 | 11/2009 | Levy et al. |
| 2009/0312246 A1 | 12/2009 | Baron et al. |
| 2010/0092566 A1 | 4/2010 | Alessi et al. |
| 2010/0105627 A1 | 4/2010 | Salama et al. |
| 2010/0144621 A1 | 6/2010 | Kim et al. |
| 2010/0185184 A1 | 7/2010 | Alessi et al. |
| 2010/0297209 A1 | 11/2010 | Rohloff et al. |
| 2010/0298807 A1 | 11/2010 | Jansen et al. |
| 2010/0298840 A1 | 11/2010 | Schwartz |
| 2010/0331868 A1* | 12/2010 | Bardy ............ A61M 37/0069 606/167 |
| 2011/0076317 A1 | 3/2011 | Alessi et al. |
| 2011/0091527 A1 | 4/2011 | Moonen et al. |
| 2011/0104111 A1 | 5/2011 | Rohloff et al. |
| 2011/0152181 A1 | 6/2011 | Alsina-Fernandez et al. |

(56) References Cited

U.S. PATENT DOCUMENTS

| | | |
|---|---|---|
| 2011/0152182 A1 | 6/2011 | Alsina-Fernandez et al. |
| 2011/0160708 A1 | 6/2011 | Berry et al. |
| 2011/0166554 A1 | 7/2011 | Alessi et al. |
| 2011/0264077 A1 | 10/2011 | Rohloff et al. |
| 2011/0306549 A1 | 12/2011 | Tatarkiewicz et al. |
| 2012/0208755 A1 | 8/2012 | Leung |
| 2012/0303045 A1 | 11/2012 | Cooper et al. |
| 2013/0030417 A1 | 1/2013 | Alessi |
| 2013/0034210 A1 | 2/2013 | Rohloff et al. |
| 2013/0052237 A1 | 2/2013 | Eliaz et al. |
| 2013/0296661 A1 | 11/2013 | Bomzin et al. |
| 2013/0324977 A1 | 12/2013 | Vanderpool |
| 2014/0058409 A1 | 2/2014 | Bratlie |
| 2014/0058425 A1 | 2/2014 | Porat |
| 2014/0121741 A1 | 5/2014 | Bennett et al. |
| 2014/0236162 A1 | 8/2014 | Barongan |
| 2014/0257272 A1* | 9/2014 | Clark, III .............. A61M 37/00 606/37 |
| 2014/0324067 A1 | 10/2014 | Emken et al. |
| 2014/0378900 A1 | 12/2014 | Alessi et al. |
| 2015/0057227 A1 | 2/2015 | Leung |
| 2015/0111818 A1 | 4/2015 | Alessi et al. |
| 2015/0133791 A1 | 5/2015 | Sato et al. |
| 2015/0231062 A1 | 8/2015 | Lautenback et al. |
| 2015/0231256 A1 | 8/2015 | Berry et al. |
| 2015/0297509 A1 | 10/2015 | Schwarz |
| 2015/0359553 A1 | 12/2015 | Harnisch |
| 2016/0022582 A1 | 1/2016 | Alessi et al. |
| 2016/0030337 A1 | 2/2016 | Kuzma et al. |
| 2016/0354305 A1 | 12/2016 | Alessi et al. |
| 2017/0056476 A1 | 3/2017 | Rohloff et al. |
| 2017/0079906 A1 | 3/2017 | Alessi et al. |
| 2017/0119854 A1 | 5/2017 | Alessi et al. |
| 2017/0119855 A1 | 5/2017 | Berry et al. |
| 2017/0181964 A1 | 6/2017 | Lautenbach et al. |
| 2017/0252409 A1 | 9/2017 | Leung |
| 2017/0273706 A1 | 9/2017 | Mirza et al. |
| 2017/0319470 A1 | 11/2017 | Eliaz et al. |
| 2017/0319662 A1 | 11/2017 | Berry et al. |
| 2017/0348392 A1 | 12/2017 | Rohloff et al. |
| 2017/0368145 A1 | 12/2017 | Alessi et al. |
| 2018/0009871 A1 | 1/2018 | Blackwell et al. |

FOREIGN PATENT DOCUMENTS

| | | |
|---|---|---|
| EP | 0295411 | 12/1988 |
| EP | 0368339 | 5/1990 |
| EP | 0373867 | 6/1990 |
| EP | 0431942 | 6/1991 |
| EP | 0486959 A1 | 5/1992 |
| EP | 0521586 A1 | 1/1993 |
| EP | 0596161 | 5/1994 |
| EP | 0379147 | 9/1994 |
| EP | 0627231 | 12/1994 |
| EP | 0729747 | 5/1997 |
| EP | 0771817 | 5/1997 |
| EP | 0841359 | 5/1998 |
| EP | 0767689 | 6/1999 |
| EP | 1046399 | 10/2000 |
| EP | 1084703 | 3/2001 |
| EP | 1300129 A2 | 4/2003 |
| EP | 1300173 A2 | 4/2003 |
| EP | 1600187 | 1/2009 |
| EP | 2133073 A1 | 12/2009 |
| EP | 2020990 | 9/2010 |
| FR | 640907 | 7/1928 |
| GB | 1049104 | 11/1966 |
| GB | 1518683 | 7/1978 |
| GB | 2501400 | 10/2013 |
| JP | H02124814 A | 5/1990 |
| JP | H07196479 A | 8/1995 |
| JP | 9241153 | 9/1997 |
| JP | 11-100353 | 4/1999 |
| JP | 2006/213727 A | 8/2006 |
| JP | 2010-200838 | 9/2010 |
| NL | 9100160 | 8/1992 |
| NZ | 592113 | 8/2012 |
| RU | 2154501 | 8/2000 |
| RU | 87915 | 10/2009 |
| TW | 200634060 | 10/2006 |
| WO | WO1989003678 A1 | 5/1989 |
| WO | WO1990013285 A1 | 11/1990 |
| WO | WO1990013361 A1 | 11/1990 |
| WO | WO1990013780 A1 | 11/1990 |
| WO | WO 91/07160 | 5/1991 |
| WO | WO1992019241 A1 | 11/1992 |
| WO | WO 93/06819 | 4/1993 |
| WO | WO 93/06821 | 4/1993 |
| WO | WO 93/008832 | 5/1993 |
| WO | WO 93/09763 | 5/1993 |
| WO | WO 93/23083 | 11/1993 |
| WO | WO 94/09743 | 5/1994 |
| WO | WO1994010982 A1 | 5/1994 |
| WO | WO 94/21262 | 9/1994 |
| WO | WO 95/01167 | 1/1995 |
| WO | WO 95/09006 | 4/1995 |
| WO | WO 95/09007 | 4/1995 |
| WO | WO1995013799 A1 | 5/1995 |
| WO | WO 95/34285 | 12/1995 |
| WO | WO 96001134 | 1/1996 |
| WO | WO 96/003116 | 2/1996 |
| WO | WO1996036317 A1 | 11/1996 |
| WO | WO 96/39142 | 12/1996 |
| WO | WO 96/40049 | 12/1996 |
| WO | WO 96/40139 | 12/1996 |
| WO | WO 96/40355 | 12/1996 |
| WO | WO1996040049 A1 | 12/1996 |
| WO | WO 97/15289 | 5/1997 |
| WO | WO 97/15296 | 5/1997 |
| WO | WO 97/28181 | 8/1997 |
| WO | WO1997031943 A1 | 9/1997 |
| WO | WO1997044039 A1 | 11/1997 |
| WO | WO 97/46204 | 12/1997 |
| WO | WO 97/47339 | 12/1997 |
| WO | WO 98/00152 | 1/1998 |
| WO | WO 98/00157 | 1/1998 |
| WO | WO 98/00158 | 1/1998 |
| WO | WO 98/02169 | 1/1998 |
| WO | WO1997041837 A3 | 2/1998 |
| WO | WO1998007412 A1 | 2/1998 |
| WO | 9813092 A1 | 4/1998 |
| WO | WO 98/013092 A1 | 4/1998 |
| WO | WO 98/16250 | 4/1998 |
| WO | WO 98/17315 | 4/1998 |
| WO | WO 98/20930 | 5/1998 |
| WO | WO 98/27960 | 7/1998 |
| WO | WO 98/027962 | 7/1998 |
| WO | WO 98/27963 | 7/1998 |
| WO | WO 98/030231 | 7/1998 |
| WO | WO 98/32463 | 7/1998 |
| WO | WO1998030231 A1 | 7/1998 |
| WO | WO 98/42317 | 10/1998 |
| WO | WO 98/47487 | 10/1998 |
| WO | WO 98/51282 | 11/1998 |
| WO | WO 99/03453 | 1/1999 |
| WO | WO 99/04767 | 2/1999 |
| WO | WO 99/004768 | 2/1999 |
| WO | WO1999012549 A2 | 3/1999 |
| WO | WO 99/16419 | 4/1999 |
| WO | WO 99/025728 | 5/1999 |
| WO | WO 99/29306 | 6/1999 |
| WO | WO 99/033446 | 7/1999 |
| WO | WO 99/33449 | 7/1999 |
| WO | WO 99/39700 | 8/1999 |
| WO | WO 99/040788 | 8/1999 |
| WO | WO 99/044659 | 9/1999 |
| WO | WO 99/062501 | 12/1999 |
| WO | WO 99/064061 | 12/1999 |
| WO | WO 00/013663 | 3/2000 |
| WO | WO 00/029206 | 5/2000 |
| WO | WO 00/038652 | 7/2000 |
| WO | WO 00/039280 | 7/2000 |
| WO | WO 00/040273 | 7/2000 |

(56) References Cited

FOREIGN PATENT DOCUMENTS

| | | |
|---|---|---|
| WO | WO 00/041548 | 7/2000 |
| WO | WO 00/045790 | 8/2000 |
| WO | WO 00/054745 | 9/2000 |
| WO | WO2000059476 A1 | 10/2000 |
| WO | WO 00/066138 | 11/2000 |
| WO | WO 00/067728 | 11/2000 |
| WO | WO2000066087 A2 | 11/2000 |
| WO | WO2001019345 A1 | 3/2001 |
| WO | WO2001028525 A2 | 4/2001 |
| WO | WO 01/043528 | 6/2001 |
| WO | WO 01/051041 | 7/2001 |
| WO | WO 01/78683 | 10/2001 |
| WO | WO 02/028366 | 4/2002 |
| WO | WO 02/036072 | 5/2002 |
| WO | WO 02/043800 | 6/2002 |
| WO | WO 02/045752 | 6/2002 |
| WO | WO 02/47716 | 6/2002 |
| WO | WO 02/067895 | 9/2002 |
| WO | WO 02/069983 | 9/2002 |
| WO | 02083216 A1 | 10/2002 |
| WO | WO 02/76344 | 10/2002 |
| WO | WO 02/085428 | 10/2002 |
| WO | WO 03/000230 | 1/2003 |
| WO | WO 03/007981 | 1/2003 |
| WO | WO 03/011892 | 2/2003 |
| WO | WO 03/024357 | 3/2003 |
| WO | WO 03/024503 | 3/2003 |
| WO | WO2003020245 A1 | 3/2003 |
| WO | WO 03/030923 | 4/2003 |
| WO | WO 03/041684 | 5/2003 |
| WO | WO 03/041757 | 5/2003 |
| WO | WO 03/053400 | 7/2003 |
| WO | WO2003066585 A2 | 8/2003 |
| WO | WO 03/072113 | 9/2003 |
| WO | WO 03/072133 | 9/2003 |
| WO | WO 04/002565 | 1/2004 |
| WO | WO2004034975 A2 | 4/2004 |
| WO | WO2004035754 A2 | 4/2004 |
| WO | WO2004035762 A2 | 4/2004 |
| WO | WO2004036186 A2 | 4/2004 |
| WO | WO 04/052336 | 6/2004 |
| WO | WO 04/056338 | 7/2004 |
| WO | WO 04/089335 | 10/2004 |
| WO | WO2004103342 A2 | 12/2004 |
| WO | WO 05/048930 | 6/2005 |
| WO | WO 05/048952 | 6/2005 |
| WO | WO 05/102293 | 11/2005 |
| WO | WO2005102293 A1 | 11/2005 |
| WO | WO2005110425 | 11/2005 |
| WO | WO 06/017772 | 2/2006 |
| WO | WO 06/023526 | 3/2006 |
| WO | WO 06/081279 | 8/2006 |
| WO | WO 06/083761 | 8/2006 |
| WO | WO 06/084139 | 8/2006 |
| WO | WO 06/086727 | 8/2006 |
| WO | WO 06/101815 | 9/2006 |
| WO | WO 06/111169 | 10/2006 |
| WO | WO2006/131730 | 12/2006 |
| WO | WO 07/024700 | 3/2007 |
| WO | WO 07/056681 | 5/2007 |
| WO | WO 07/075534 | 7/2007 |
| WO | WO 07/084460 | 7/2007 |
| WO | WO 07/133778 | 11/2007 |
| WO | WO 07/140416 | 12/2007 |
| WO | WO 08/021133 | 2/2008 |
| WO | WO2008041245 A2 | 4/2008 |
| WO | WO 08/061355 | 5/2008 |
| WO | WO2008/086086 A2 | 7/2008 |
| WO | 2008131440 A1 | 10/2008 |
| WO | 2008139303 A2 | 11/2008 |
| WO | WO 08/133908 | 11/2008 |
| WO | WO 08/134425 | 11/2008 |
| WO | WO 09/109927 | 9/2009 |
| WO | WO2009143285 A2 | 11/2009 |
| WO | 2010045169 A1 | 4/2010 |
| WO | 2011011697 A1 | 1/2011 |
| WO | WO 2013/004983 A1 | 1/2013 |
| WO | WO 2013/118109 A1 | 8/2013 |
| WO | 2013160347 A1 | 10/2013 |
| WO | 2013184235 A1 | 12/2013 |

OTHER PUBLICATIONS

Ahn et al., "A New Approach to Search for the Bioactive Confirmation of Glucagon: Positional Cyclization Scanning" Journal of Medicinal Chemistry, vol. 44, No. 19, (2001): 3109-3116.

International Search Report and Written Opinion issued by The International Searching Authority for Application No. PCT/US2016/035602, dated Nov. 29, 2016, 20 pages.

Glumetza Brochure 2009, 13 Pages.

Erowid,"Introduction to the Federal Controlled Substance Analog Act" 2001.

Li et al. ("Glucagon-Like Peptide-I Receptor Agonists Versus Insulin Glargine for Type 2 Diabetes Mellitus: A Systematic Review and Meta-Analysis of Randomized Controlled Trials" in Current Therapeutic Research, vol. 71, No. 4, Aug. 2010.

Akers, et al., "Formulation Design and Development of Parenteral Suspensions," Journal of Parenteral Science & Technology, 41(3): 88-96 (1987).

Alonso, et al., "Determinants of Release Rate of Tetanus Vaccine from Polyester Microspheres," Pharmaceutical Research, 10(7):945-953 (1993).

Beck, et al., "Poly(dl-lactide-co-glycolide)/norethisterone microcapsules: An injectable biodegradable contraceptive," Biology of Reproduction, 28(1): 186-195 (1983).

Bodmeier and McGinity, "Solvent selection in the preparation of poly(dl-lactide) microspheres prepared by the solvent evaporation method," International Journal of Pharmaceutics, 43(1-2): 179-186 (Apr. 1988).

Cha and Pitt, "A one-week subdermal delivery system for I-methadone based on biodegradable microcapsules," Journal of Controlled Release, 7: 69-78 (1988).

Cha and Pitt, "The acceleration of degradation-controlled drug delivery from polyester microspheres," Journal of Controlled Release, 8: 259-265 (1989).

Cohen, et al., "Controlled delivery systems for proteins based on poly(lactic/glycolic acid) microspheres," Pharmaceutical Research, 8(6): 713-720 (1991).

Conti, et al., "Use of polylactic acid for the preparation of microparticulate drug delivery systems," Journal of Microencapsulation, 9(2): 153-166 (1992).

Hodgman, et al., Eds., Handbook of Chemistry and Physics, 35th Edition, 1024-1025 (1953).

Jalil and Nixon, "Biodegradable poly(lactic acid) and poly(lactide-co-glycolide) microcapsules: Problems associated with preparative techniques and release properties," Journal of Microencapsulation, 7(3): 297-325 (Jul.-Sep. 1990).

Lee and Timasheff, "The stabilization of proteins by sucrose," J. Biological Chem., 256(14): 7193-7201 (Jul. 1981).

Li, et al., "Prediction of solvent removal profile and effect on properties for peptide-loaded PLGA microspheres prepared by solvent extraction/evaporation method," Journal of Controlled Release, 37: 199-214 (1995).

Maa and Hsu, "Liquid-liquid emulsification by static mixers for use in microencapsulation," Journal of Microencapsulation, 13(4): 419-433 (Jul.-Aug. 1996).

Maulding, et al., "Biodegradable microcapsules: Acceleration of polymeric excipient hydrolytic rate by incorporation of a basic medicament," Journal of Controlled Release, 3: 103-117 (1986).

Mehta, et al.,"Peptide containing microspheres from low molecular weight and hydrophilic poly(d,l-lactide-co-glycolide)," Journal of Controlled Release, 41: 249-257 (1996).

Sah, et al., "A novel method of preparing PLGA microcapsules utilizing methylethyl ketone," Pharmaceutical Research, 13(3): 360-367 (1996).

(56) References Cited

OTHER PUBLICATIONS

Sato, et al., "Porous biodegradable microspheres for controlled drug delivery. I. Assessment of processing conditions and solvent removal techniques," Pharmaceutical Research, 5(1): 21-30 (1988).

Szayna, et al., "Exendin-4 decelerates food intake, weight gain, and fat deposition in Zucker rats," Endocrinology, 141(6): 1936-1941 (2000).

Thomasin, et al., "A contribution to overcoming the problem of residual solvents in biodegradable microspheres prepared by coacervation," Eur. J. Pharm. Biopharm., 42(1): 16-24 (1996).

Van Santbrink and Fauser, "Urinary follicle-stimulating hormone for normogonadotropic colomiphene-resistant anovulatory infertility: Prospective, randomized comparison between low dose step-up and step-down dose regimens," J. Clin. Endocrin. Metab., 82(11): 3597-3602 (1997).

Tracy et al., "Factors affecting the degradation rate of poly(lactide-co-glycolide) microspheresin vivo and in vitro." Biomaterials. 20(11:): 1057-1062 (1999).

Ertl et al., "Poly (DL-lactide-co-glycolide) microspheres as carriers for peptide vaccines," Vaccine 14(9):879-885.(1996).

Thompson et al., "Biodegradable microspheres as a delivery system for rismorelin porcine, a porcine-growth-hormone-releasing hormone," Journal of Controlled Release 43(1):9-22 (1997).

Adolf, "Human interferon omega-a review," Mult. Sclr. 1:S44-47 (1995).

Costantino et al., "Protein Spray Freeze Drying. 2. Effect of Formulation Variables on particle Size and Stability," J. Pharm. Sci. 91:388-395 (2002).

Henry et al., "Comparing ITCA 650, continuous subcutaneous delivery of exenatide via DUROS® device, vs. twice daily exenatide injections in metformin-treated type 2 diabetes," oral presentation at the 46th Annual Meeting of the European Association for the Study of Diabetes in Stockholm, Sweden , 21 pages (Sep. 20-24, 2010).

Huggins et al., "Synergistic antiviral effects of ribavirin and the C-nucleoside analogs tiazofurin and selenazofurin against togaviruses, bunyaviruses, and arenaviruses," Antimicrobial Agents & Chemotherapy, 26(4):476-480 (1984).

Ishiwata et al., "Clinical effects of the recombinant feline interferon-omega on experimental parvovirus infection in beagle dogs," J. Vet. Med. Sci. 60(8):911-917 (1998).

Johnson et al., "How interferons fight disease," Sci. Am. 270(5):68-75 (May 1994).

Lublin et al., "Defining the clinical course of multiple sclerosis: results of an international survey," Neurology. 46:907-911 (1996).

Madsbad, "Exenatide and liraglutide: different approaches to develop GLP-1 receptor agonists (incretin mimetics)—preclinical and clinical results," Best Practice & Research Clinical Endocrinology & Metabolism 23:463-77 (2009).

Nielsen, "Incretin mimetics and DPP-IV inhibitors for the treatment of type 2 diabetes," Drug Discovery Today 10(10):703-710 (May 15, 2005).

Palmeri et al., "5-Fluorouracil and recombinant α-interferon-2a in the treatment of advanced colorectal carcinoma: a dose optimization study," J. Chemotherapy 2(5):327-330 (Oct. 1990).

Patti et al., "Natural interferon-b treatment of relapsing-remitting and secondary-progressive multiple sclerosis patients: two-year study," Acta. Neurol. Scand. 100:283-289 (1999).

Paty et al., "Interferon beta-1 b is effective in relapsing-remitting multiple sclerosis," Neurology 43:662-667 (1993).

PCT International Search Report for PCT/US2009/000916, 4 pages (Aug. 12, 2009).

"Intarcia Therapeutics Announces Final Results from a Phase 2 Study of Injectable Omega Interferon plus Ribavirin for the Treatment of Hepatits C Genotype-1 ," NLV Partners Press Coverage Portofolio News (Apr. 12, 2007) (Press Release).

Quianzon et al., "Lixisenatide-Once-daily Glucagon-like Peptide-1 Diabetes," US Endocrinology 7(2):104-109 (2011).

Ratner et al., "Dose-dependent effects of the one-daily GLP-1 receptor agonist lixisenatide in patients with Type 2 diabetes inadequately controlled with metfmmin: a randomized, double-blind, placebo-controlled trial," Diabetic Medicine 27(9):1024-1032 (Sep. 2010).

Roberts et al., "The Evolution of the Type I Interferons1," J. Interferon Cytokine Res. 18(10):805-816 (Oct. 1998).

Rohloff et al., "Duros Technology Delivers Peptides and Proteins at Consistent Rate Continuously for 3 to 12 Months," J. Diabetes Sci. & Tech., 2(3):461-467 (May 1, 2008).

"Sequence Listings for International Patent Application Publication No. W02009109927, WIPO Patentscope", http://patentscope.wipo.int/search/docservicepdf_pc!id00000008776887, 1 page (last visited Nov. 14, 2012).

Shire et al., "Challenges in the Development of High Protein Concentration Formulations," J. Pharm. Sci. 93:1390-1402 (2004).

Smith, "Peripheral Neuro-hormones as a Strategy to Treat Obesity," oral presentation at the 2007 Cardiometabolic Health Congress in Boston, MA, pp. 1-35 (Sep. 26-29, 2007).

Written Opinion for International Patent Application No. PCT/US2009/005629 (corresponding to U.S. Appl. No. 12/587,946), 5 pages (Apr. 15, 2011).

Zhang et al., "Efficacy observations of different dosages of interferon to treat 150 Hepatitis B carriers," Current Physician 2(12):45-46 (1997).

Partial Supplementary European Search Report for European Application No. 16804481.6, dated Jan. 24, 2019.

Pratley et al., "Targeting Incretins in Type 2 Diabetes: Role of GLP-1 Receptor Agonists and DPP-4 Inhibitors," Rev. Diabet. Stud., 5(2):73-94 (2008).

Sanofi-Aventis U.S. LLC, Prescribing Information for ADLYXIN® (Lixisenatide) Injection, for Subcutaneous Use, rev. Jul. 2016, 31 pages.

Amylin Pharmaceuticals, Inc., Prescribing Information for BYETTA® (Exenatide) Injection, rev. Oct. 2009, 34 pages.

AstraZeneca Pharmaceuticals LP, Prescribing Information for BYDUREON® (Exenatide Extended-Release for Injectable Suspension), rev. Mar. 2015, 60 pages.

Novo Nordisk A/S, Prescribing Information for Victoza® (Liraglutide [rDNA Origin] Injection), Solution for Subcutaneous Use, v. 1, Jan. 2010, 23 pages.

GlaxoSmithKline LLC, Prescribing Information for TANZEUM® (Albiglutide) for Injection, for Subcutaneous Use, rev. Jun. 2014, 55 pages.

Eli Lilly & Company, Prescribing Information for TRULICITY® (Dulaglutide) Injection, for Subcutaneous Use, rev. Mar. 2015, 19 pages.

"Abstracts 2007," Diabetologia Clinical & Experimental Diabetes & Metabolism, Springer, Berlin, Germany, vol. 50 S243 (Aug. 21, 2007) (paragraph [0586]) (XP002538652).

Jetschmann et al., "Open-label rising-dose study of omega interferon in IFN-naive patients with chronic hepatitis C," Gastroenterology 122:A278-A347 (Apr. 1, 2002) (Abstract M1454).

Bray, "Gut Signals and Energy Balance: Ghrelin, Peptide YY, Leptin, and Amylin," (Dec. 19, 2007) (slides and transcript for presentation at Medscape CME).

"Implantable infusion pumps: technology poised for takeoff," BBI Newsletter 17(12):209-211 (Dec. 1994).

Adamson et al., "Phase I trial and pharmacokinetic study of all-trans-retinoic acid administered on an intermittent schedule in combination with interferon-alpha2a in pediatric patients with refractory cancer," J. Clin. Oncol. 15(11):3330-3337 (Nov. 1997).

Adolf et al., "Monoclonal antibodies and enzyme immunoassays specific for human interferon (IFN) ω1: evidence that IFN-ω1 is a component of human leukocyte IFN," Virology 175(2):410-471 (Apr. 1990).

Adolf et al., "Antigenic structure of human interferon ω1 (Interferon αII): comparison with other human interferons," J. Gen. Virol. 68(6):1669-1676 (Jun. 1987).

Adolf et al., "Purification and characterization of natural human interferon ω1," J. Bio. Chem. 265(16):9290-9295 (Jun. 1990).

Adolf et al., "Human interferon ω1: isolation of the gene, expression in Chinese hamster ovary cells and characterization of the recombinant protein," Biochim. Biophys. Acta 108(9):167-174 (Jun. 1991).

(56) References Cited

OTHER PUBLICATIONS

ANDRX Pharmaceuticals, LLC, ANDA for Concerta® Extended-Release Tablets, 6 pages (correspondence dated Sep. 6, 2005).
ASTM International, Annual Book of ASTM Standards, 8.02:208-211, 584-587 (1984).
Ansel et al., "Dosage Form Design: Pharmaceutical and Formulation Considerations," Pharmaceutical Dosage Forms and Drug Delivery Systems, Ch. 3 at 87-92 (7th ed. Lippincott Williams & Wilkins 1999).
Ansel et al., "Modified-Release Dosage Forms and Drug Delivery Systems," Pharmaceutical Dosage Forms and Drug Delivery Systems, Ch. 8 at 229-243 (7th ed. Lippincott Williams & Wilkins 1999).
Aulitzky, "Successful Treatment of Metastatic Renal Cell Carcinoma With a Biologically Active Dose of Recombinant Interferon-Gama," Journal of Clinical Oncology 7(12):1875-1884 (1989).
Hauck, "Engineers Guide to Plastics," Materials Engineering 5(72):38-45 (Jul. 17, 1972).
Bailon et al., "Rational Design of a Potent, Long-lasting Form of Interferon: A 40 kDa Branched Polyethylene Glycol-conjugated Interferon Alpha-2a for the Treatment of Hepatitis C," Bioconjugate Chemistry 12(2):195-202 (2001).
Bakan et al., "Physicochemical Characterization of a Synthetic Lipid Emulsion for Hepatocyte-Selective Delivery of Lipophilic Compounds: Application to Polyiodinated triglycerides as Contrast Agents for Computed Tomography," J. Pharm. Sci., 85(9):908-914 (1996).
Bakhtiar et al, "Taking Delivery," Soap Perfumery & Cosmetics 76(3):59-65 (2003) (liposomes in cosmetic delivery systems).
Balkwill,F., "Interferons," Lancet 1(8646):1060-1063 (May 1989).
Bauer et al., "Non-aqueous emulsions as vehicles for capsule fillings," Drug Dev. & Industrial Pharmacy 10(5):699-712 (1984).
Bekkering et al., "Estimation of early hepatitis C viral clearance in patients receiving daily interferon and ribavirin therapy using a mathematical model," Hepatology 33(2):419-423 (Feb. 2001).
Bell et al., "Hamster preproglucagon contains the sequence of glucagon and two related peptides," Nature 302:716-718 (1983).
Bell et al, "Impact of moisture on thermally induced denaturation and decomposition of lyophilized bovine somatotropin," Drug Delivery Research & Dev. Biopolymers, (35):201-209 (1995).
Bertoncello et al., "Haematopoietic radioprotection by Cremophor EL: a polyethoxylated castor oil," Int. J. Radiat. Biol. 67(1):57-64 (1995).
Bohlinder et al., "Use and characteristics of a novel lipid particle-forming matrix as a drug-carrier system," Euro. J. Pharm. Sci. 2(4):271-279 (1994).
Bolinger et al., "Recombinant interferon γ for treatment of chronic granulomatous disease and other disorders," Clin. Pharm. 11(10):834-850 (Oct. 1992).
Bonkovsky et al., "Outcomes research in chronic viral hepatitis C: effects of interferon therapy," Can. J. Gastroenterol. 14(Supp. B):21B-29B (Jul.-Aug. 2000).
Borden et al., "Second-generation interferons for cancer: clinical targets," Semin. Cancer Biol. 10(2):125-144 (Apr. 2000).
Boué et al., "Antiviral and antiluteolytic activity of recombinant bovine IFN-ω1 obtained from Pichia pastoris," J. Interferon & Cytokine Res. 20:677-683 (2000).
Buckwold et. al. "Antiviral activity of CHO-SS cell-derived human omega interferon and other human interferons against HCV RNA replicons and related viruses," Antiviral Res. 73(2):118-25 (Feb. 2007) (Epub Sep. 11, 2006).
Cantor, "Theory of lipid monolayers comprised of mixtures of flexible and stiff amphiphiles in anthermal solvents: fluid phase coexistence," J. Chem. Physics 104(20):8082-8095 (1996).
CAS No. 56-81-5 (Nov. 16, 1984).
Chang et al., "Biodegradeable polyester implants and suspension injection for sustained release of a cognitive enhancer," Pharm. Tech. 20(1):80-84 (1996).

Chapman et al., "Physical Studies of Phospholipids. VI. Thermotropic and Lyotropic Mesomorphism of Some 1,2-Diacylphosphatidylcholines (lecithins)," Chem. & Physics of Lipids 1(5):445-475 (1967).
Chaumeil, "Micronization: a method of improving the bioavailability of poorly soluble drugs," Methods & Findings in Experimental & Clinical Pharmacology 20(3):211-215 (1998).
Clark et al., "The diabetic Zucker fatty rat," Proc. Soc. Exp. Biol. 173(1):68-75 (1983).
Condino-Neto, "Interferon-γ improves splicing efficiency of CYBB gene transcripts in an interferon responsive variant of chronic granulomatous disease due to a splice site consensus region mutation," Blood 95(11):3548-3554 (Jun. 2000).
Darney, "Subdermal progestin implant contraception," Current Opinion in Obstetrics & Gynecology 3:470-476 (1991).
Das, S. et al., "Reviewing Antisense Oligonucleotide Therapy: Part 2, Delivery Issues," BioPharm, 2(11):44-51 (1999).
Dash, A. K. et al., "Therapeutic applications of implantable drug delivery systems," Journal of Pharmacological and Toxicological Methods, 40(1):1-12 (1998).
Davis et al., "Durability of viral response to interferon alone or in combination with oral ribavirin in patients with chronic hepatitis C," Prog. Abstr. 50th Annu. Mtg. Postgrad. Courses Am. Assn. Study Liver Dis., Dallas, TX (Nov. 5-9, 1999)(Abstract 570 ).
Deacon, C. F. et al., "GLP-1-(9-36) amide reduces blood glucose in anesthetized pigs by a mechanism that does not involve insulin secretion," Am. J. Physiol. Endocrinol. Metab., 282:E873-E879 (2002).
Desai et al., "Protein structure in the lyophilized state: a hydrogen isotope exchange/NMR study with bovine pancreatic trypsin inhibitor," J. Am. Chem. Soc. 116(21):9420-9422 (1994).
Di Marco et al., "Combined treatment of relapse of chronic hepatitis C with high-dose α-2B interferon plus ribavirin for 6 or 12 months," Prog. Abstr. 50th Annu. Mtg. Postgrad. Courses Am. Assn. Study Liver Dis., Dallas, TX (Nov. 5-9, 1999)(Abstract 569).
Dorr et al., "Phase I-II trial of interferon-alpha 2b by continuous subcutaneous infusion over 28 days," J. Interferon Res. 8:717-725 (1988).
Uhlig et al., "The electro-smotic acutation of implantable insulin micropumps," J. Biomed. Materials Res. 17:931-943 (1983).
Efendic, S. et al., et al., "Overview of incretin hormones," Horm. Metab. Res., 36(11-12):742-746 (2004).
Eissele, R. et al., "Rat gastric somatostatin and gastrin release: interactions of exendin-4 and truncated glucagon-like peptide-1 (GLP-1) amide," Life Sci., 55(8):629-634 (1994).
Elias et al., "Infusional Interleukin-2 and 5-fluorouracil with subcutaneous interferon-α for the treatment of patients with advanced renal cell carcinoma: a southwest oncology group Phase II study," Cancer 89(3):597-603 (Aug. 2000).
Eng, J. et al., "Isolation and characterization of exendin-4, an exendin-3 analogue, from Heloderma suspectum venom. Further evidence for an exendin receptor on dispersed acini from guinea pig pancreas," J. Biol. Chem., 267(11):7402-7405 (1992).
Eng, J. et al., "Purification and structure of exendin-3, a new pancreatic secretagogue isolated from Heloderma horridum venom," J. Biol. Chem., 265(33):20259-20262 (1990).
Eppstein et al., "Biological activity of liposome-encapsulated murine interferon γ is mediated by a cell membrane receptor," PNAS USA 82:3688-3692 (1985).
Eros et al., "Multiple phase emulsions as controlled drug delivery therapeutic systems," Proc.-Conf. Colloid Chem. 193-196 (1993).
Fang et al., "The impact of baseline liver histology on virologic response to interferon α-2b±p ribavirin therapy in patients with chronic hepatitis C," Prog. Abstr. 50th Annu. Mtg. Postgrad. Courses Am. Assn. Study Liver Dis., Dallas, TX (Nov. 5-9, 1999)(Abstract 572).
Felker et al., "The Rate of Transfer of Unesterified Cholesterol from Rat Erythrocytes to Emulsions Modeling Nascent Triglyceride-Rich Lipoproteins and Chylomicrons Depends on the Degree of Fluidity of the Surface," J. Nutritional Biochem. 4(1):630-634 (1993).
Ferenci et al, "Combination of interferon (IFN) induction therapy and ribavirin in chronic hepatitis C," Prog. Abstr. Dig. Dis. Week 2000, San Diego, CA (May 21-24, 2000) (Abstract 977).

(56) References Cited

OTHER PUBLICATIONS

Fontaine et al., "Recovery from chronic hepatitis C in long-term responders to ribarivin plus interferon α," Lancet 356(9223):41 (Jul. 2000).
Franchetti et al., "Furanfurin and Thiophenfurin: Two Novel TiazofurinAnalogues. Synthesis, Structure, Antitumor Activity, and Interactions with Inosine Monophosphate Dehydrogenase," J. Medicinal Chem. 38(19):3829-3837 (1995).
Fujii et al., "Effect of phosphatidylcholine on Skin Permeation of Indomethacin from gel prepared with Liquid Paraffin and Hydrogenated Phospholipid," Int'l J. Pharmaceutics 222(1):57-64 (2001).
Fujii et al., "Enhancement of skin permeation of miconazole by phospholipid and dodecyl 2-(N, N-dimethylamino) propionate (DDAIP)," Int'l J. Pharmaceutics 234(1-2):121-128 (2002).
Luft et al., "Electro-osmotic valve for the controlled administration of drugs," Med. & Biological Engineering & Computing 45-50 (Jan. 1978) (non-English with English abstract).
Gan To Kagaku Ryoho, "Phase II study of recombinant leukocyte A interferon (Ro22-8181) in malignant brain tumors," Cancer & Chemotherapy 12(4):913-920 (Apr. 1985) (non-English with English abtract).
Gappa et al., "Juvenile laryngeal papillomatosis—a case report," Pneumologie 45(11):936-938 (Nov. 1991) (XP009079028) (non-English with English abstract).
Gause et al., "Phase I study of subcutaneously administered interleukin-2 in combination with interferon alfa-2a in patients with advanced cancer," J. Clin. Oncol. 14(8):2234-2241 (Aug. 1996).
Ghiglione, M., et al., "How glucagon-like is glucagon-like peptide-1?" Diabetologia 27:599-600 (1984).
Glue et al., "A dose-ranging study of Peg-intron and ribavirin in chronic hepatitis C—safety, efficacy, and virological rationale," Prog. Abstr. 50th Annu. Mtg. Postgrad. Courses Am. Assn. Study Liver Dis., Dallas, TX(Nov. 5-9, 1999)(Abstract 571).
Goke, R. et al., "Exendin-4 is a high potency agonist and truncated exendin-(9-39)-amide an antagonist at the glucagon-like peptide 1-(7-36)-amide receptor of insulin-secreting beta-cells," J. Biol. Chem., 268(26):19650-19655 (1993).
Gonzales et al., "Randomized controlled trial including an initial 4-week 'induction' period during one year of high-dose interferon α-2B treatment for chronic hepatitis C," Prog. Abstr. Dig. Dis. Week 2000, San Diego, CA (May 21-24, 2000) (Abstract 975).
Gosland et al., "A phase I trial of 5-day continuous infusion cisplatin and interferon alpha," Cancer Chemother. Pharmacol. 37(1-2):39-46 (1995).
Grant et al., "Combination therapy with interferon-α plus N-acetyl cystein for chronic hepatitis C: a placebo controlled double-blind multicentre study," J. Med. Virol. 61(4):439-442 (Aug. 2000).
Gutniak, M. et al., "Antidiabetogenic effect of glucagon-like peptide-1 (7-36)amide in normal subjects and patients with diabetes mellitus," N. Engl. J. Med., 326(20):1316-1322 (1992).
Hageman, "The Role of Moisture in Protein Stability," Drug Dev. & Ind. Pharm. 14(14):2047-2070 (1988).
Heathcote et al., "Peginterferon alfa-2a in Patients With Chronic Hepatitis C and Cirrhosis," New England J. Med. 343(23):1673-1680 (2000).
Heim et al., "Intracellular signaling and antiviral effects of interferons," Dig. Liver Dis. 32(3):257-263 (Apr. 2000).
Heinrich, G. et al., "Pre-proglucagon messenger ribonucleic acid: nucleotide and encoded amino acid sequences of the rat pancreatic complementary deoxyribonucleic acid," Endocrinol., 115:2176-2181 (1984).
Hellstrand et al., "Histamine and cytokine therapy," Acta Oncol. 37(4):347-353 (1998).
Hellstrand et al., "Histamine and the response to IFN-α in chronic hepatitis C," Interferon Cytokine Res. 18(1):21-22 (Jan. 1998).
Hellstrand et al., "Histamine in immunotherapy of advanced melanoma: a pilot study," Cancer Immunol Immunother. 39(6):416-419 (Dec. 1994).

Hisatomi et al., "Toxicity of polyoxyethylene hydrogenated castor oil 60 (HCO-60) in experimental animals," J. Toxicol. Sci., 18(3):1-9 (1993).
Hodoshima, N. et al., "Lipid nanoparticles for delivering antitumor drugs," International Journal of Pharmaceutics, 146(1):81-92 (1997).
Hoffmann-La Roche Inc., Pegasys® (peginterferon alfa-2a), 15 pages (2002).
Horton et al., "Antitumor effects of interferon-omega: in vivo therapy of human tumor xenografts in nude mice" Cancer Res 59(16):4064-4068 (Aug. 1999).
Hubel et al., "A phase I/II study of idarubicin, dexamethasone and interferon-alpha (1-Dexa) in patients with relapsed or refractory multiple myeloma" Leukemia 11 Suppl 5:S47-S51 (Dec. 1997).
Iacobelli et al., "A phase I study of recombinant interferon-alpha administered as a seven-day continuous venous infusion at circadian-rhythm modulated rate in patients with cancer," Am. J. Clin. Oncol. 18(1):27-31 (1995).
IFNB Multiple Sclerosis Study Group, "Interferonβ-1b is effective in relapsing-remitting multiple sclerosis," Neurology 43(4):655-667 (Apr. 1993).
INTERMUNE® Inc., Infergen® (Interferon alfacon-1), 5 pages (2002).
"Introduction to Antibodies", http://www.chemicon.com/resource/ANT101/a1.asp, 8 pages (retrieved May 2, 2007).
Isaacs et al., "Virus interference. I. The interferon," Pro. R. Soc. Lond. B. Biol. Sci. 147:258-267 (1957).
Jain et al., "Controlled delivery of drugs from a novel injectable in situ formed biodegradable PLGA microsphere system," J. Microencapsulation 17(3):343-362 (2000).
Jordan et al., "Guidelines for Antiemetic Treatment of Chemotherapy-Induced Nausea and Vomiting: Past, Present and Future Recommendations," The Oncologist 12(9):1143-1150 (2007).
Kabalnov et al., "Macroemulsion type and stability of alkane-water-phospholipid systems," Abstracts of Papers, Part 1, 210th ACS National Meeting, 0-8412-3222-9, American Chemical Society, Chicago, IL (Aug. 20-24, 1995) (Abstract only).
Kabalnov et al., "Phospholipids as Emulsion Stabilizers.2. Phase Behavior Versus Emulsion Stability," Journal of Colloid and Interface Science 184(1):227-235 (1996).
Khalili et al., "Interferon and ribavirin versus interferon and amantadine in interferon nonresponders with chronic hepatitis C," Am. J. Gastroenterol. 95(5):1284-1289 (May 2000).
Kildsig et al., "Theoretical Justification of Reciprocal Rate Plots in Studies of Water Vapor Transmission through Films," J. Pharma. Sci. 29(11):1634-01637 (Nov. 17, 1970).
Kirkwood et al., "Interferon alfa-2b adjuvant therapy of high-risk resected cutaneous melanoma: The Eastern Cooperative Oncology Group Trial EST 1684," J. Clin. Oncol. 14(1):7-17 (1996).
Kita et al., "Characterization of a polyethylene glycol conjugate of recombinant human interferon-γ," Drug Des. Deliv. 6(3):157-0167 (Sep. 1990).
Knepp et al, "Identification of antioxidants for prevention of peroxide-mediated oxidation of recombinant human ciliary neurotrophic factor and recombinant human nerve growth factor," J. Pharm. Sci. Tech. 50(3):163-171 (1996).
Knepp et al., "Stability of nonaqueous suspension formulations of plasma derived factor IX and recombinant human alpha interferon at elevated temperatures," Pharma. Res. 15(7):1090-1095 (1998).
Knobler et al., "Systemic α-interferon therapy of multiple sclerosis," Neurology 34(10):1273-1279 (Oct. 1984).
Kovacevic et al., "Treatment of chronic viral hepatitis B in secondary membranoproliferative glomerulonephritis using recombinant α-2 interferon," Maksic Dj Vojnosanit. Pregl. 57(2):235-240 (Mar.-Apr. 2000) (non-English with English abstract).
Kracke et al., "Mx proteins in blood leukocytes for monitoring interferon 62 -1b therapy in patients with MS," Neurology 54(1):193-199 (Jan. 2000).
Kronenberger et al., "Influence of interferon-α on CD82-expression in HCV-positive patients," Prog. Abstr. Dig. Dis. Week 2000, San Diego, CA (May 21-24, 2000) (Abstract 976).
Krown et al., "Interferons and interferon inducers in cancer treatment," Semin. Oncol. 13(2):207-217 (1986).

(56) References Cited

OTHER PUBLICATIONS

Kubes et al., "Cross-species antiviral and antiproliferative activity of human interferon-ω," J. Interferon Res. 14:57-59 (1994).
Kunzi et al., "Role of interferon-stimulated gene ISG-15 in the interferon-ω-mediated inhibition of human immunodeficiency virus replication," J. Interferon Cytokine Res. 16(11):919-927 (Nov. 1996).
Larsson, "Stability of emulsions formed by polar lipids," Progress in the Chemistry of Fats and Other Lipids 16:163-0169 (1978).
Lee et al., "Dynamics of hepatitis C virus quasispecies turnover during interferon-A treatment," Prog. Abstr. Dig. Dis. Week 2000, San Diego, CA (May 21-24, 2000) (Abstract 974).
Lee, "Therapy of hepatits C: interferon alfa-2A trials," Hepatology 26: 89S-95S (Sep. 1997) (XP000981288).
Lopez, L. C. et al., "Mammalian pancreatic preproglucagon contains three glucagon-related peptides," Proc. Natl. Acad. Sci. USA, 80(18):5485-5489 (1983).
Lukaszewski et al., "Pegylated α interferon is an effective treatment for virulent Venezuelan equine encephalitis virus and has profound effects on host immune response to infection," J. Virol. 74(11):5006-5015 (Jun. 2000).
Lund, P. K. et al., "Pancreatic preproglucagon cDNA contains two glucagon-related coding sequences arranged in tandem," Proc. Natl. Acad. Sci. USA, 79(2):345-349 (1982).
Lundberg, "A submicron lipid emulsion coated with amphipathic polyethylene glycol for parenteral administration of paclitaxel (Taxol)," J. Pharm. & Pharmacol. 49(1):16-21 (1997).
Magnuson et al. "Enhanced recovery of a secreted mammalian protein from suspension culture of genetically modified tobacco cells," Protein Expression & Purification 7:220-228 (1996).
Malley et al., "Chronic Toxicity and Oncogenicity of N-Methylpyrrolidone (Nmp) in Rats and Mice by Dietary Administration," Drug Chem Toxicol. 24(4):315-38 (Nov. 2001).
Manning et al, "Stability of protein pharmaceuticals," Pharm. Res. 6(11):903-918 (1989).
Marincola et al., "Combination therapy with interferon alfa-2a and interleukin-2 for the treatment of metastatic cancer," J. Clinical Oncol. 13(5):1110-1122 (1995) (XP009078965).
Massey, "Interaction of vitamin E with saturated phospholipid bilayers," Biochem. & Biophys. Res. Comms. 106(3):842-847 (1982).
McHutchison et al., "Interferon α-2b alone or in combination with ribavirin as initial treatment for chronic hepatitis C," N. Engl. J. Med. 339(21):1485-1492 (Nov. 1998).
McHutchison, et al., "Open-label phase 1B study of hepatitis C viral dynamics with omega interferon treatment," Hepatology 34(4):A333 (Oct. 1, 2001) (XP004716177) (Abstract Only).
Meier, J. J. et al., "The glucagon-like peptide-1 metabolite GLP-1-(9-36) amide reduces postprandial glycemia independently of gastric emptying and insulin secretion in humans," Am. J. Physiol. Endocrinol. Metab., 290(6):E1118-E1123 (2006).
Merad et al., "Generation of monocyte-derived dendritic cells from patients with renal cell cancer: modulation of their functional properties after therapy with biological response modifiers (IFN-α plus IL-2 and IL-12)," J. Immunother. 23(3):369-378 (May-Jun. 2000).
Milella et al., "Neutralizing antibodies to recombinant α-interferon and response to therapy in chronic hepatitis C infection," Liver 13(3):146-150 (Jun. 1993).
Mohler, "Primer on electrodeposited coatings," Materials Engineering 5:38-45 (1972).
Mojsov, S., "Structural requirements for biological activity of glucagon-like peptide-I," Int. J. Peptide Protein Research, 40:333-343 (1992).
Morgan, "Structure and Moisture Permeability of Film-Forming Poloyers," Ind. Eng. Chem. 45(10):2296-2306 (1953).
Motzer et al., "Phase I trial of 40-kd branched pegylated interferon alfa-2a for patients with advanced renal cell carcinoma," J. Clinical Oncol. 19(5):1312-1319 (2001).
Nauck, M. A. et al., "Normalization of fasting glycaemia by intravenous GLP-1 ([7-36 amide] or [7-37]) in type 2 diabetic patients," Diabet. Med., 15(11):937-945(1998).
Neumann et al., "Hepatitis C Viral Dynamics In Vivo and the Antiviral Efficacy of Interferon-alpha Therapy," Science 282:103-107 (Dec. 1998).
Nieforth et al., "Use of an indirect pharmacodynamic stimulation model of MX protein induction to compare in vivo activity of interferon-α-2a and a polyethylene glycol-modified derivative in healthy subjects," Clin. Pharmacol. Ther. 59(6):636-646 (Jun. 1996).
Norden et al., "Physicochemical characterization of a drug-containing phospholipid-stabilized o / w emulsion for intravenous administration," Eur. J. Pharm. Sci. 13(4):393-401 (2001).
Olaso et al., "Early prediction of lack of response to treatment with interferon and interferon plus ribavirin using biochemical and virological criteria in patients with chronic hepatitis C," Esp. Quimioter. 12(3):220-228 (Sep. 1999) (non-English with English abstract).
Ortiz, A. et al., "A differential scanning calorimetry study of the interaction of α-tocopherol with mixtures of phospholipids," Biochim et Biophys Acta 898(2):214-222 (1987).
Panitch, "Interferons in multiple sclerosis," Drugs 44(6):946-962 (Dec. 1992).
Patzelt, C. et al., "Identification and processing of proglucagon in pancreatic islets," Nature, 282:260-266 (1979).
Peterson, R. G. et al., "Zucker Diabetic Fatty Rat as a Model for Non-insulin-dependent Diabetes Mellitus," ILAR Journal, 32(3):16-19 (1990).
Peterson, R. G. et al., "Neuropathic complications in the Zucker diabetic fatty rat (ZDF/Drt-fa)," Frontiers in diabetes research. Lessons from Animal Diabetes III, Shafrir, E. (ed.), pp. 456-458, Smith-Gordon, London (1990).
Pimstone et al., "High dose (780 MIU/52 weeks) interferon monotherapy is highly effective treatment for hepatitis C," Prog. Abstr. Dig. Dis. Week 2000, San Diego, CA (May 21-24, 2000) (Abstract 973).
Plauth et al, "Open-label phase II study of omega interferon in previously untreated HCV infected patients," Hepatology 34(4):A331 (Oct. 1, 2001) (XP004716169) (Abstract Only).
Plauth et al, "Open-label study of omega interferon in previously untreated HCV-infected patients," J. Hepatology 36(Supp. 1):125 (Apr. 2002) (XP002511882) (Abstract Only).
Pohl, M. et al., "Molecular cloning of the helodermin and exendin-4 cDNAs in the lizard. Relationship to vasoactive intestinal polypeptide/ pituitary adenylate cyclase activating polypeptide and glucagon-like peptide 1 and evidence against the existence of mammalian homologues," J. Biol. Chem., 273(16):9778-9784 (1998).
Poynard et al., "Is an 'a la carte' combined interferon α 2b plus ribavirin possible for the first line treatment in patients with chronic hepatitis C," Hepatology 31(1):211-218 (Jan. 2000).
Poynard et al., "Randomized trial of interferon α 2b plus ribavirin for 48 weeks or for 24 weeks versus interferon α 2b plus placebo for 48 weeks for the treatment of chronic infection with hepatitis C virus," Lancet 352(9138):1426-1432 (Oct. 1998).
"Intarcia Presents Positive ITCA 650 Phase 2 Study Results for Type 2 Diabetes at EASD,"Intarcia Therapeutics, Inc. (Sep. 22, 2010) (Press Release).
Quesada et al., "Interferons in Hematological Malignancies", eds. Baron et al., U. Tex. 487-495 (1987).
Quintanar-Guerrero et al., "Applications of the ion-pair concept to hydrophilic substances with special emphasis on peptides," Pharm. Res. 14(2):119-127 (1997).
Rajkumar et al., "Phase I evaluation of radiation combined with recombinant interferon alpha-2a and BCNU for patients with high-grade glioma," Int'l J. Radiat. Oncol. Biol. Phys. 40(2):297-302 (Jan. 15, 1998).
Roche Pharmaceuticals, Roferon®-A (Interferon alfa-2a, recombinant), 22 pages (2003).
Roff et al., "Handbook of Common Polymers", Cleveland Rubber Co. 72 pages (1971).
Rogers et al., "Permeability Valves," Ind. & Eng. Chem. 49(11):1933-1936 (Nov. 17, 1957).

(56) References Cited

OTHER PUBLICATIONS

Roman et al., "Cholestasis in the rat by means of intravenous administration of cyclosporine vehicle, Cremophor EL," Transplantation 48(4);554-558 (1989).
Roth et al., "High Dose Etretinate and Interferon-alpha—A Phase I Study in Squamous Cell Carcinomas and Transitional Cell Carcinomas," Acta Oncol. 38(5):613-617 (1999).
Roth et al., "Combination therapy with amylin and peptide YY[3-36] in obese rodents: anorexigenic synergy and weight loss additivity," Endocrinol. 148(12):6054-61 (Dec. 2007).
Schepp, W. et al., "Exendin-4 and exendin-(9-39)NH2: agonist and antagonist, respectively, at the rat parietal cell receptor for glucagon-like peptide-1-(7-36)NH2," Eur. J. Pharmacol., 269(2):183-191 (1994).
Schering Corp., Intron® A for Injection, 6 pages (2001).
Schering Corp., PEG-Intron™ (Peginterferon alfa-2b) Powder for Injection, 29 pages (2003).
Schmalfub, et al., "Modification of drug penetration into human skin using microemulsions," J. Controlled Release 46(3):279-285 (1997).
Sen et al., "The interferon system: a bird's eye view of its biochemistry," J. Biol. Chem. 267(8):5017-5020 (Mar. 1992).
Shiffman et al., "A decline in HCV-RNA level during interferon or ihterferon/ribavirin therapy in patients with virologic nonresponse is associated with an improvement in hepatic histology," Prog. Abstr. 50th Annu. Mtg. Postgrad. Courses Am. Assn. Study Liver Dis., Dallas, TX (Nov. 5-9, 1999) (Abstract 567).
Shima et al., "Serum total bile acid level as a sensitive indicator of hepatic histological improvement in chronic hepatitis C patients responding to interferon treatment," J. Gastroenterol. Hepatol. 15(3):294-299 (Mar. 2000).
Shiratori et al., "Histologic improvement of fibrosis in patients with hepatitis C who have sustained response to interferon therapy," Ann. Int. Med. 132(7):517-524 (Apr. 2000).
Simon et al., "A longitudinal study of T1 hypointense lesions in relapsing MS: MSCRG trial of interferon β1a," Neurology 55(2):185-192 (Jul. 2000).
Sparks, J. D. et al., "Lipoprotein alterations in 10- and 20-week-old Zucker diabetic fatty rats: hyperinsulinemic versus insulinopenic hyperglycemia," Metabolism, 47(11):1315-1324 (1998).
Sulkowskli et al., "Pegylated Interferon Alfa-2A (Pegasys™) and Ribavirin Combination Therapy for Chronic Hepatitis C: A Phase II Open-Label Study," Gastroenterology 118(4, Supp. 2) (2000) (Abstract 236).
Sulkowski, M., et al., "Peginterferon-α-2a (40kD) and ribavirin in patients with chronic hepatitis C: a phase II open label study," Biodrugs 16(2):105-109 (2002).
Talpaz et al., "Phase I study of polyethylene glycol formulation of interferon alpha-2B (Schering 54031) in Philadelphia chromosome-positive chronic myelogenous leukemia," Blood 98(6):1708-1713 (2001).
Talsania, T., et al., "Peripheral exendin-4 and peptide YY(3-36) synergistically reduce food intake through different mechanisms in mice," Endocrinology 146(9):3748-56 ( Sep. 2005).
Tanaka, H., et al., "Effect of interferon therapy on the incidence of hepatocellular carcinoma and mortality of patients with chronic hepatitis C: a retrospective cohort study of 738 patients," Int. J. Cancer 87(5):741-749 (Sep. 2000).
Tong et al., "Prediction of response during interferon α 2b therapy in chronic hepatitis C patients using viral and biochemical characteristics: a comparison," Hepatology 26(6):1640-01645 (Dec. 1997).
Touza Rey et al., "The clinical response to interferon-γ in a patient with chronic granulomatous disease and brain abscesses due to Aspergillus fumigatus," Ann. Med. Int. 17(2):86-87 (Feb. 2000).
Trudeau et al., "A phase I study of recombinant human interferon alpha-2b combined with 5-fluorouracil and cisplatin in patients with advanced cancer," Cancer Chemother. Pharmacol. 35(6):496-500 (1995).

Tseng, C. C. et al., "Glucose-dependent insulinotropic peptide: structure of the precursor and tissue-specific expression in rat," PNAS USA, 90(5):1992-1996 (1993).
Tsung et al., "Preparation and Stabilization of Heparin/Gelatin Complex Coacervate Microcapsules," J. Pharm. Sci. 86(5):603-7 (May 1997).
Unniappan et al., "Effects of dipeptidyl peptidase IV on the satiety actions of peptide YY," Diabetologia; Clinical and Experimental Diabetes and Metabolism 49(8):1915-1923 (Jun. 27, 2006).
Vokes et al., "A phase I trial of concomitant chemoradiotherapy with cisplatin dose intensification and granulocyte-colony stimulating factor support for advanced malignancies of the chest," Cancer Chemother. Pharmacol. 35(4):304-312 (1995).
Vrabec, J. T., "Tympanic membrane perforations in the diabetic rat: a model of impaired wound healing," Otolaryngol. Head Neck Surg., 118(3 Pt. 1):304-308 (1998).
Wang et al., "Preferential interaction of α-tocopherol with phosphatidylcholines in mixed aqueous dispersions of phosphatidylcholine and phosphatidylethanolamine," Eur. J. Biochem. 267(21):6362-6368 (2000).
Wang et al., "Ripple phases induced by α-tocopherol in saturated diacylphosphatidylcholines," Archives of Biochem. & Biophys. 377(2):304-314 (2000).
Wang et al., "The distribution of α-tocopherol in mixed aqueous dispersions of phosphatidylcholine and phosphattidylethanolamine," Biochimica et Biophysica Acta-Biomembranes 1509(1-2):361-372 (2000).
Wang et al, "Parenteral formulations of proteins and peptides: stability and stabilizers," J. Parenter. Sci. Technol. 42(2S):S4-S26 (1988).
Weinstock-Guttman et al., "What is new in the treatment of multiple sclerosis?" Drugs 59(3):401-410 (Mar. 2000).
Weissmann et al., "The interferon genes," Prog. Nucleic Acid Res. Mol. Biol. 33:251-300 (1986).
Wright et al., "Preliminary experience with α-2b-interferon therapy of viral hepatitis in liver allograft recipients," Transplantation 53(1):121-123 (Jan. 1992).
Young et al., "Glucose-lowering and insulin-sensitizing actions of exendin-4: studies in obese diabetic (ob/ob, db/db) mice, diabetic fatty Zucker rats, and diabetic rhesus monkeys (*Macaca mulatta*)," Diabetes, 48(5):1026-1034 (1999).
Younossi et al., "The role of amantadine, rimantadine, ursodeoxycholic acid, and NSAIDs, alone or in combination with α interferons, in the treatment of chronic hepatitis C," Semin. Liver Dis. 19(Supp. 1):95-102 (1999).
Yu et al., "Preparation, characterization, and in vivo evaluation of an oil suspension of a bovine growth hormone releasing factor analog," J. Pharm. Sci. 85(4):396-401 (1996).
Zeidner et al., "Treatment of FeLV-induced immunodeficiency syndrome (feLV-FAIDS) with controlled release capsular implantation of 2',3'-dideoxycytidine," Antivir. Res. 11(3):147-0160 (Apr. 1989).
Zein, "Interferons in the management of viral hepatitis," Cytokines Cell Mol. Ther. 4(4):229-241 (Dec. 1998).
Zeuzem et al., "Peginterferon Alfa-2a in Patients with Chronic Hepatitis C," New Engl. J. Med. 343(23):1666-1672 (2000).
Zeuzem et al., "Hepatitis C virus dynamics in vivo: effect of ribavirin and interferon α on viral turnover," Hepatology 28(1):245-252 (Jul. 1998).
Zhang et al., "Report on Large Dosage Interferon to Treat 30 Cases of Viral Encephalitis," J. Clinical Pediatrics 14(2):83-84 (1996).
Zhang et al, "A new strategy for enhancing the stability of lyophilized protein: the effect of the reconstitution medium on keratinocyte growth factor," Pharm. Res. 12(10):1447-1452 (1995).
Zheng et al. "Therapeutic Effect of Interferon Varied Dose in Treating Virus Encephalitis," Beijing Med. J. 13(2):80-81 (1998).
Ziesche et al., "A preliminary study of long-term treatment with interferon γ-1b and low-dose prednisolone in patients with idiopathic pulmonary fibrosis," New Engl. J. Med. 341(17):1264-1269 (Oct. 1999).

\* cited by examiner

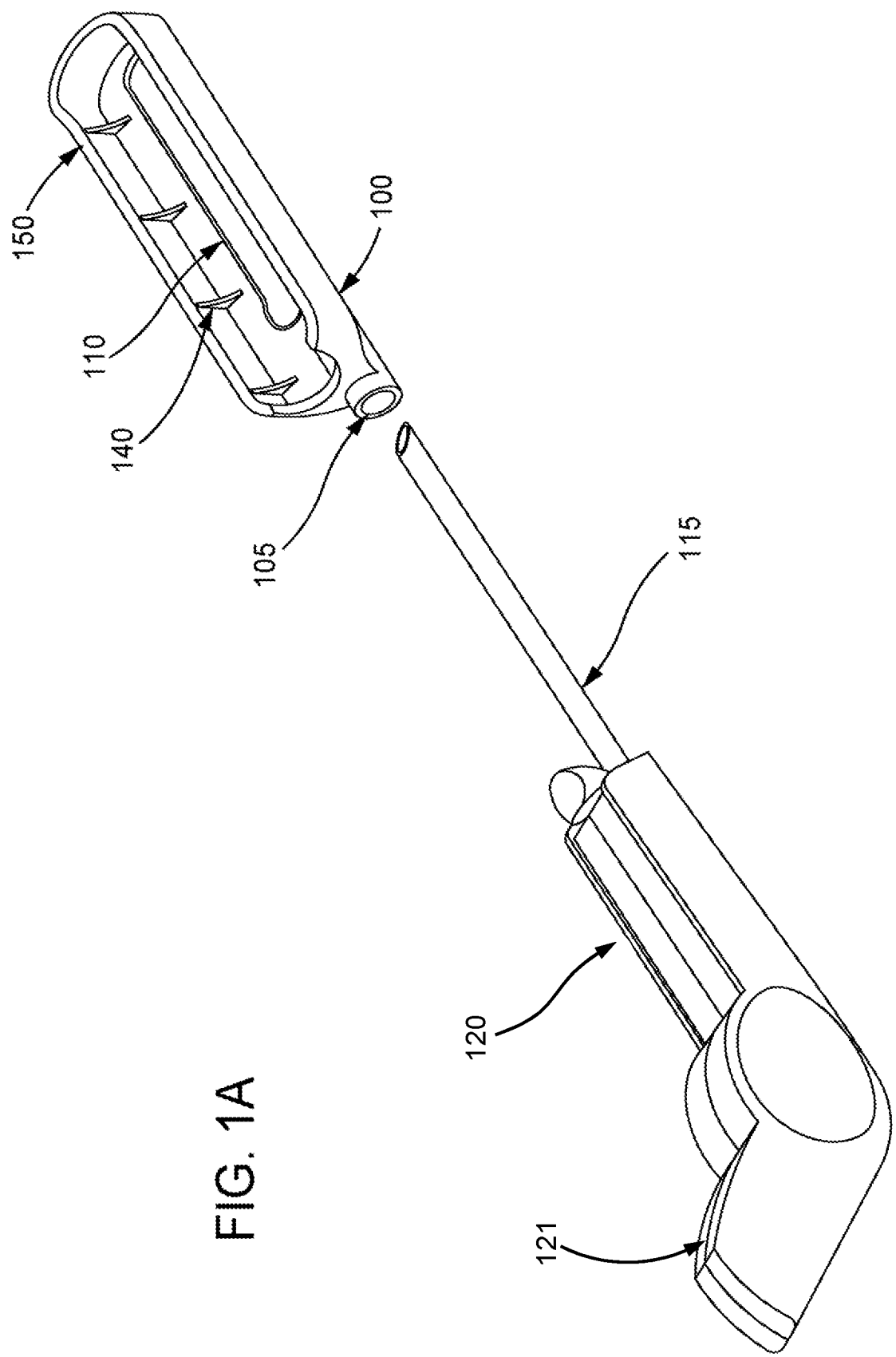

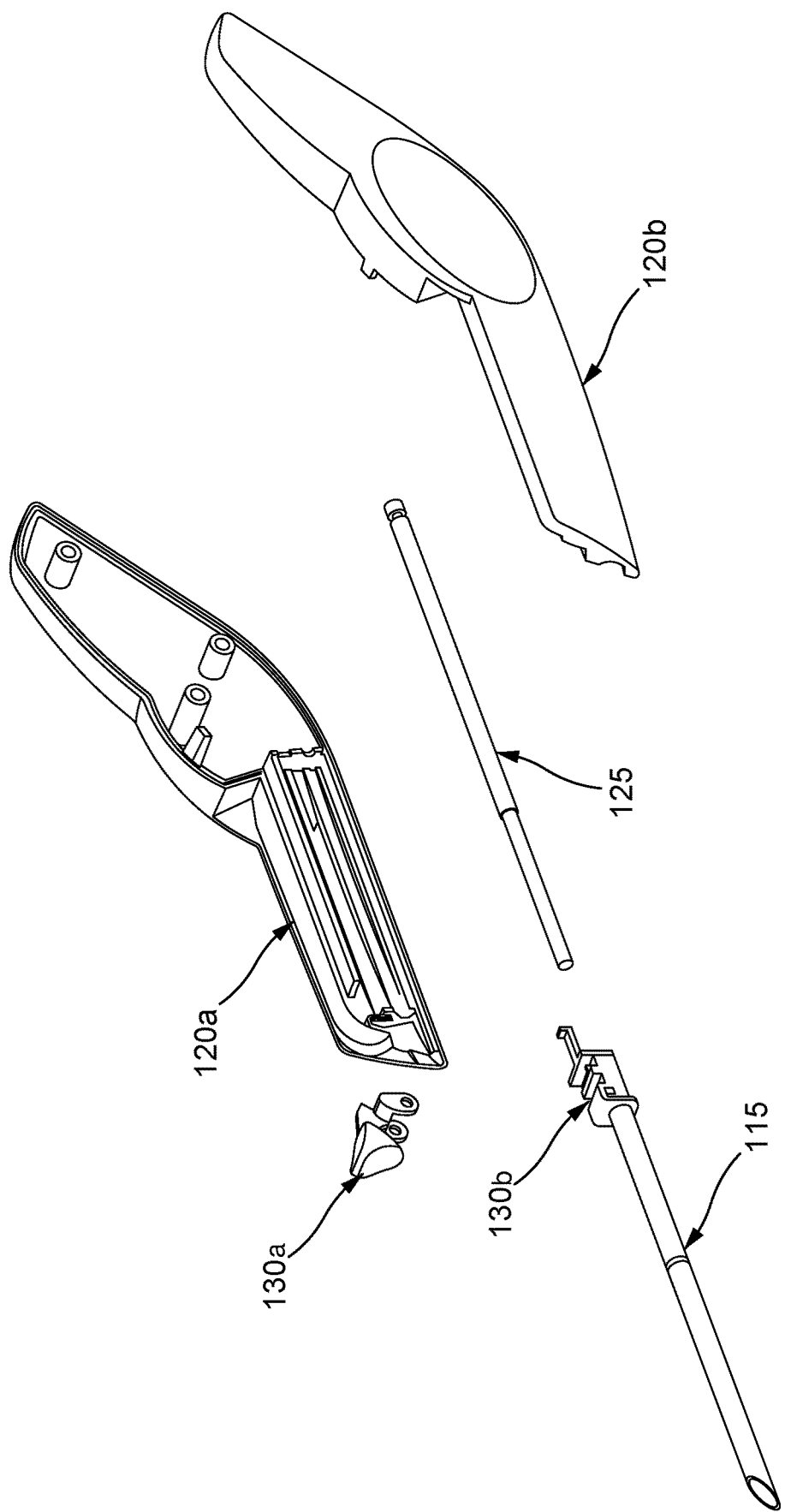

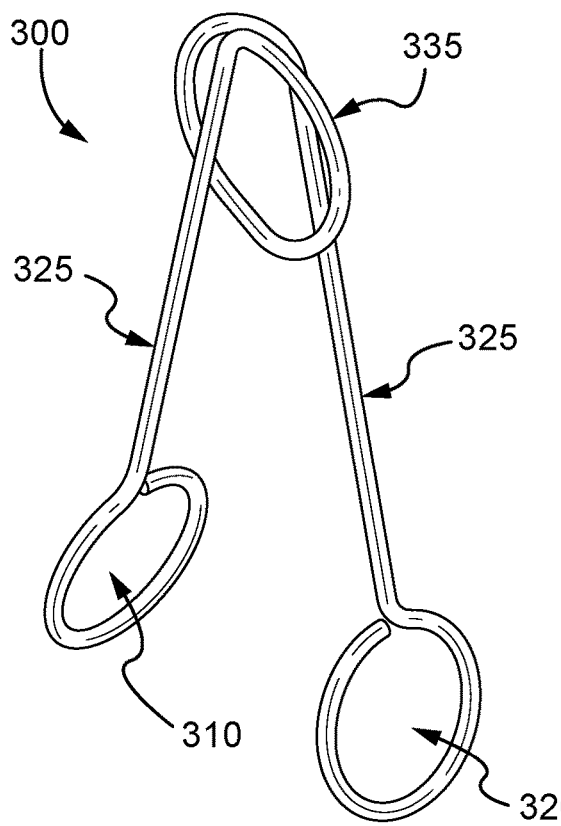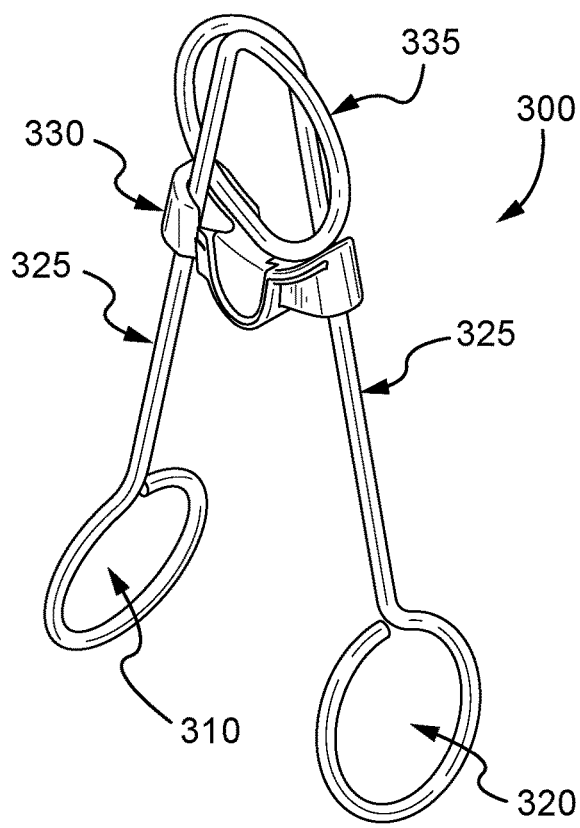
FIG. 10A    FIG. 10B
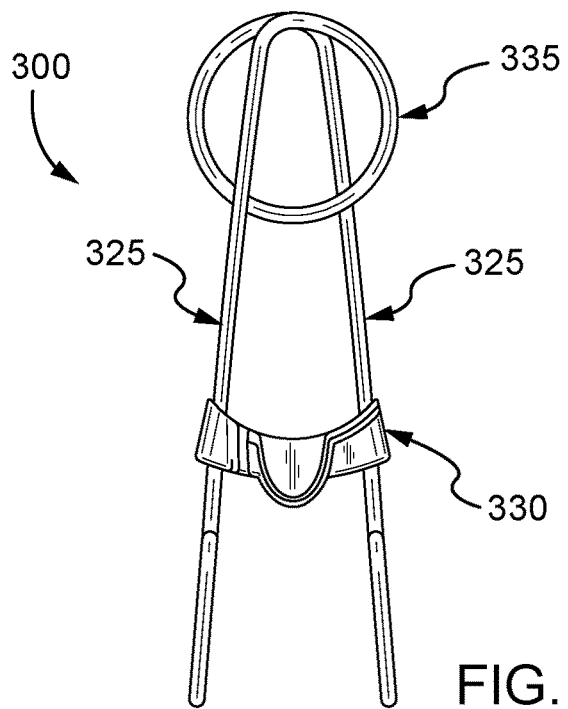
FIG. 10C

IMPLANT PLACEMENT AND REMOVAL SYSTEMS

CROSS-REFERENCE TO RELATED APPLICATIONS

This application claims priority to U.S. Provisional Patent Application No. 62/170,561, filed Jun. 3, 2015, and entitled "Subcutaneous Implant Placement System," and U.S. Provisional Patent Application No. 62/170,994, filed Jun. 4, 2015, and entitled "Subcutaneous Implant Placement System." The present application incorporates herein by reference the disclosures of all of the above-referenced applications in their entireties.

FIELD OF THE INVENTION

Embodiments of the present disclosure relate to systems, methods and devices for placing and removing an implant at/from a determined depth beneath an outer surface of skin.

SUMMARY OF SOME OF THE EMBODIMENTS

Some embodiments of this disclosure present systems, methods and devices which guide placement of implants at a determined depth within tissue, beneath the outer surface of skin, as well as for the removal of the implants from within tissue, such as intraepidermal, subepidermal, intradermal, subdermal, intracutaneous, and/or subcutaneous tissue. Systems, methods and devices herein can be adapted for placement of implants to any determined depth. In some embodiments, the determined depth of the implant upon placement is about 0.5 mm to about 4.5 mm, about 1 mm to about 4 mm, about 1.5 mm to about 3 mm, beneath an outer surface of skin of a patient, such as a human patient. In some embodiments, systems, methods and devices are provided to guide placement of implants into or among intraepidermal, subepidermal, intradermal, subdermal, intracutaneous, and/or subcutaneous tissue depths.

In some embodiments, a system for placing an implant at a determined depth beneath an outer surface of skin is provided which comprises a placement tool including a handle portion and a placement cannula movable within or adjacent to, and relative to, the handle portion. The cannula has a length, a proximal end arranged near the handle portion and a distal end opposite the proximal end, and is configured to govern and restrict placement of the implant to a determined depth beneath an outer surface of skin of a patient. Placement is made via an incision in the outer surface of skin at an implantation site.

The system also includes a placement guide having a first surface and a pilot-tube. The pilot-tube includes a proximal end with a pilot-hole configured to receive the distal end of the placement cannula, a distal end spaced apart from the proximal end at a first distance, a longitudinal central axis arranged relative to the first surface at either or both of a second distance and an angle. The placement guide is configured to guide the placement cannula within an incision in tissue to govern and restrict placement of the implant to a determined placement depth. During insertion of the cannula into the incision, prior to release of the implant from the cannula, the handle portion and cannula can be rotated by a practitioner, in clockwise and counterclockwise directions, e.g., back and forth within a span or range of between about 9 o'clock to about 3 o'clock, about 10 o'clock and about 2 o'clock, or about 11 o'clock to about 1 o'clock, relative to the central longitudinal axis of the pilot-tube on the placement guide. Rotation in this manner, while the placement guide remains substantially stationary, without rotating, on the outer surface of the skin of the patient, promotes controlled and proper progression of the cannula into the tissue of the patient beneath the outer surface of skin. Thus, in some embodiments, the placement guide is configured to allow substantially free rotation of the cannula within the pilot-tube of the placement guide. In some embodiments, a system is provided for placing an implant into and/or among intraepidermal, subepidermal, intradermal, subdermal, intracutaneous, and/or subcutaneous tissue.

In such systems (and other embodiments), one and/or another of the following features may be included:
at least one of the first distance, the second distance and the angle are configured to guide the placement cannula and deliver the implant at the determined depth beneath the outer surface of the skin of the patient;
the placement guide further comprises a visualization window or opening which extends along a length and a width of the placement guide and which is configured to enable visualization and/or palpitation of an area of skin around the site at which the implant is being inserted;
the implant may be any implant such as, e.g., an implantable osmotic mini-pump;
the determined depth of the implant is about 0.5 mm to about 4.5 mm, about 1 mm to about 4 mm, and about 1.5 mm to about 3 mm, beneath the outer surface of skin of the patient;
the pilot-tube is configured to receive and guide the placement cannula into tissue.

In some embodiments, a method is provided for placing an implant and comprises providing a placement system (e.g., according to embodiments disclosed herein). In some embodiments, the method for placing an implant further comprises at least one of: loading the implant into the distal end of the placement cannula, creating an incision in the skin at an implantation site, arranging the placement guide at the implantation site, such that the distal end of the pilot-tube is aligned with the incision, inserting the distal end of the loaded placement cannula in the proximal end of the pilot-tube, moving the placement cannula relative to the pilot-tube until at least a part of the handle portion is proximate the proximal end of the pilot-tube such that the distal end of the placement cannula is guided further into the incision and into the tissue beneath and/or adjacent to the incision, releasing the implant from the placement cannula at the determined depth, removing the placement cannula from the skin of the patient, and removing the placement guide from the skin of the patient. In some embodiments, the placement cannula is properly guided farther into the incision, at a determined depth beneath the skin's outer surface, upon rotation of the handle portion and the cannula. In some embodiments, a method for placing an implant at a determined depth is provided. In some embodiments, a method is provided for placing an implant into and/or among intraepidermal, subepidermal, intradermal, subdermal, intracutaneous, and/or subcutaneous tissue.

The above method embodiments may additionally include one or more of the following features:
prior to creating the incision, the method further includes one or more of cleaning the skin at the implantation site, marking the skin for making the incision, and injecting a local anesthetic in a vicinity of the mark;
after release and/or removal of the placement cannula, and/or removal of the placement guide, the method further comprises at least one of: cleaning the incision, applying pressure to the incision, applying an adhesive to at least one side of the incision, and closing the incision; and the determined depth is about 0.5 mm to about 4.5 mm, about 1 mm to about 4 mm, about 1.5 mm to about 3 mm, beneath the outer surface of the skin of the patient.

In some embodiments for placing an implant, both ends of the implant are placed at a determined depth that is substantially the same, resulting in a substantially level placement of the implant. In other words, each end of the implant is placed at a determined depth that is within about 0.5 mm, about 0.4 mm, about 0.3 mm, about 0.2 mm, or about 0.1 mm of the other end.

In some embodiments, a placement guide device for use with an implant placement tool is provided and includes a first surface and a pilot-tube having a central longitudinal axis. The tube includes a proximal end configured to receive the distal end of a placement cannula for delivering an implant into tissue and a distal end spaced apart from the proximal end at a first distance. The longitudinal axis arranged relative to the first surface at either or both of a second distance and an angle and the placement guide are configured to guide a placement cannula of a placement tool within the tissue to effect implantation of the implant at a determined placement depth beneath the outer surface of the skin of the patient. In some embodiments, the placement guide is made from a material (e.g., medical-grade plastic) that is translucent or substantially clear. In some embodiments, the placement guide is substantially rigid. For example, in some embodiments, the placement guide is sufficiently rigid that it cannot be substantially flexed, warped or bent, length-wise and/or width-wise, by a user during normal usage. In some embodiments, a placement guide device is provided for use with a placement tool. In some embodiments, a placement guide device is provided for placing an implant into and/or among intraepidermal, subepidermal, intradermal, subdermal, intracutaneous, and/or subcutaneous tissue.

The placement guide, according to some embodiments, may include one and/or another of the following features:

a visualization window or opening which extends along a length and a width of the first surface and configured to enable visualization and/or palpitation of an area of skin around the site at which the implant is being inserted;

the placement guide is configured to provide a placement depth of the implant of about 0.5 mm to about 4.5 mm, about 1 mm to about 4 mm, preferably about 1.5 mm to about 3 mm, beneath the outer surface of the skin of the patient;

the pilot-tube is configured to receive and guide the placement cannula into tissue; and at least one of the rigidity of the guide, the first distance, the second distance and the angle are configured to guide the placement cannula and deliver the implant at the determined placement depth.

The placement guide is generally configured to allow substantially free rotation of the cannula within the pilot-hole/pilot-tube of the placement guide. During an implant placement procedure, this feature permits the practitioner to conveniently, safely, and accurately create a placement tract through tissue by nimbly rotating the cannula through the tissue, without, or with minimal inhibition from the guide. It was discovered that placements of implants using systems with the described placement guides occurred with minimal or no harm, and with minimal or no bruising, to patients.

Such harm and bruising to patients may otherwise occur during placements of implants made, for example, with more cumbersome placement tools, such as a "one-piece placement tool," having a fixed guide portion, and a cannula that cannot freely rotate relative to the fixed guide. Placements of implants with such cumbersome one-piece placement tools, having a fixed guide portion, and a cannula that cannot freely rotate relative to the fixed guide, proceed with restricted motion of the cannula, due to the fixed nature of the tool. Restricted motion of the cannula, during an insertion procedure, can result in excessive or misdirected force being used to create a placement tract through tissue which may result in harm and/or bruising to the patient.

By contrast, the presently described systems have a placement guide configured to permit substantially free rotation of the cannula within the pilot-hole/pilot-tube of the placement guide which permits rotation of the cannula independently from the guide and, thus, relatively nimble maneuvering of the placement tool/system. During insertion of the cannula into an incision, prior to release of the implant from the cannula, the handle portion and cannula can be rotated by a practitioner, in clockwise and counterclockwise directions, e.g., back and forth within a span or range between about 9 o'clock to about 3 o'clock, about 10 o'clock and about 2 o'clock, or about 11 o'clock to about 1 o'clock relative to the central longitudinal axis of the pilot-tube on the placement guide. Rotation of a cannula in the presently described placement tool occurs independently of the placement guide, which remains substantially still on the outer surface of skin at the incision site and thus does not pull tissue at the incision site back and forth. Free rotation of the cannula in the presently described placement tool, within the pilot tube of the placement guide, permits the practitioner to gradually ease the cannula through tissue, even fibrous connective tissue, with optimal control of the cannula's insertion path. Thus, the presently described placement tool and placement guide allow for convenient, safe and accurate placement of the cannula into tissue. The presently described placement tool and placement guide also mitigate difficulties encountered upon insertions of implants into different types of tissue among patients.

In some embodiments, an implant removal tool is provided which includes a first arm, a second arm configured at least during use to be spaced apart from, and substantially parallel to, the first arm, a first opening arranged at a distal end of the first arm, and a second opening arranged at a distal end of the second arm. As used herein, the term "substantially parallel" with respect to first and second arms means that the first and second arms need not be perfectly parallel; rather, the first and second arms may be oriented substantially parallel to one another, for example, when the device is in an open orientation, prior to use, causing the first and second openings to generally point away from one another. Alternatively, the first and second arms are also oriented substantially parallel to one another when the device is in a closed orientation, during use when the arms are brought together, causing the first and second openings to generally point towards one another.

The first opening is configured to corral or otherwise capture a first end of an implanted implant, and the second opening is configured to corral or otherwise capture a second end of the implanted implant. The tool may also include a locking device configured to maintain the distance between the first arm and second arm as the arms are brought together and reach the user's desired spacing. The locking device permits the user/practitioner to carry out subsequent steps (e.g., incision and/or removal of the implant from the incision) hands-free with respect to the removal tool. In some embodiments, an implant removal tool is provided for removing an implant from intraepidermal, subepidermal, intradermal, subdermal, intracutaneous, and/or subcutaneous tissue.

In some embodiments the implant removal tool may include one and/or another of the following features:
- a connecting structure to connect the first and second arms;
- any locking device such as, e.g., one that comprises a ratchet mechanism or a sliding frictional locking mechanism (in some embodiments, the locking device may comprise the connecting structure);
- the first opening and second opening are formed from stainless steel wire;
- the first opening and second opening can be any shape such as, e.g., a round, square or oval shape;
- the first opening is formed at a first end of a stainless steel wire and the second opening is formed at a second end of the stainless steel wire;
- the wire either comprises the first arm and the second arm or is attached thereto;
- the connecting structure comprises a spring, coiled wire, or the like;
- a handle comprising a first grip attached to the first arm and a second grip attached to the second arm, and
- a connector piece situated along the stainless steel wire between the first arm and the second arm.

In some embodiments, a method is provided for removing an implant and includes providing a removal tool (e.g., according to disclosed embodiments). In some embodiments, the method further comprises at least one of: arranging the first arm of the removal tool at the outer surface of skin of a patient near a first end of an implant and corralling or otherwise capturing the first end of the implant, and nearby skin, within the first opening, and arranging the second arm of the removal tool at the outer surface of skin of the patient near the second end of the implant and corralling or otherwise capturing the second end of the implant, and nearby skin, with the second opening. The arranging of the first and second arms of the removal tool at the first and second ends of the implant may be done simultaneously (preferably) or sequentially. In some embodiments, each end is configured to perform the same function and is identical or substantially identical. The method also includes squeezing or otherwise forcing the first arm and the second arm together towards a first position, where when the first arm and the second arm are in the first position, the implant creates a tent in the skin at or around at least one end of the implant, and preferably both ends. The locking device may be engaged to permit the user/practitioner to carry out subsequent steps (e.g., incision and/or removal of the implant from the incision) hands-free with respect to the removal tool.

Thereafter, an incision in the skin of the patient may be made in or near the tent in the skin at or around either end. Upon the incision being made, the end of the implant near the incision can project out of the skin where it can be grabbed by forceps and/or the like. In some embodiments, the arm of the removal tool at the end of the implant opposite from where the incision was made will cause, while in the first position, at least the end of the implant to be pushed out of the incision. In other embodiments, further squeezing of the first arm and the second arm together towards a second position causes at least the end of implant to be pushed out of the incision. See, e.g., FIG. 13. In some embodiments, a method is provided for removing an implant from intraepidermal, subepidermal, intradermal, subdermal, intracutaneous, and/or subcutaneous tissue.

In some embodiments, such methods may further include one and/or another of the following features:
- the first position is a wider configuration of the first and second arms than the second position;
- the locking device holds the first arm and the second arm in the first position while the incision is created;
- the squeezing of the first arm and the second arm to reach the second position begins at the first position and ends at the second position, and
- the locking device holds the first arm and the second arm in the second position.

In some embodiments, a kit for placing an implant is provided and comprises a sterile (e.g., via gamma radiation) implant and sterile implant placement system, as described herein, for placing the implant. In some embodiments, the kit may further include instructions for use. In some embodiments, the sterile implant is contained in the kit in a sealed glass vial. In some embodiments, the sterile implant placement system includes a sterile placement guide and sterile placement tool as described herein. In some embodiments, each item in the kit is intended for single-use only. In some embodiments, the sterile implant includes a unique reference number that has been assigned to a patient. In some embodiments, a kit is provided for placing an implant into or among intraepidermal, subepidermal, intradermal, subdermal, intracutaneous, and/or subcutaneous tissue.

In some embodiments, the kit may further include, in one or more packages, one and/or another of the following sterile items:
- scalpel, hemostat, gauze, strips such as Steri-Strips™, liquid skin adhesive, bandages, syringe, needles, drapes (fenestrated and non-fenestrated), sterile gloves, an antiseptic agent such alcohol prep pads, an anesthetic agent such as lidocaine, a ruler, swabs, visual reference guide, and a writing instrument, such as a permanent marker.

In some embodiments, the sterile nature of the kit, and its contents, minimize risk of infection and permit a practitioner to conveniently arrange a sterile field (i.e., area) from which the implant may safely and properly be placed (i.e., inserted) into the patient.

These and other embodiments, objects, advantages, and features will become even more clear with reference to attached drawings and detailed description.

BRIEF DESCRIPTION OF SOME OF THE EMBODIMENTS

FIGS. 1A and 1B are illustrations depicting an exploded view of structures of an implant placement system according to some embodiments.

FIG. 10A is an illustration of an implant removal tool, with arms in an open orientation, according to some embodiments.

FIG. 10B is an illustration of an implant removal tool and sliding frictional locking mechanism, with arms in an open orientation, according to some embodiments.

FIG. 10C is an illustration of an implant removal tool and sliding frictional locking mechanism, with arms in a closed orientation, according to some embodiments.

Figure 11A:
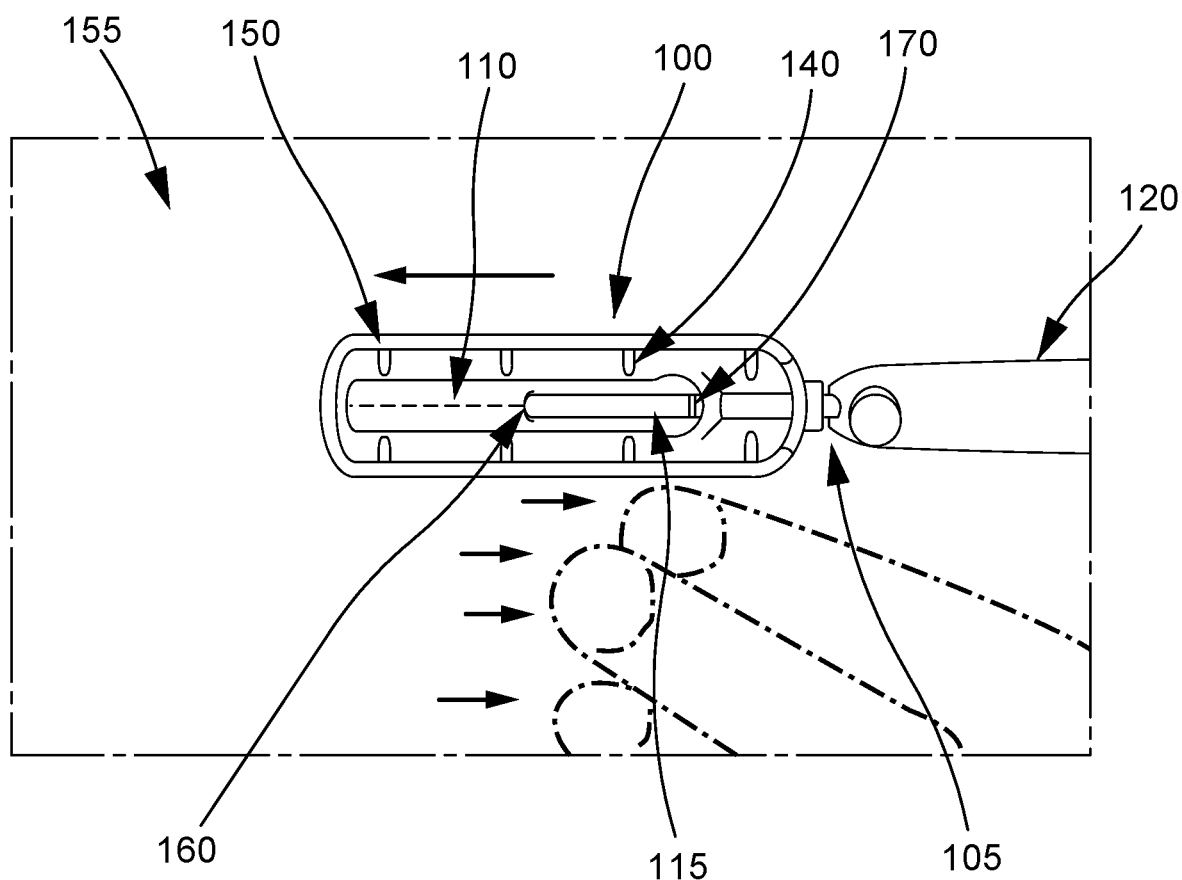
FIG. 11A is an illustration, according to some embodiments, depicting placement of the placement tool cannula into an insertion point in the surface of a patient's skin.
Figure 11B:
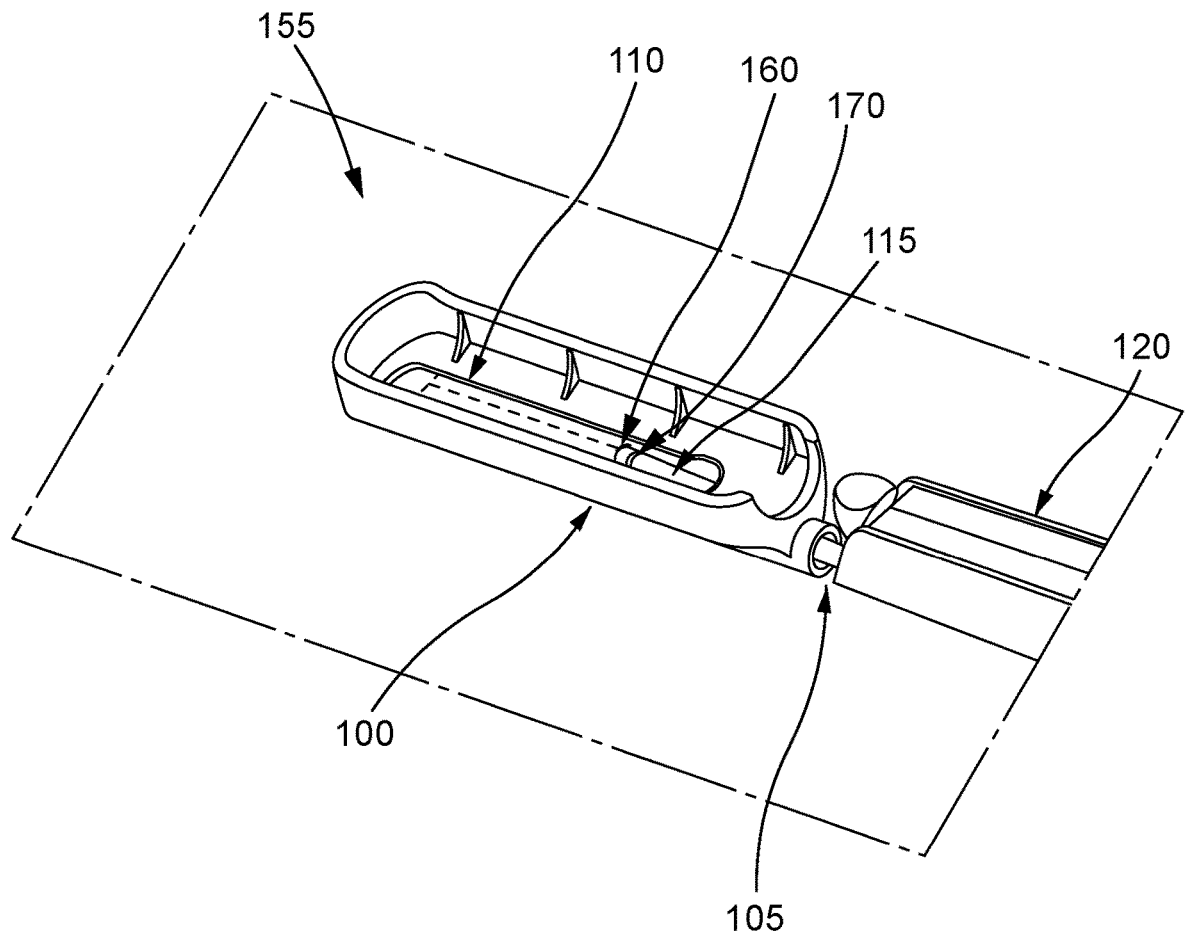

FIG. 11B is an illustration, according to some embodiments, depicting further placement of the cannula and implant beneath an outer surface of the patient's skin, until an indicator band on the placement tool cannula reaches the insertion point which signifies that the implant is properly located, and the implant is ready for release from the cannula into tissue at a determined placement depth, after which the cannula may be removed from the incision.

Figure 12A:
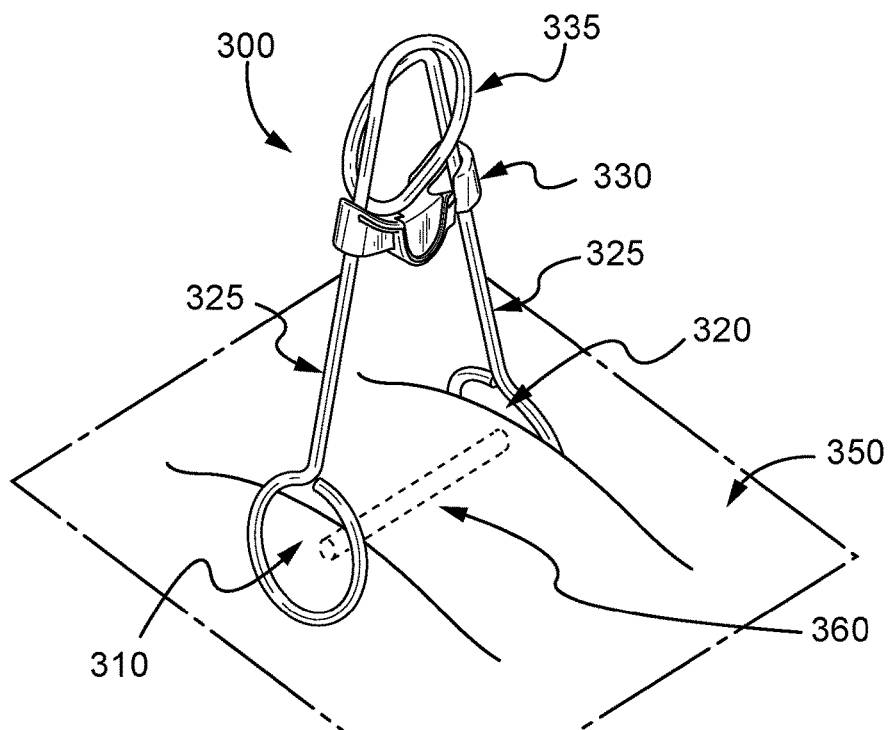

FIG. 12A is an illustration, according to some embodiments, depicting initial stages of "tenting" of both (i.e., proximal and distal) ends of the implant, and nearby skin, with arms of the removal tool.

Figure 12B:
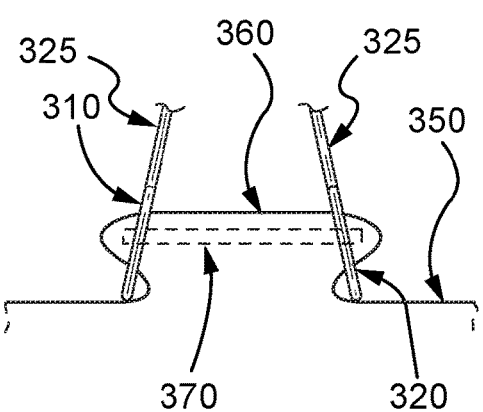

FIG. 12B is an illustration, according to some embodiments, of a side view of two tents being formed around both ends of an implant.

Figure 13:
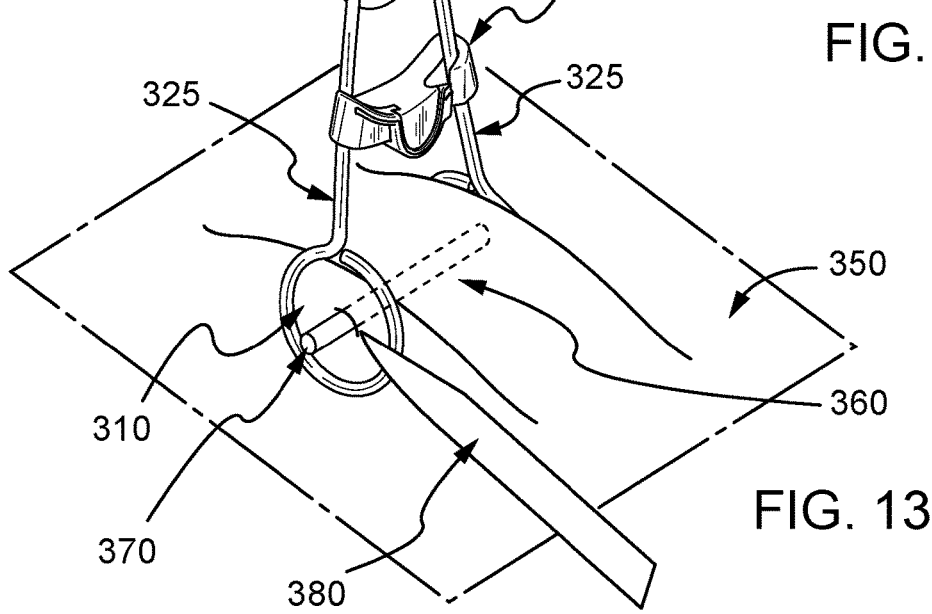

FIG. 13 is an illustration, according to some embodiments, depicting in implant emerging from an incision made at one tented end following tenting of both (i.e., proximal and distal) ends of the implant, and nearby skin, with arms of the removal tool. The incision can be made "hands-free" with respect to the removal tool in a relatively closed position or orientation.

Figure 14:
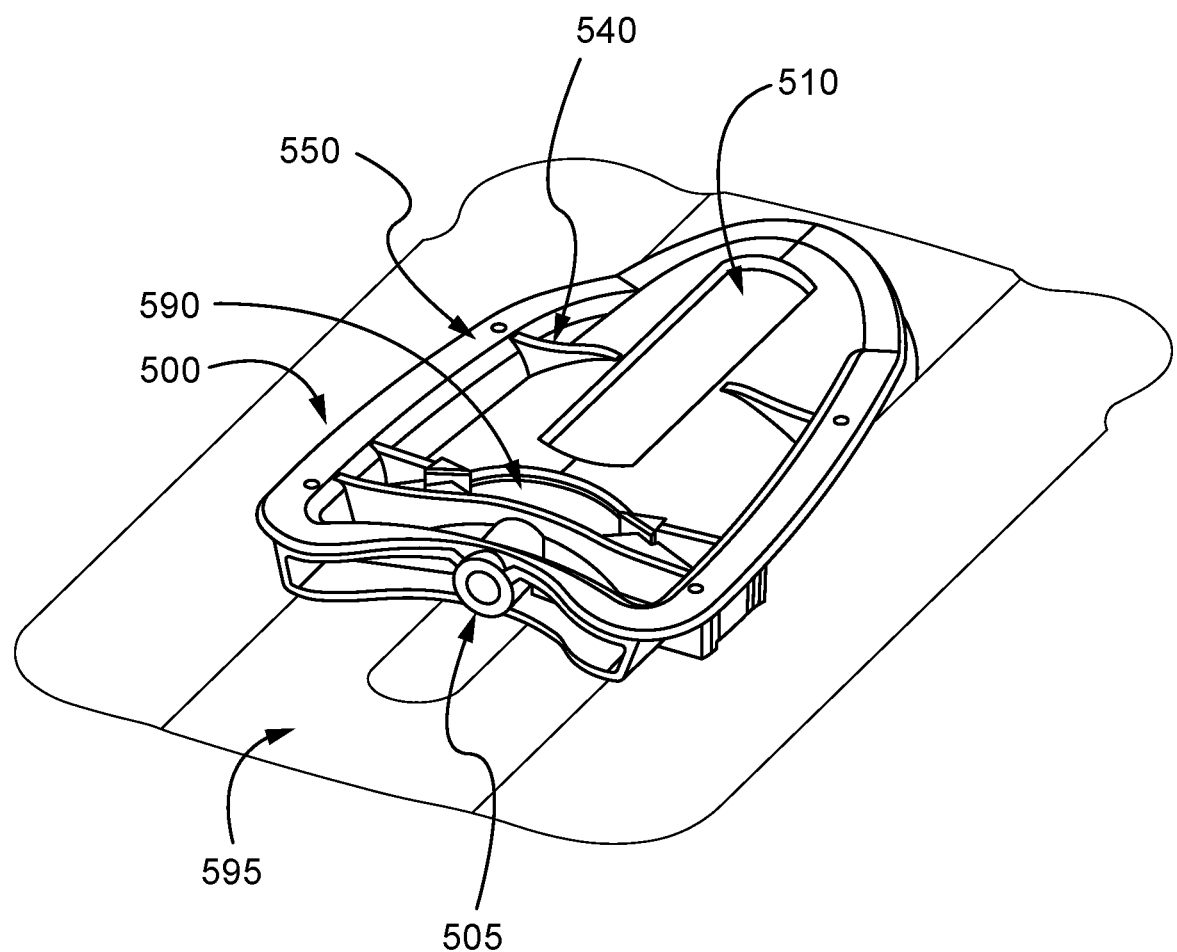

FIG. 14 is an illustration, according to some embodiments, of a placement guide as shown and described.

Figure 15:
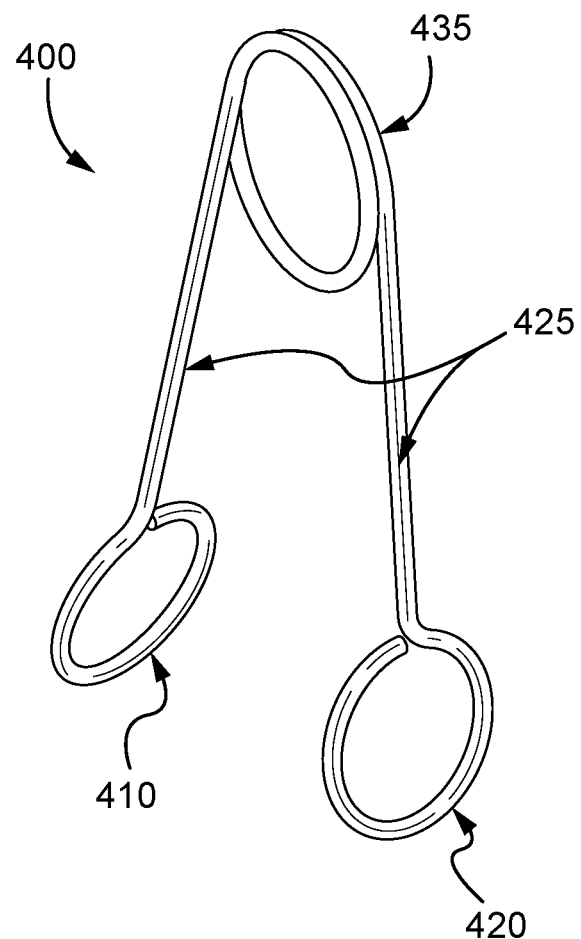

FIG. 15 is an illustration depicting an additional implant removal tool according to some embodiments.

DESCRIPTION OF SOME OF THE EMBODIMENTS

Some embodiments of the present disclosure present an implant placement system, which includes a placement guide configured to aid in the placement (i.e., also referred to herein alternatively as delivery or implantation) of an implant, which may be a cylindrical or columnar shaped implant (e.g., an osmotic pump), at a determined depth of about 0.5 mm to about 4.5 mm, about 1 mm to about 4 mm, about 1.5 mm to about 3 mm, beneath an outer surface of skin of a patient (for example, in the abdominal area).

Typically, the implant is placed (i.e., implanted) beneath an outer surface of skin of a patient to provide subcutaneous administration of a drug. The implant can be placed at a determined depth into almost any location, beneath an outer surface of skin, including at either or both legs, either or both arms (e.g., in the inside, outside, or back of the upper arm), or the back or abdomen. In some embodiments, the implant may be placed in the abdominal area within abdominal tissue, beneath an outer surface of skin, in the area extending below the ribs and above the belt line. To provide a number of locations for placement of one or more osmotic delivery device within the abdomen, the abdominal wall can be divided into four quadrants as follows: the upper right quadrant extending about 5-8 centimeters below the right ribs and about 5-8 centimeters to the right of the midline, the lower right quadrant extending about 5-8 centimeters above the belt line and about 5-8 centimeters to the right of the midline, the upper left quadrant extending about 5-8 centimeters below the left ribs and about 5-8 centimeters to the left of the midline, and the lower left quadrant extending about 5-8 centimeters above the belt line and about 5-8 centimeters to the left of the midline. This provides multiple available locations for implantation of one or more devices on one or more occasions. Placement and removal of the implant are generally carried out by medical professionals using local anesthesia (such as, e.g., lidocaine).

In some embodiments, the determined depth at which the implant is placed is described as a mean depth below a surface of skin where the mean depth can be calculated from measured depths (e.g., via ultrasound techniques) of both ends (i.e., proximal and distal) of the inserted implant. The presently disclosed placement systems, methods and devices, including those that include the presently disclosed placement guides, are adaptable to provide an implant to virtually any "determined depth" beneath an outer surface of skin of a patient. In some embodiments, disclosed placement system is configured to deliver an implant to any particular depth beneath an outer surface of skin. In some embodiments, the determined depth is less than about 5 mm beneath an outer surface of skin. In some embodiments, the determined depth is about 0.5 mm to about 4.5 mm beneath an outer surface of skin of a patient. In some embodiments, the determined depth is about 1 mm to about 4 mm beneath an outer surface of skin of a patient. In some embodiments, the determined depth is about 1.5 mm to about 3 mm beneath an outer surface of skin of the patient.

In some embodiments, the implant is an osmotic pump comprising a metal exterior (e.g., titanium or a titanium alloy). In some embodiments, the implant is an osmotic pump comprising an insulinotrophic peptide (e.g., synthetic exenatide, exendin-4). In some embodiments, the insulinotrophic peptide is exendin-4. In some embodiments, the insulinotrophic peptide is exenatide. In some embodiments, the insulinotrophic peptide is formulated with stabilizers. In some embodiments, the stabilizers comprise or consist of carbohydrate (e.g., sucrose), antioxidant (e.g., methionine), and buffer (e.g., sodium citrate/citric acid). The implant may comprise any one or more of a plurality of other treatments, drugs, and/or the like.

In some embodiments, the implant is an osmotic pump that provides a sustained (e.g., continuous) in vitro release rate of an insulinotrophic peptide (e.g., synthetic exenatide, exendin-4) of about 20 mcg/day for at least about 3 months, about 40 mcg/day for at least about 6 months, or about 60 mcg/day for at least about 6 months, or an in vitro release rate of about 20 mcg/day to about 60 mcg/day for at least about 3 months to at least about 6 months.

The term "continuous delivery," as used herein, may refer to a substantially continuous release of drug from an osmotic delivery device and into tissues near the implantation site, e.g., intraepidermal, subepidermal, intradermal, subdermal, intracutaneous, and/or subcutaneous tissues. For example, an osmotic delivery device may release one or more drugs essentially at a predetermined rate based on the principle of osmosis. Extracellular fluid enters the osmotic delivery device through the semi-permeable membrane directly into the osmotic engine that expands to drive the piston at a slow and consistent rate of travel. Movement of the piston forces the drug formulation to be released through the orifice of the diffusion moderator. Thus release of the drug from the osmotic delivery device is at a slow, controlled, consistent rate.

Continuous delivery of exenatide or exendin-4 using an implantable osmotic delivery device may provide the following benefits for subjects in need of treatment: treating type 2 diabetes mellitus, improving glycemic control (as measured, e.g., by glucose levels, HbAlc, and/or fructosamine), reducing HbAlc, reducing fasting plasma glucose, reducing post-prandial blood glucose levels, reducing adverse gastrointestinal events (e.g., nausea and vomiting) relative to periodic, (e.g., twice-daily), injections, weight loss, reducing LDL-C, reducing systolic blood pressure, treating hypertension, reducing fructosamine levels, improving of quality of life for subjects undergoing treatment, etc. One or more other benefits may also be achieved.

In addition, the continuous delivery of an insulinotrophic peptide (e.g., exenatide, exendin-4) may be used in the practice of the following methods: treating obesity, controlling appetite, reducing caloric intake, reducing food intake, suppressing appetite, treating impaired glucose tolerance, treating post-prandial hyperglycemia, treating post-prandial dumping syndrome, treating hyperglycemic conditions, reducing triglycerides, reducing cholesterol, increasing urine flow, decreasing potassium concentration in the urine, alleviating toxic hypervolemia, inducing rapid diuresis, pre-surgical patient preparation, post-surgical patient treatment, increasing renal plasma flow and glomerular filtration rate, treating pre-eclampsia or eclampsia during pregnancy, increasing cardiac contractility, treating renal failure, treating congestive heart failure, treating nephrotic syndrome, treating pulmonary edema, treating systemic edema, treating cirrhosis, treating impaired glucose tolerance, treating pre-diabetes (blood glucose levels that are higher than normal but not yet high enough to be diagnosed as diabetes), treating type 1 diabetes mellitus (e.g., in combination with insulin), reducing risk of a cardiovascular event due to impaired glucose tolerance, reducing risk of a cerebrovascular event due to impaired glucose tolerance, delaying the progression of diabetes, ameliorating diabetes, delaying diabetes onset, inducing β-cell preservation and restoring β-cell functionality, restoring normoglycemia, providing euglycemic control, treating peripheral vascular disease, treating acute coronary syndrome, treating cardiomyopathy, treating gestational diabetes, treating polycystic ovary syndrome, treating or preventing nephropathy, and treating diabetes induced by a variety of diseases or conditions (for example, steroid induced diabetes, human immunodeficiency virus treatment-induced diabetes, latent autoimmune diabetes in adults, nonalcoholic steatohepatitis, nonalcoholic fatty liver disease, hypoglycemia unawareness, restrictive lung disease, chronic obstructive pulmonary disease, cardiovascular diseases, e.g., heart failure, atherosclerosis, and acute coronary syndrome, lipoatrophy, metabolic syndrome, treating Alzheimer's disease), etc.

The implant may be any type of implant intended for insertion beneath the surface of the skin. In some embodiments, the implant is a cylindrical or columnar shaped implant. In some embodiments, the implant is other than an osmotic pump. For example, in some embodiments, the implant is a diffusion-controlled implant. The diffusion-controlled implant may include, for example, a polymer matrix core having a solid dosage form of an active substance that diffuses from the implant to provide a substantially constant dosage of the active substance. The diffusion-controlled implant may include, for example, a substantially or completely non-porous polymer matrix such as a thermoplastic, from which the active substance diffuses.

In some embodiments, the diffusion-controlled implant is a cylindrical or columnar shaped implant. In some embodiments, the diffusion-controlled implant contains a contraceptive as the active substance. In some embodiments, the diffusion-controlled implant contains an active substance, for use in treating opioid addiction, Parkinson's disease, hypothyroidism, and/or the like.

The implant may be of any suitable size for insertion into a patient, particularly a human patient. The size of the implant may range, for example, from about 1 mm to about 6 mm wide (e.g., diameter) and about 10 mm to about 60 mm long. In some embodiments, the implant may have a width of about 1 mm to about 2 mm, about 2 mm to about 3 mm, about 3 mm to about 4 mm, or about 5 mm to about 6 mm. In some embodiments, the implant has a length of about 10 mm to about 20 mm, about 20 mm to about 30 mm, 30 mm to 40 mm, about 40 mm to about 50 mm, about 50 mm to about 60 mm. In some embodiments, the implant is about 4 mm in diameter (i.e., wide) and about 44 mm long. Systems, methods and devices herein can be adapted for placement of any implant having any shape, including a substantially cylindrical or columnar shaped implant, or having a shape that is amenable to tenting under the skin with a removal tool. Any device/implant suitably sized for implantation/removal can be used.

In one aspect, a system is provided for placing an implant, comprising: a placement tool comprising a handle portion, and a placement cannula movable within or adjacent, and relative to, the handle portion, the cannula having a length, a proximal end arranged near the handle portion and a distal end opposite the proximal end, the placement cannula configured to deliver the implant within a tissue of a patient via an incision in the skin of a patient at an implantation site; and a placement guide having a first surface and pilot-tube, wherein the tube includes a proximal end configured to receive the distal end of the placement cannula; a distal end spaced apart from the proximal end at a first distance; a longitudinal central axis arranged relative to the first surface at either or both of a second distance and an angle; and the placement guide is configured to guide the placement cannula within the tissue to effect implantation of the implant at a determined placement depth beneath the outer surface of the skin of the patient.

In some embodiments of the system, at least one of the first distance, the second distance and the angle are configured to guide the placement cannula and deliver the implant at the determined placement depth. In some embodiments of the system, the determined placement depth is about 0.5 mm to about 4.5 mm beneath the outer surface of the skin of the patient. In some embodiments of the system, the placement guide further comprises a visualization window or opening, wherein the visualization window or opening extends along a length and a width of the placement guide and is configured to allow visual observation and/or palpation of an area of an outer surface of skin around the implantation site.

In some embodiments of the system, the placement guide further comprises a visualization opening, wherein the visualization opening extends along a length and a width of the placement guide and is configured to allow visual observation and palpitation of an area of an outer surface of skin around the implantation site. In some embodiments of the system, the implant is an osmotic mini-pump. In some embodiments, the system is configured to permit the placement cannula to rotate within the pilot-tube.

In another aspect, a method is provided for placing an implant, comprising: providing a placement system described herein. In some embodiments, the method further comprises at least one of: loading the implant into the distal end of the placement cannula; creating an incision in the skin at an implantation site; arranging the placement guide at the implantation site, such that the distal end of the pilot-tube is aligned with the incision; inserting the distal end of the loaded placement cannula in the proximal end of the pilot-tube; moving the placement cannula relative to the pilot-tube until at least a part of the handle portion is proximate the proximal end of the pilot-tube such that the distal end of the placement cannula is guided farther into the incision and into the tissue beneath and/or adjacent the incision; releasing the implant from the placement cannula; removing the placement cannula from the skin of the patient; and removing of the placement guide from the skin of the patient.

In some embodiments of the method for placing an implant, the placement cannula is guided into the incision and into the tissue with rotation of the handle portion and placement cannula within the pilot-tube. In some embodiments, prior to creating the incision, the method further comprises: cleaning the skin at the implantation site; marking the skin for making the incision; and injecting a local anesthetic in a vicinity of the mark.

In some embodiments of the method for placing an implant, after release and/or removal of the placement cannula, and/or removal of the placement guide, the method further comprises at least one of: cleaning the incision; applying pressure to the incision; applying an adhesive to at least one side of the incision; and closing the incision. In some embodiments of the method, the implant is released from the placement cannula at the determined depth. In some embodiments of the method, the determined depth is between about 0.5 mm to about 4.5 mm beneath the outer surface of the skin of the patient. In some embodiments of the method, both ends of the implant are placed at a determined depth that is substantially the same. In some embodiments of the method, both ends of the implant are placed at a determined depth that is within about 0.3 mm of one another.

In another aspect, a placement guide device is provided for use with a placement tool, the guide comprising: a first surface; and a pilot-tube having a central longitudinal axis, wherein the tube includes a proximal end configured to receive the distal end of a placement cannula for delivering an implant to tissue; a distal end spaced apart from the proximal end at a first distance; the longitudinal axis arranged relative to the first surface at either or both of a second distance and an angle; and the placement guide is configured to guide a placement cannula of a placement tool within the tissue to effect implantation of the implant at a determined placement depth beneath the outer surface of the skin of the patient.

In some embodiments, the placement guide is configured to permit rotation of the placement cannula within the pilot-tube. In some embodiments, the placement guide further comprises a visualization window or opening that extends along a length and a width of the first surface and configured to enable visual observation and/or palpation of an area of the outer surface of skin around the site at which the implant is being inserted. In some embodiments, the visualization window or opening has a length that extends beyond the tip of the cannula when the cannula is inserted into, and fully extended through, the pilot-tube. In some embodiments, the placement depth is from about 0.5 mm to about 4.5 mm beneath the outer surface of the skin of the patient. In some embodiments, the pilot-tube is configured to receive and guide the placement cannula into tissue. In some embodiments, the placement guide is made from a material that is translucent or substantially clear. In some embodiments, the pilot-tube is configured at an incline relative to the underside of the guide. In some embodiments, the placement guide cannot readily be flexed or bent, lengthwise or width-wise, by a user.

In another aspect, an implant removal tool is provided comprising: a first arm; a second arm configured at least during use to be spaced apart from and substantially parallel to the first arm; a first opening arranged at a distal end of the first arm; a second opening arranged at a distal end of the second arm; wherein: the first opening is configured to corral a first end of a positioned implant; the second opening is configured to corral a second end of the positioned implant; and a locking device is configured to maintain the distance between the first arm and second arm as the arms are brought together.

In some embodiments, the implant removal tool further comprises a connecting structure to connect the first and second arms. In some embodiments, the locking device comprises a ratchet mechanism. In some embodiments, the locking device comprises a frictional locking mechanism. In some embodiments, the first opening and second opening are formed from stainless steel wire. In some embodiments, the first opening and second opening are generally round, oval or square shaped. In some embodiments, the first opening is formed at a first end of a stainless steel wire and the second opening is formed at a second end of the stainless steel wire. In some embodiments, the wire either comprises the first arm and the second arm or are attached thereto. In some embodiments, the connecting structure comprises a spring or coil. In some embodiments, the implant removal tool further comprises a handle, wherein the handle comprises: a first grip attached to the first arm; a second grip attached to the second arm; and a connector piece situated along the stainless steel wire between the first arm and the second arm. In some embodiments, the first and second arms, the first and second ends, and the connecting structure are made from one or more lengths of wire. In some embodiments, the first and second arms, the first and second ends, and the connecting structure are made from a single length of wire.

In another aspect, a method is provided for removing an implant, comprising: providing a removal tool as described herein. In some embodiments, the method further comprises at least one of: arranging the first arm at a first end of an implant, wherein the implant is under an outer surface of skin of a patient; corralling the first end of the implant and nearby skin within the first opening; locating a second end of the implant; corralling the second end of the implant and nearby skin within the second opening; squeezing or otherwise forcing the first arm and the second arm together towards a first position, wherein when the first arm and the second arm are in the first position, the implant creates a tent in the skin that includes the first and/or second end of the implant; creating an incision in the skin of the patient near the tent in the skin at the first or second end of the implant; and squeezing the first arm and the second arm together towards a second position, wherein when the first arm and second arm are in the second position, the second end of the implant exits the skin of the patient through the incision.

In some embodiments of the method for removing an implant, the first and second ends of the implant are located within the first and second openings. In some embodiments of the method, the first position is a wider configuration of the first and second arms than the second position. In some embodiments of the method, the locking device holds the first arm and the second arm in the first position while the incision is created. In some embodiments of the method, the squeezing of the first arm and the second arm to reach the second position begins at the first position and ends at the second position. In some embodiments of the method, the locking device holds the first arm and the second arm in the first and second positions.

In some embodiments, the placement guide interfaces with a placement tool, for example, along the cannula of the placement tool, to deliver the implant at a determined depth (e.g., into or among one or more of intraepidermal, subepidermal, intradermal, subdermal, intracutaneous, and/or subcutaneous tissue). The placement tool may include a cannula configured to house the implant for delivery. Some embodiments of the placement tool are described in U.S. Pat. No. 6,190,350, the entire contents of which are hereby incorporated by reference. The design of the placement guide, according to some embodiments, may be configured to direct the cannula, and thereby deliver the implant, at a particular/determined depth beneath an outer surface of skin. FIG. 1A shows an exemplary configuration of an embodiment of the implant placement system including a placement tool 120 and placement guide 100 in an exploded view. The placement tool 120 includes a handle portion 121 having right and left handle sections 120a and 120b and a placement cannula 115. FIG. 1B illustrates an exploded view that also shows internal components of the placement tool 120 which provide functionality for (at least) dispensing an implant at a determined depth beneath the outer surface of skin (e.g., into or among intraepidermal, subepidermal, intradermal, subdermal, intracutaneous, and/or subcutaneous tissue.) See U.S. Pat. No. 6,190,350.

The placement guide 100 may comprise a relatively rigid material which may be made from plastic or metal (e.g., aluminum or an aluminum alloy). The placement guide 100 may include, according to some embodiments, some or all of the following features: a first surface which during use is placed adjacent the skin, a pilot-tube 105 located on one end (proximal end) of the guide 100 for receiving the placement tool cannula 115, and a visualization opening 110. It was discovered that relatively rigid, rather than flexible guides 100, best govern and restrict insertion of the cannula and placement of the implant to a determined depth beneath an outer surface of skin. For example, in some embodiments, the placement guide is sufficiently rigid that it cannot be substantially flexed, warped or bent, length-wise and/or width-wise, by a user during normal usage (e.g., during an insertion procedure).

On the other hand, relatively flexible or pliant guides made, for example, from relatively thin plastic, tend to flex during the insertion procedure and permit the cannula to drift deeper than desired beneath the outer surface of skin, resulting in uncontrolled and overly deep placement of the implant (e.g., greater than 5 mm beneath the outer surface of skin).

Figure 5A:
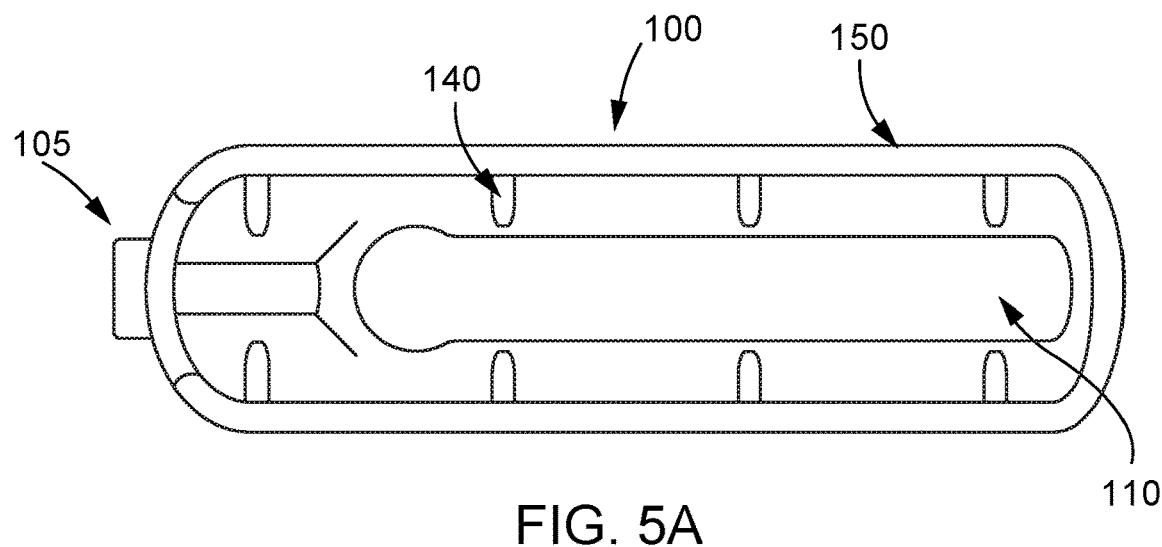
FIGS. 5A, 5B, 5C, 5D and 5E are illustrations depicting various views of structures of an implant placement guide according to some embodiments.

Thus, in some embodiments, placement guide 100 is configured to enhance rigidity. For example, rigid plastic and or metal materials for placement guide 100 are preferred. Additionally, in other embodiments, guide 100 has raised sides 150 (e.g., 5-30 mm tall) and/or one or more reinforcing gussets (i.e., reinforcing ribs) 140 that confer stability and rigidity to guide 100. In some embodiments, guide 100 comprises one or more reinforcing gussets 140, running perpendicular to pilot-tube 105 and/or running perpendicular to the length of visualization opening 110, to add and/or reinforce rigidity to guide 100. See, e.g., Example 1. Guide 100 may comprise, for example, one gusset, two gussets, four gussets, six gussets, eight gussets, ten gussets, twelve gussets, etc. Multiple gussets are generally evenly spaced along the length of guide 100, as illustrated by the eight gussets shown in the guide of FIG. 5A. Gussets 140 may be situated along the entire width of the guide (such as some of those shown, closest to the pilot-tube, in the guide of FIG. 14). In some embodiments, each gusset 140 does not span the entire width of the guide, as shown in the guide of FIG. 5A.

Pilot-tube 105 includes a proximal opening near the proximal end of guide 100, and a distal opening spaced apart from the proximal opening. Tube 105 is substantially straight, and includes a longitudinal central axis. The placement guide 100 may be any color, white or, in some embodiments, translucent or substantially clear, to enhance visualization of the implant procedure. In some embodiments, the placement guide is made from material(s) (e.g., medical-grade plastic) that is/are translucent or substantially clear.

Pilot-tube 105 receives placement tool cannula 115, such that placement tool cannula 115 can freely rotate within pilot-tube 105. During insertion of placement tool cannula 115 beneath the skin of the patient, the handle portion 121 of placement tool 120 and, thus, placement tool cannula 115 can be rotated by the practitioner, in clockwise and counterclockwise directions, e.g., back and forth within a span or range between about 9 o'clock to about 3 o'clock, between about 10 o'clock and about 2 o'clock, or between about 11 o'clock to about 1 o'clock, relative to the central longitudinal axis of the pilot-tube on placement guide 100, while placement guide 100 remains substantially stationary on the outer surface of skin of the patient. In some embodiments, the rotation may be between about 10 o'clock and about 2 o'clock. Rotation of the handle portion 121 of placement tool 120 and placement tool cannula 115, while placement guide 100 remains substantially stationary on the outer surface of the skin, can be used to ensure controlled placement of an implant at a determined depth that is about 0.5 mm to about 4.5 mm, about 1 mm to about 4 mm, and in some embodiments, about 1.5 mm to about 3 mm beneath the surface of skin of the patient. In some embodiments, the determined depth at which the implant is placed is a depth into or among intraepidermal, subepidermal, intradermal, subdermal, intracutaneous, and/or subcutaneous tissue.

In some embodiments, placement guide 100 is configured to be long enough for the visualization opening 110 to extend at least past the tip of the placement cannula 115, when fully extended, through the pilot-tube beneath the guide. A guide and visualization opening of such length causes the guide to overhang the sharp tip of the fully extended cannula and thus provides some protection from the sharp tip. Further, in some embodiments, placement guide 100 is configured for the visualization opening 110 to be long enough, past the tip of a fully extended placement cannula, to allow the practitioner see and/or touch, through visualization opening 110, skin above the entire inserted length of the cannula, to confirm proper placement of the cannula/implant to a determined placement depth (e.g., less than about 5 mm from the outer surface of skin). In some embodiments, placement guide 100 has a length of about 60 mm to about 120 mm. In some embodiments, placement guide 100 has a length of about 80 mm to about 100 mm. In some embodiments, placement guide 100 has a length of about 90 mm.

Insertion of the implant proceeds particularly smoothly when the practitioner uses one hand, for example, the "dominant" hand, to grip the handle portion 121 of placement tool 120, to drive cannula 115 into an incision, and simultaneously uses their remaining hand, the "non-dominant" hand, to apply reverse traction directly to points on the patient's skin as close as possible to advancing cannula 115 on either side of, or on both sides of, the guide. During such preferred methods, insertion of the cannula and placement of the implant proceed substantially hands-free with respect to the placement guide. See FIG. 11A. Thus, the practitioner may place his or her hand on both or either side of the guide 100, without touching or without substantially touching the guide 100, applying pressure in a direction that is opposite (or substantially opposite) of the direction that the cannula 115 is being inserted into the patient. Applying reverse traction in this way, without substantially gripping placement guide 100, keeps the patient's skin tight, on either or both sides of the incision, while cannula 115 creates an insertion channel as it smoothly advances into tissue. Accordingly, in some embodiments, placement guide 100 is relatively narrow. For example, in some embodiments, the placement guide has a width of about 10 mm to about 80 mm. In some embodiments, the placement guide has a width of about 15 mm to about 35 mm. In some embodiments, the placement guide has a width of about 25 mm.

Figure 5B:
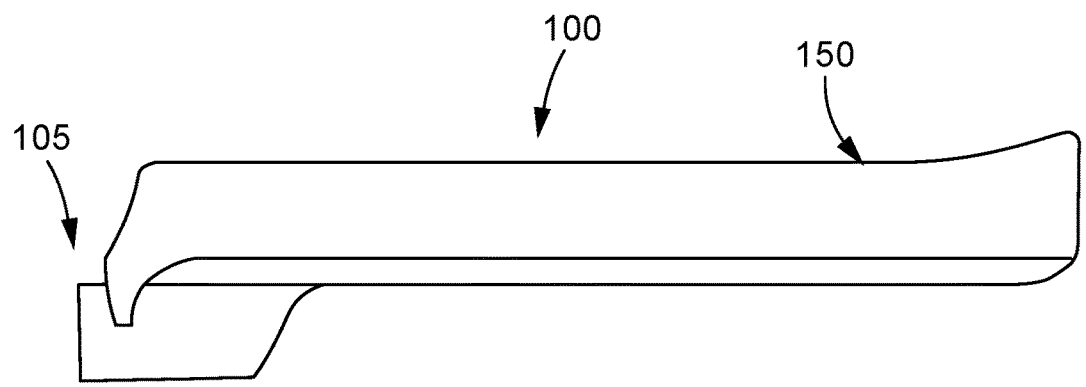
Figure 5C:
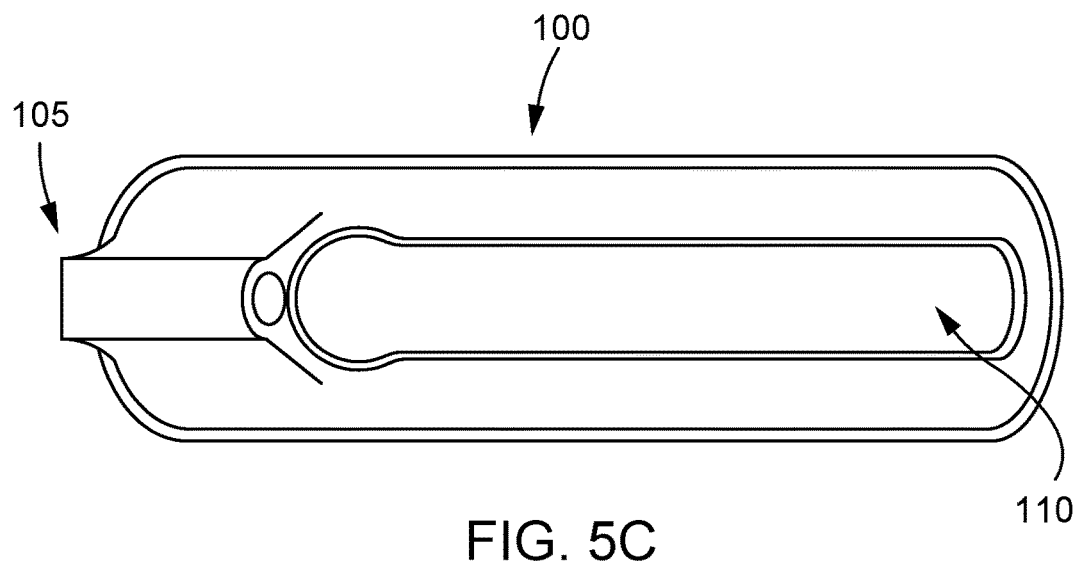
Figure 5D:
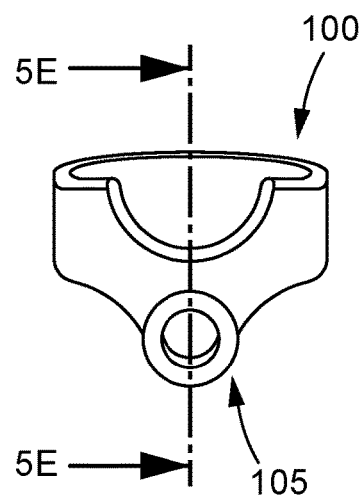
Figure 5E:
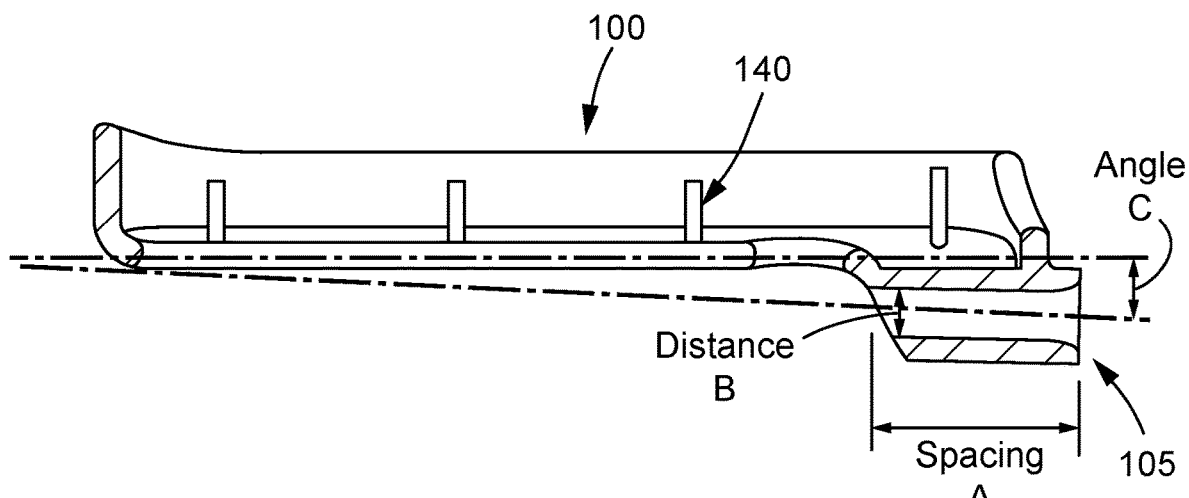

The determined depth of an implant may be controlled or otherwise determined by configuring at least one of: the rigidity of the guide, Spacing A of the proximal and distal ends of the pilot-tube 105 (and/or the placement guide 100 as a whole; see, e.g., FIG. 5E), Distance B, i.e., the longitudinal axis (or, in other words, the diameter of the pilot tube), is spaced from the first surface (i.e., the bottom surface that is placed adjacent to the skin; see, e.g., FIG. 5B, 5E), Angle C, the pilot-tube angle; and the longitudinal axis relative to at least one of the skin and the first surface (and/or the angle of the first surface relative to the skin; see, e.g., FIG. 5E). Distance B (i.e., the inner diameter of pilot-tube 105) is sized so that there is minimal spacing or play between the cannula 115 and pilot-tube 105. In some embodiments, the inner diameter of pilot-tube 105 includes one or more notches, splines, grooves spokes or flattened area(s) to make cannula 115 fit more snugly within the pilot-tube 105 and provide just enough friction against cannula 115 to inhibit cannula 115 from slipping too easily into/from pilot-tube 105.

Spacing A and Distance B are configured to make the placement cannula fit snugly within the pilot-tube. In some embodiments, Spacing A is from about 10 mm to about 30 mm. In some embodiments, Spacing A is from about 15 mm to about 20 mm. In some embodiments, Spacing A is about 18.5 mm. In some embodiments, Distance B is a diameter of from about 4 mm to about 10 mm. In some embodiments, Distance B is a diameter of from about 2 mm to about 8 mm. In some embodiments, Distance B is a diameter of about 3.8 mm.

In some embodiments, Angle C, the pilot-tube angle, is configured to cant the central longitudinal axis of the pilot-tube in a slightly upward direction relative to the substantially level underside of guide 100. As such, the proximal end of the pilot-tube is a greater distance from the underside of the guide than is the distal end of the pilot-tube from the underside of the guide. To illustrate, passage of a cannula through each pilot-tube at a slight incline, or upward cant, relative to the level plane of the underside of the guide, causes the tip of the cannula to move closer to the underside of the guide as it proceeds through and past the pilot-tube and towards the distal end of the placement guide. Placement guides may have pilot-tubes may be configured with Angle C at a slight incline relative to the underside of the guide, or the pilot-tubes may be configured with Angle C at a decline (i.e., negative), or even parallel (i.e., 0°), relative to the underside of the guide. In some embodiments, pilot-tubes configured with Angle C at a slight incline relative to the underside of the guide may be preferred. Placement guides having pilot-tubes configured with Angle C at a slight incline relative to the underside of the guide resulted in a shallow placement of implants to determined depths.

In some embodiments, Angle C is from about 0.25° to about 5.0°. In some embodiments, Angle C is from about 1.0° to about 3.0°. In some embodiments, Angle C is about 1.2°. In some embodiments, Angle C is about 1.17°±0.35°.

Thus, by configuring such parameters of the guide, one can target a determined depth and/or final location of an implant using placement guide 100. In some embodiments, the implant is placed just beneath the outer surface of skin (e.g., less than 5 mm) to ensure relatively easy identification and removal of the device when it is time to replace it.

For most patients, a distance of between about 1 mm and about 4 mm (and in some embodiments, between about 1.5 mm and about 3 mm) is an appropriate depth beneath the surface of the skin. To that end, one or more of the above-noted parameters can be adjusted so as to achieve one and/or another of these values, and/or a range of values between them. In some embodiments, a kit is provided that can include placement guides 100 having combinations of these parameters configured for specific depths.

In some embodiments, to insert an implant into a patient's tissue, beneath an outer surface of skin, at an implantation site, the following procedure may be used, using sterile techniques. Prior to making an incision (for the cannula 115 of the placement tool 120 to be received), a selected implantation site is cleaned with an alcohol solution (or the like, e.g., ChloraPrep®; chlorhexidine gluconate solution). The location of the incision may be marked and a local anesthetic applied or injected in the vicinity of the implantation site; thereafter, the incision is made. The incision location may be determined by placing placement guide 100 on the skin at the implantation site, and through the visualization opening 110, for example, the skin is marked at the distal end of pilot-tube 105. The visualization opening 110 may also be used to view and/or palpitate the implantation during placement. In some embodiments, visualization opening 110 is sufficiently long and wide for the practitioner to view and/or touch an entire outer surface of skin below which the cannula advances. In some embodiments, the visualization opening 110 has a length of about 50 mm to about 100 mm. In some embodiments, visualization opening 110 has a length of about 60 mm to about 80 mm. In some embodiments, visualization opening 110 has a length of about 62 mm. In some embodiments, visualization opening 110 has a width of about 5 mm to about 20 mm. In some embodiments, visualization opening 110 has a width of about 8 mm to about 15 mm. In some embodiments, visualization opening 110 has a width of about 10 mm.

In some embodiments, a scalpel, the sharp tip of a cannula, or the like can be used to make the incision and/or otherwise pierce the skin at the implantation site (with or without marking). In other embodiments, cannula 115 of placement tool 120 can be configured to make the incision and/or otherwise pierce the skin at the implantation site (with or without marking). In still other embodiments, a scalpel, the sharp tip of a cannula, or the like can be configured to work through pilot-tube 105 to pierce or otherwise make an incision into the skin. In some embodiments, the incision that is made is about 5 mm deep. Once the incision is made, the distal end of cannula 115 housing the implant is received in the proximal end of the pilot-tube 105 and then pushed through the pilot-tube 105, into the incision and beneath the outer surface of skin. As the practitioner grasps the handle portion 121 of placement tool 120, for example with their dominant hand, cannula 115 is continually pushed into pilot-tube 105, beneath an outer surface of skin, until the proximal end of cannula 115 which meets the handle portion 121 abuts (for example) a portion of the placement guide 100 and/or the pilot-tube 105. Alternatively, cannula 115 may include markings which indicate the distance cannula tube 115 must travel relative to at least one of pilot-tube 105, placement guide 100, visualization opening 110 and the incision. In some embodiments, cannula 115 is inserted by a practitioner by grasping the handle portion 121 of placement tool 120 with their dominant hand, and potentially rotating cannula 115 back and forth, within a span or range between about 9 o'clock to about 3 o'clock, between about 10 o'clock and about 2 o'clock, or between about 11 o'clock to about 1 o'clock, relative to the central longitudinal axis of the pilot-tube on placement guide 100. With the other non-dominant hand, the practitioner may apply counter-traction directly to the outer surface of skin on either side (or on both sides) of placement guide 100 (e.g., hands-free with respect to the placement guide or, in other words, without substantially grasping placement guide 100). By contrast, it was discovered that attempts to indirectly apply counter traction, by using the non-dominant hand to press directly onto the sides of a placement guide, and thus put indirect pressure, via the guide, onto the outer surface of skin beneath placement guide 100 proved to be less effective because the outer surface of skin around the incision rolled back and bunched up during the insertion procedure.

At any point during the insertion procedure, the practitioner may confirm proper placement of cannula 115, to a determined depth below an outer surface of skin, by palpitating the skin above cannula 115 through visualization opening 110 of placement guide 100. Placement tool 120 includes cannula 115 within which is a fixed pusher rod 125 for releasing the implant. Pusher rod 125 is longitudinally fixed within the handle while cannula 115 slides over pusher rod 125 to release the implant. Cannula 115 is moved over pusher rod 125 by a sliding actuator 130a/b mounted in a track of the handle. Following confirmation of proper placement of the cannula, actuation mechanism 130a/b of placement tool 120 can be operated to retract cannula 115 over the fixed pusher rod, causing the implant to pushed (i.e., dispensed) from the tip of cannula 115, and into the patient's tissue. In some embodiments, actuation mechanism 130a/b is locked in an extended position to prevent unintended release of the implant.

Subsequently, in some embodiments, at least a substantial portion of the cannula 115 is withdrawn from the tissue. In one embodiment, following dispensing of the implant, the tip of pusher 125 barely extends from the end of cannula 115, and is visible to the practitioner as confirmation that the implant was properly dispensed from cannula 115 and thus delivered into the tissue. During and/or after dispensing of the implant, the proper determined depth of the implant beneath the outer surface of the patient's skin can be confirmed by manual palpitation of the skin above the implant (see U.S. Pat. No. 6,190,350). In some embodiments, placement tool 120 is configured to place the proximal end of the implant about 6.4 mm (0.25 inch) to about 19.1 mm (0.75 inch) from the site of the incision. In some embodiments, placement tool 120 is configured to place the proximal end of the implant about 12.7 mm (0.5 inch) from the site of the incision.

In some embodiments, the visualization opening 110 is provided. Visualization opening 110 provides an unobstructed opening through which skin above the advancing cannula 115 can be seen under the skin and/or palpitated to confirm proper placement of cannula 115, and thus the implant itself, to a particular/predetermined depth during dispensing of the implant.

In some embodiments, visualization opening 110 is replaced by a visualization window that provides a substantially clear or transparent (e.g., plastic) film or screen through which skin above advancing cannula 115 can be seen but not palpitated during dispensing of the implant.

Thereafter, placement guide 100 (and tool 120) are removed from the implantation site, observation (e.g., visual observation) and/or palpitation of the site can be used to confirm proper placement of the implant to a determined depth, the site can be cleaned, optionally a skin adhesive applied to at least one side of the incision, and then the ends of the incision held together for a period of time to achieve hemostasis. Steri-Strips™ and/or a bandage may thereafter applied. Generally, the incision is sufficiently narrow, being just wide enough to accommodate the cannula, that stitches are unnecessary and Steri-Strips™ will suffice.

Figure 2A:
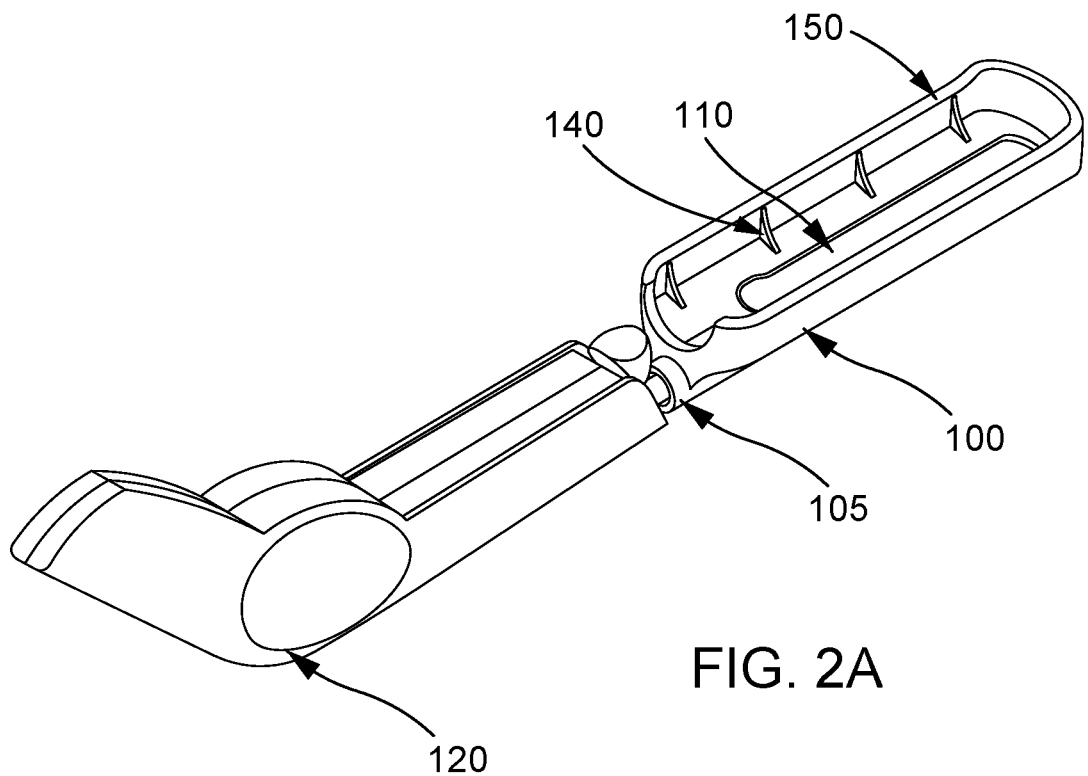
FIGS. 2A and 2B are illustrations depicting structures of an implant placement system according to some embodiments.
Figure 2B:
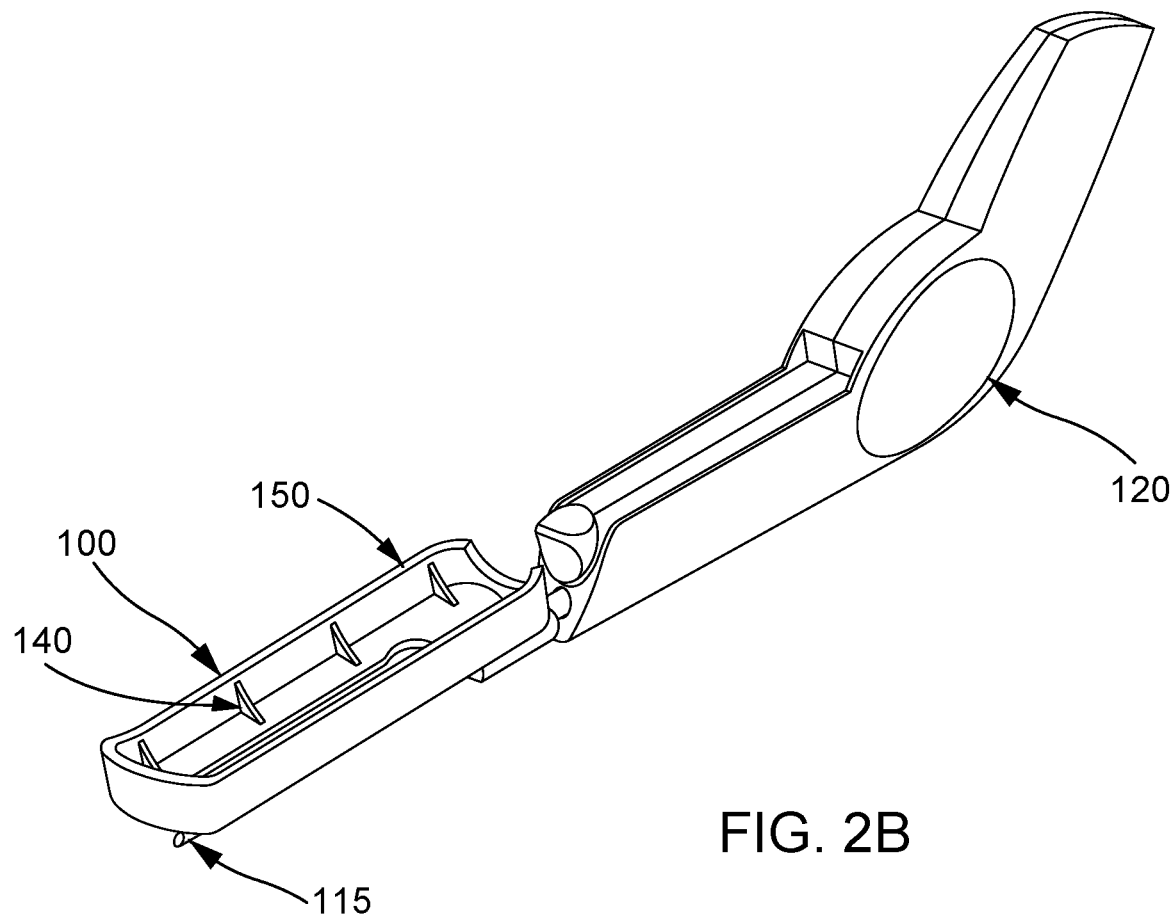

FIGS. 2A-B show exemplary configurations of the implant placement system.

Figure 3A:
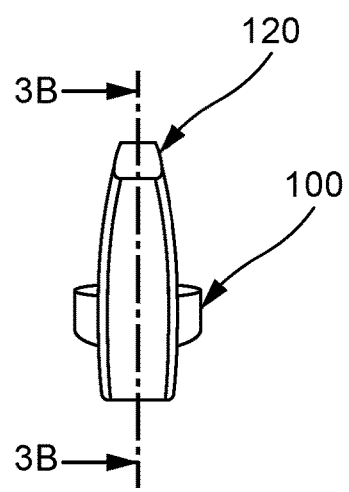
FIGS. 3A and 3B are illustrations depicting structures in section views of an implant placement system according to some embodiments.
Figure 3B:
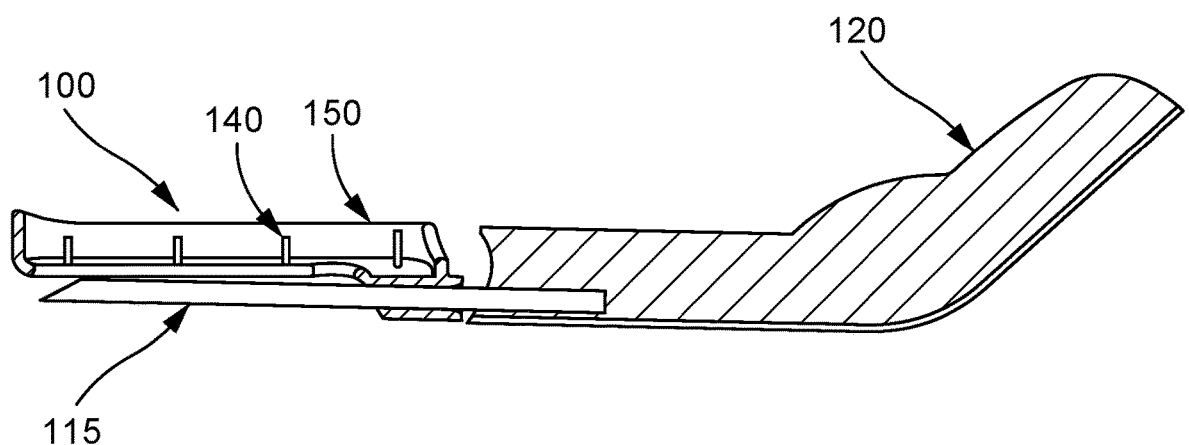

FIG. 3 shows an exemplary section view of placement cannula 115 inserted through pilot-tube (not shown) 105 into placement guide 100. Placement cannula 115 is connected to the handle of placement tool 120 and extends through pilot-tube 105 such that placement cannula 115 is primarily disposed under visualization opening 110 of placement guide 100.

Figure 4A:
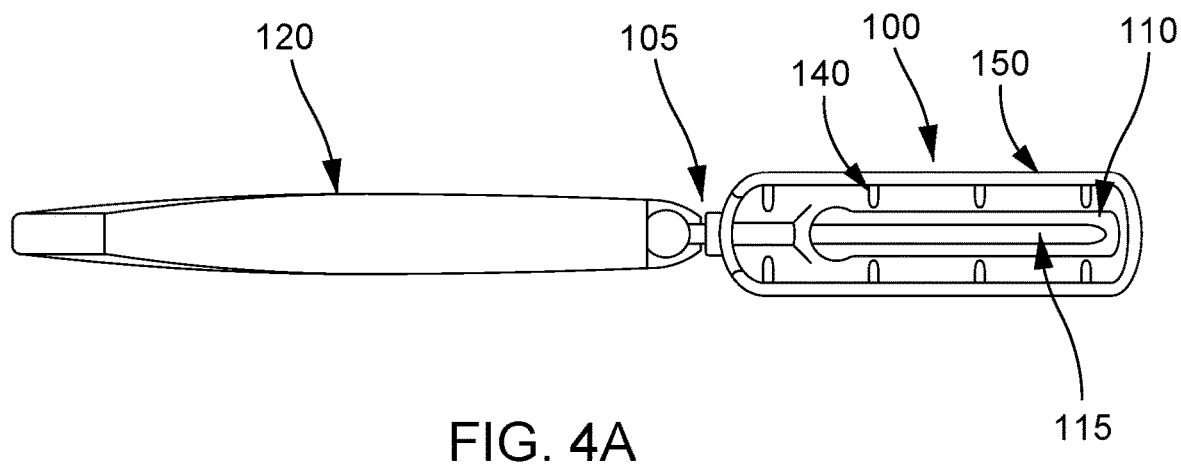
FIGS. 4A, 4B and 4C are illustrations depicting various views of structures of an implant placement system according to some embodiments.
Figure 4B:
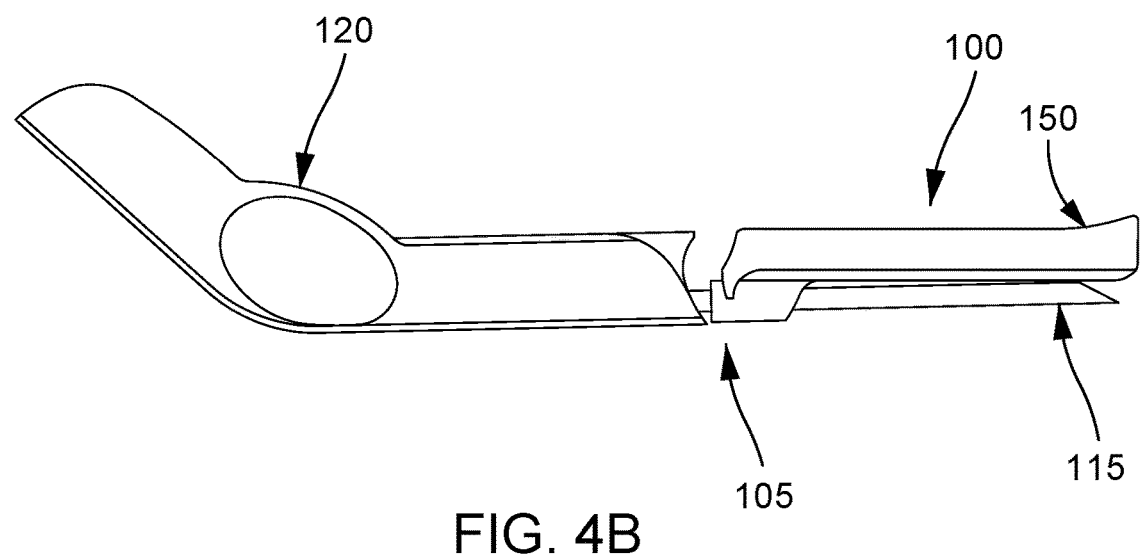
Figure 4C:
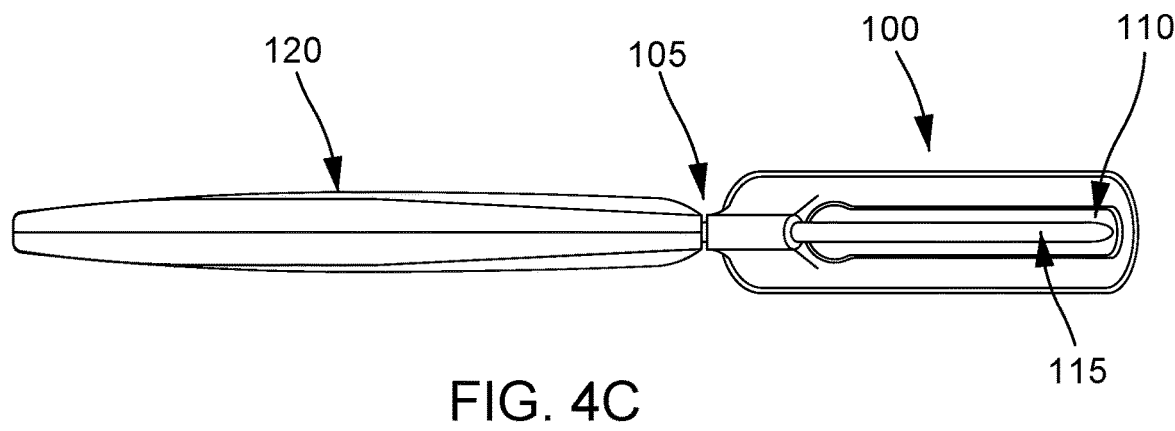

FIGS. 4A-C show various views (top, side, bottom, respectively) of a system prior to dispensing of an implant from cannula 115.

FIGS. 5A-E show placement guide 100 of an implant placement system according to some embodiments.

FIG. 5A shows a top view of an embodiment of placement guide 100 illustrating portions of pilot-tube 105 and visualization opening 110. In some embodiments, visualization opening 110 is a cut out from within placement guide 100, while in others, opening 110 is replaced by a visualization window that may be a substantially clear window made from transparent material. Also shown are one or more gussets 140 (i.e., reinforcing ribs, for example, four on each side are shown) and raised sides 150 for increasing the rigidity of placement guide 100. Gussets 140 are generally oriented in a perpendicular direction relative to the length of pilot-tube 105 and/or the length of visualization opening 110.

FIG. 5B shows a side view of an embodiment of placement guide 100 illustrating the first surface which is placed adjacent the skin during use, and pilot-tube 105 extending beneath the first surface.

FIG. 5C shows a bottom view of an embodiment of placement guide 100 illustrating pilot-tube 105 and visualization opening 110.

FIG. 5D shows a back view of an embodiment of placement guide 100, illustrating an exemplary profile of the back edge of placement guide 100 with proximal opening of pilot-tube 105.

FIG. 5E shows a section view of an embodiment of placement guide 100, illustrating Spacing A of the proximal and distal ends of pilot-tube 105, Distance B, i.e., the inner diameter of pilot-tube 105, and Angle C of the longitudinal axis of pilot-tube 105 at least to the first surface, i.e., of the underside of placement guide 100.

In some embodiments, pilot-tube angles may be measured or verified using either a coordinate measuring machine (CMM) or by inserting a steel rod through the pilot-tube and measuring the distance from the top of the rod to two or more points on the underside of the guide. With two or more of such measured distances, pilot-tube angles can be derived. Exemplary distances for the illustrated placement guide of FIGS. 5A-E, having a length of 86 mm, include 0.35 mm±0.5 mm at a point on the underside of the guide that was 76.0 mm from the proximal end of the pilot-tube, and 1.28 mm±0.2 mm at a point on the underside of the guide that was 30.0 mm from the proximal end of the pilot-tube.

Regarding FIGS. 5A-E, exemplary materials/specifications that can be used in the manufacture of guide 100 include clear plastic (PC; Dow Calibre 2081-15). A-side and B-side finishes: SPI B-2. Part volume: 7.6 cm$^3$. General corner radius: 0.1 mm. Upon manufacture of the guide, parts are generally clean and free from burrs, sharp edges, machine oil and debris. Surfaces generally do not have visible indications of foreign matter, fingerprints, abrasions, corrosion, scratches, voids, dents, inclusions, knit lines, or discoloration. Flash and ejector vestiges (maximum 0.25 mm) generally lack sharp edges.

As shown in FIGS. 6-9, in some embodiments, an implant removal tool 200 is provided which is configured to remove an implant from tissue beneath the outer surface of skin of a patient (which may have been implanted into the patient using placement tool 120 and placement guide 100 as described above). In some embodiments, implant removal tool 200 includes two opposing arms 205/215 connected by a connecting structure 235, and such structure 235 may be flexible to provide spring-like functionality between opposed arms 205/215. Each arm 205/215 may include thereon an open end 210/220, or optionally, open ends 210/220 may each be provided at the end of a wire which spans along each of arms 205/215 from one to the other via connecting structure 235 ("wire form features" 210/220 are also referred to herein as "ends," "open ends" or "distal ends"). Wire form features 210/220 need not be wire; they may alternatively be made from stiff plastic wiring, tubing or the like. In some embodiments, implant removal tool 200 is substantially made from a single wire.

The connecting structure 235 and/or arm structures 205/215 may be configured with a handle like structure 225 to allow ease of use of device 200. In some embodiments, the connecting structure 235 and/or arm structures 205/215 may be configured without a handle like structure 225. For example, the sides of handle 225 that extend along the first opposing arm 205 and the second opposing arm 215 may be ergonomically shaped to a configuration that allows a user to more comfortably grip handle 225. In some embodiments, handle 225 may be a separate item being connected to opposing arms 205/215 at several discrete locations along the length of arms 205/215, while in other embodiments, handle 225 may be connected to opposing arms 205/215 along the entire length of arms 205/215. In some embodiments, handle 225 may parallel connecting structure 235 without being attached to connecting structure 235, or handle 225 may be connected to connecting structure 235 at one or more discrete locations along connecting structure 235. In some embodiments, connecting 235 and/or arm structures 205/215 may be configured from metal wire or relatively rigid plastic tubing, without having additional handles 225.

Figure 6:
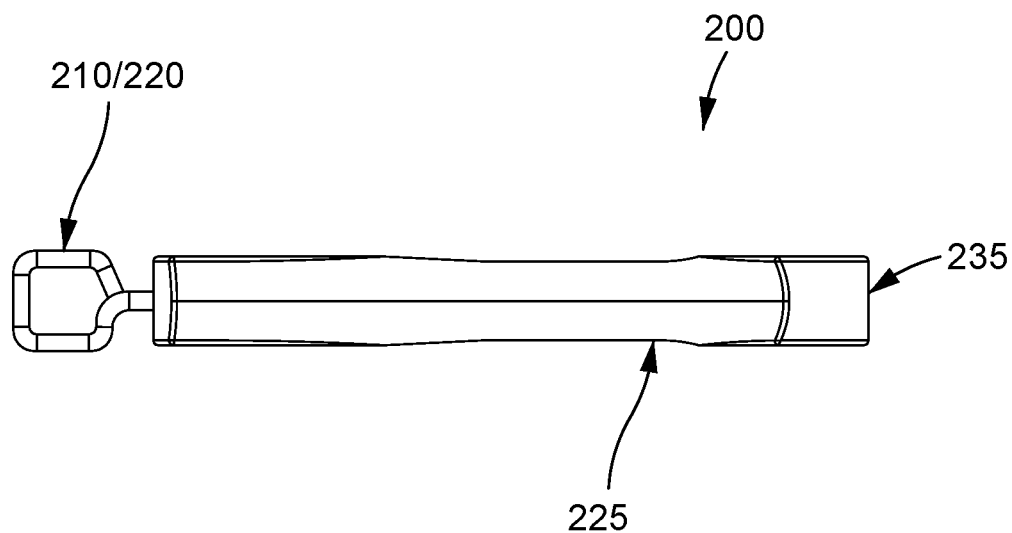
FIG. 6 is an illustration depicting structures of an implant removal tool shown in a side view according to some embodiments.

FIG. 6 shows a side view of an embodiment of an implant removal tool 200. The wire form feature 210/220, which in some embodiments is made from stainless steel wire, is shown, as well as a side view of handle 225 that surrounds one of the opposing arms 205/215. The portion of the handle 225 covering connector 235 between the first and second arms 205/215 can also be seen.

Figure 7:
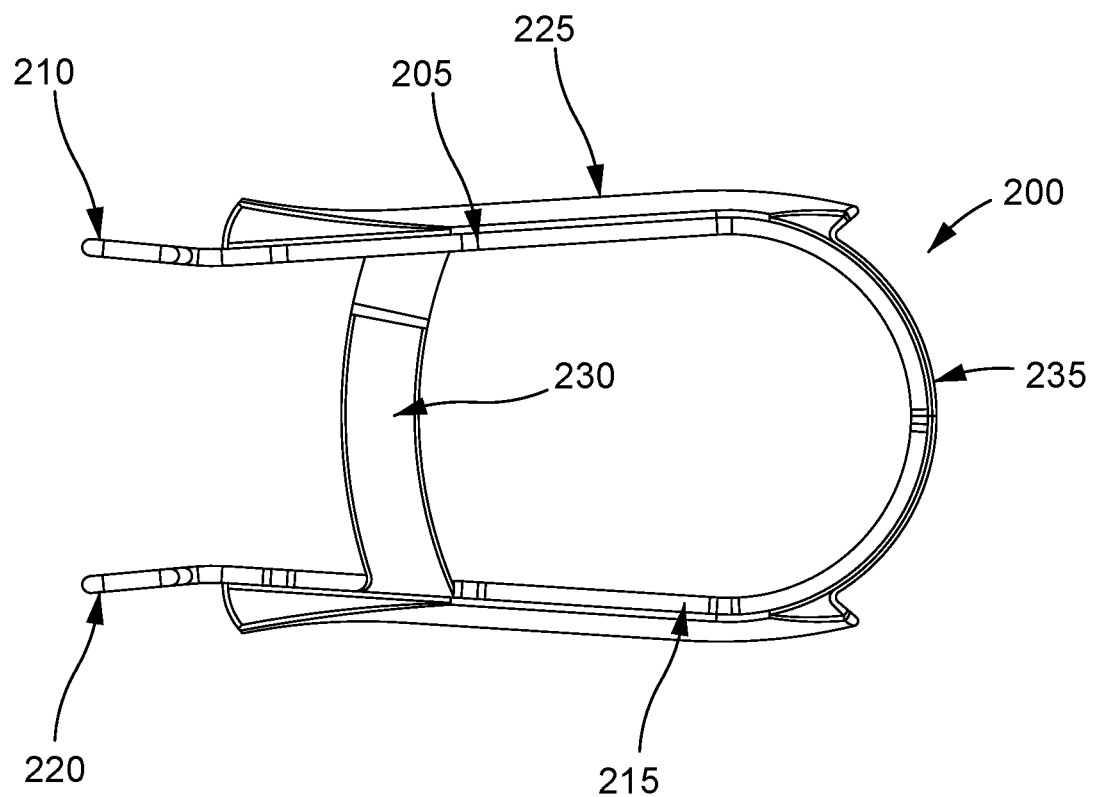
FIG. 7 is an illustration depicting structures of an implant removal tool shown in a front view according to some embodiments.

FIG. 7 shows a top view of an embodiment of implant removal tool 200. The opposing wire form features 210/220 ("ends") are shown. The ends 210/220 are each connected to one of opposing arms 205/215, which may be connected using connector 235. In some embodiments, the wire that forms the ends 210/220 also forms, or is an extension from opposing arms 205/215 and connector 235. In some embodiments, ends 210/220, opposing arms 205/215 and connector 235 are made from a single length of wire. The handle 225 may be disposed around the first arm 205 and the second arm 215. In some embodiments, the handle 225 may also run along connector 235. In some embodiments, handle 225 may be ergonomically shaped so as to fit a user's grip when squeezing handle 225 to move opposing arms 205/215 closer together. The opposing arms 205/215 and/or opposing sides of handle 225 are connected using a locking device 230. In some embodiments, the locking device 230 may extend across the middle, such as between opposing arms 205/215. The locking device 230 may provide stability and rigidity to the structure. The locking device 230 may include a sliding frictional locking mechanism or a ratchet mechanism. In some embodiments, sliding frictional locking mechanism or a ratchet mechanism of locking device 230 may be activated by the user when the user wants the locking mechanism to engage. In some embodiments, locking mechanism may automatically engage as handles 225 are squeezed together, regardless of input from the user.

Figure 8:
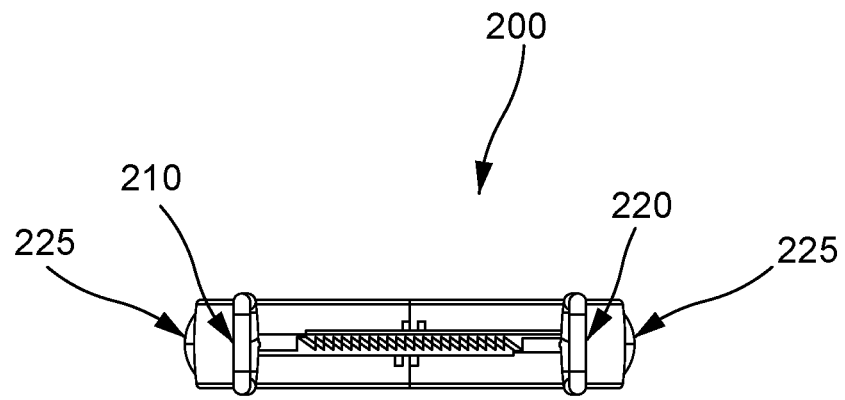
FIG. 8 is an illustration depicting structures of an implant removal tool shown in a top view according to some embodiments.

FIG. 8 shows a front view of an embodiment of implant removal tool 200. An exemplary bottom profile of opposing handles 225 and wire form features 210/220 can be seen on either side of the figure. The locking device 230 is disposed between the two sides. In some embodiments, locking device 230 may include a ratchet mechanism. The ratchet mechanism of locking device 230 may be comprised of two pieces that have a plurality of one or more opposing teeth, such that one or more teeth on each side engage with one or more teeth on the opposing side, thereby preventing opposing arms 205/215 from pulling apart or separating beyond a certain point once locking device 230 is engaged.

Figure 9:
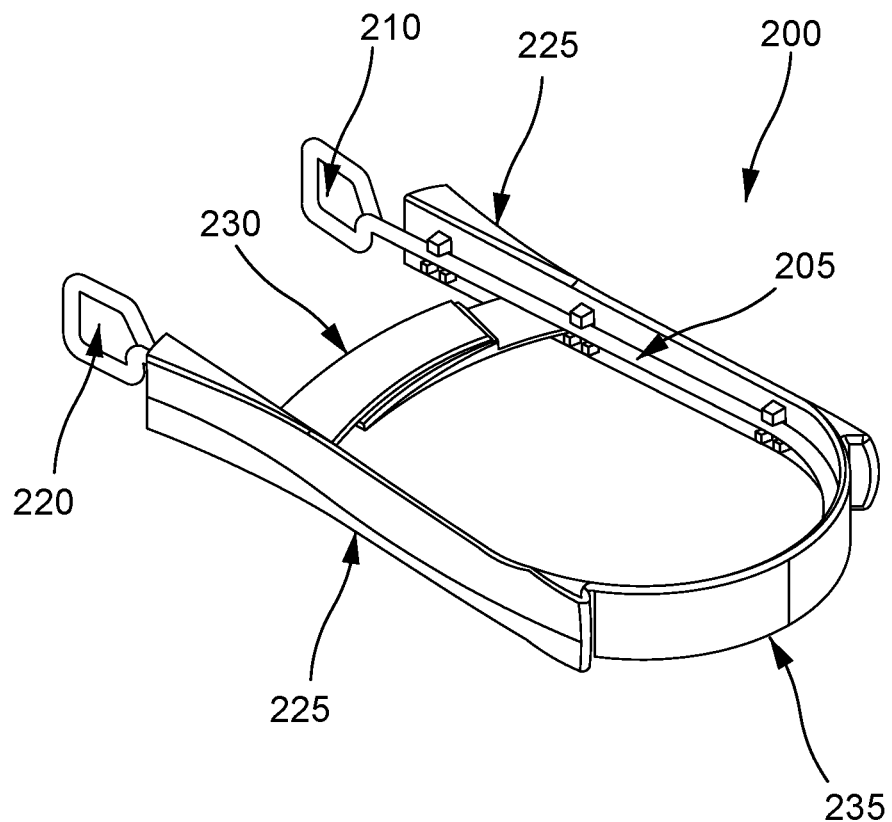
FIG. 9 is an illustration depicting structures of an implant removal tool shown in an alternate view according to some embodiments.

FIG. 9 shows an embodiment of implant removal tool 200. Wire form features 210/220 are shown at each end of the opposing arms 205/215, and handle 225 is attached to opposing arms 205/215. In some embodiments of the implant removal tool 200, handles 225 are omitted from substantially bare (e.g., wire) opposing arms 205/215. The arms 205/215 may be connected along the bottom curved edge (e.g., potentially also made from wire). For example, the opposing arms 205/215 and connector 235 may be made from a single wire. The locking device 230, which may include, for example, a ratchet mechanism (as shown) or a sliding frictional locking mechanism (e.g., 330 in FIGS. 10B-E), is disposed between two arms 205/215. When a user squeezes opposing arms 205/215 and/or handles 225, opposing arms 205/215 are pushed closer together. The locking device 230 will hold opposing arms 205/215 at a particular distance from one another, such that arms 205/215 cannot readily separate once the user has squeezed arms 205/215 into a particular position.

FIGS. 10A, 10B and 10C illustrate, in another embodiment, an implant removal tool 300, where the material (e.g., wire) that forms the ends 310/320 also forms, or is an extension from opposing arms 325 and connector 335. Opposing arms 325 can be identical or non-identical. In preferred embodiments, opposing arms 325 are configured to be gripped by a user, e.g., in the absence of additional handles (although some embodiments may also include handles). In some embodiments, wire form features 310/320 and opposing arms 325, connected by connecting structure 335, are all made from metal wire, such as stainless steel metal wire, and potentially a single length of wire. Wire form features 310/320 are shown at each end of opposing arms 325 connected by connecting structure 335. The wire form features 310/320 may be substantially circular, as shown, or may be substantially polygonal, including polygons with curved sides. In some embodiments, connecting structure 335 is a coil or spring that provides tension. In some embodiments, arms 325, wire form features 310/320 and connecting structure 335 (e.g., configured into a coil or spring) are made from a single length of wire or the like. In some embodiments, arms 325, wire form features 310/320 and connecting structure 335 (e.g., configured into a coil or spring) are made from two or more lengths of wire or the like. In some embodiments, such as that shown in FIGS. 10A-C, locking device 330 is readily removable from removal tool 300. The locking device may include sliding frictional locking mechanism disposed between the two arms 325 in an open orientation, as shown in FIG. 10B. When a user squeezes opposing arms 325, sliding frictional locking mechanism and locking device 330 may be slid along opposing arms 325, towards wire form features 310/320, to hold opposing arms 325 at a closer distance from one another as shown in FIG. 10C, relative to the distance shown in FIG. 10B, such that arms 325 cannot readily separate further once the user squeezes arms 325 into a particular position. In some embodiments, locking device 330 may be slid by the practitioner as the practitioner squeezes the opposing arms 325 together and/or locking device 330 may slide down the opposing arms 325 as the practitioner squeezes opposing arms together.

Figure 10D:
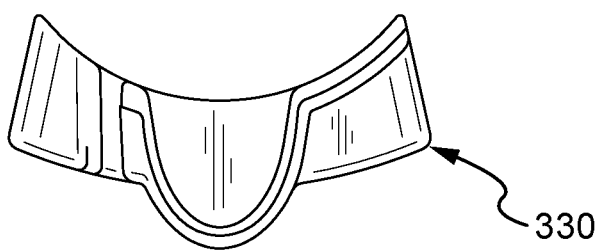
FIG. 10D is an illustration of a side view of a sliding frictional locking mechanism according to some embodiments.
Figure 10E:
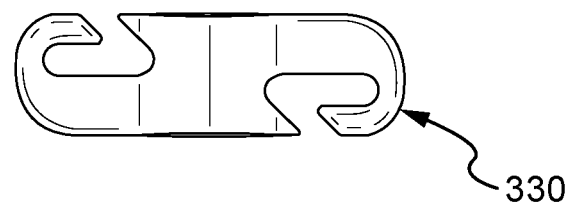
FIG. 10E is an illustration of a top view of a sliding frictional locking mechanism according to some embodiments.

FIGS. 10D and 10E illustrate, side and top views of a locking device 330 having a sliding frictional locking mechanism. In some embodiments, locking device 330 is made from, or comprises, one or more slip-resistant materials that prevent or minimize slipping of the locking device along arms 325. Exemplary slip-resistant materials include rubber, silicone, or the like. In some embodiments, locking device 330 comprises a complete or partial slip-resistant coating of rubber, silicone, or the like. In some embodiments, locking device 330 comprises a slip-resistant insert of rubber, silicone, or the like. In some embodiments, locking device 330 may have a directional coating or a directional pattern (and/or the like) that allows the locking device 330 to easily slide in one direction (for example, may easily slide towards the closer position, as the locking device moves from the position shown in FIG. 10B towards the position of FIG. 10C), but provides more friction in the opposite direction (moving from the position shown in FIG. 10C towards the position of FIG. 10B).

In some embodiments, wire form features 210/220 or 310/320 may be approximately round, however, such features may be approximately oval, square, polygonal polygonal with curved sides, or any shape which is aids the removability functionality. In some embodiments, wire form features 210/220 or 310/320 are substantially wider than the width of the implant. This may help to prevent pinching of the skin around the tented implant during removal. In some embodiments, wire form features 210/220 or 310/320 are from about 2 to about 100 times wider than the width of the implant. In some embodiments, wire form features 210/220 are from about 2 to about 50, about 5 to about 20, about 5 to about 10, times wider than the width of the implant. Implant removal tool 200 or 300 can be readily adapted for the removal of any appropriately shaped implant, capable of tenting under skin, including any substantially cylindrical or columnar shaped implant.

In some embodiments, first and second arms 205/215 or 325 may be configured to be approximately the same width as the length of the implant being retrieved, or may be configured to allow for a wider stance than the length of the implant being retrieved, such as having a stance only slightly wider than the length of the implant (for example).

In some embodiments, a method for removing an implant is provided and may include providing a removal tool as described herein. In some embodiments, the method further comprises at least one of: arranging the first arm of the removal tool at a first end of an implant and corralling or otherwise capturing the first end of the implant, and nearby skin, within the first opening or wire form feature 210/220 or 310/320, and arranging the second arm of the removal tool at the second end of the implant in a patient and corralling or otherwise capturing the second end of the implant, and nearby skin, with the second opening or other wire form feature 210/220 or 310/320. In some embodiments, the first and second arms of the removal tool may be arranged at the first and second ends of the implant simultaneously, or it may be done sequentially. In some embodiments, simultaneous placement may be preferred.

Once the wire form features 210/220 or 310/320 are aligned with the ends of the implant, a user may squeeze the two opposing arms 205/215 or 325 together. As the two opposing arms 205/215 or 325 are squeezed together, one/first wire form feature 210 or 310 and the other/second wire form feature 220 or 320 move closer together. In some embodiments, the first wire form feature 210 or 310 and the second wire form feature 220 or 320 are configured to perform the same function(s), and the first and second wire form features 210/220 or 310/320 may be identically configured or substantially identically configured.

When the first and second wire form features 210/220 or 310/320 are squeezed together to a first position, at least one end of the implant may create a tent(s) in the skin of the patient at or around the end(s) of the implant. In some embodiments, when the first and second wire form features 210/220 or 310/320 are squeezed together to a first position, the implant may create tents in the skin of the patient at or around the ends of the implant. Locking and/or ratcheting device 230 or 330 may be engaged to permit the user/ practitioner to carry out subsequent steps (e.g., incision and removal of the implant from the incision) hands-free with respect to the removal tool. Thus, once the removal tool 200 or 300 is in its locked position (the first position), the removal tool holds its position and the practitioner need not hold it.

An incision is made in or near the tent in the skin of the patient near one end of the implant. Once the incision has been made, the end of the implant near the incision may project out of the skin where it can be grabbed by forceps and/or the like. In some embodiments, the arm of the removal tool at the end of the implant opposite where the incision was made causes at least the end of the implant to be pushed out of the incision when the first and second wire form features 210/220 or 310/320 are in the first position. In some embodiments, force may be applied via the wire form feature 210/220 or 310/320 at the end of the implant opposite the incision, and the force may help drive the implant out of the incision. In some embodiments, the force may be applied by further squeezing the first and second arms 205/215 or 325 together towards a second position, which causes at least the end of the implant to be pushed out of the incision. See FIG. 13.

As noted, locking and/or ratcheting device 230 or 330 may be included with removal tool 200 or 300 to retain the distance between arms 205/215 as they are squeezed together. In some embodiments, the locking and/or ratcheting device 230 or 330 retains the distance between arms 205/215 or 325 in the first position and the second position. In this way, the practitioner need not hold the removal tool 200 or 300 in either the first position or the second position. It should also be noted that the removal tool 200 or 300 may also hold intermediate positions, such as any position between the configuration shown in FIG. 10B, the first position, the second position, and the position shown in FIG. 10C.

In some embodiments, locking device 330 may comprise a sliding frictional locking mechanism (alternatively described herein as a "sliding locking mechanism" or "frictional locking mechanism") that engages, hooks, loops or wraps around opposing arms 325 at points relatively close to connecting structure 335 when removal tool 300 is in an open orientation. In some embodiments, the sliding frictional locking mechanism 330 is engaged by a user, as opposing arms 325 are being squeezed together, by sliding locking mechanism 330 along opposing arms 325, towards wire form features 310/320. Upon release of opposing arms 325 by a user, tension (e.g., spring-like or coil-like tension) from connecting structure 335 pushes opposing arms 325 against the sliding frictional locking mechanism 330. In some embodiments, locking device 330 is made from, or comprises, one or more slip-resistant materials, e.g., rubber, silicone, or the like, that prevent or minimize slipping of the locking device along arms 325. Locking device 330 thus holds opposing arms 325 at a particular distance from one another, such that the arms 325 cannot readily separate. Tension from connecting structure 335, and friction between locking mechanism 330 against opposing arms 325, prevent the sliding frictional locking mechanism 330 from unintended sliding along opposing arms 325 during the tenting procedure. In some embodiments, the practitioner slides the frictional locking mechanism 330 as the practitioner squeezes the arms 325 together, and in some embodiments, the frictional locking mechanism 330 slides down the arms 325 as the practitioner squeezes the arms 325 together (i.e., without the practitioner sliding the locking mechanism 330).

FIG. 11A illustrates, in one embodiment, placement of an implant beneath a surface of skin of a patient, where placement tool cannula 115, having indicator band 170 has been inserted into an insertion point 160 on the surface of skin 155 while placement guide 100 remains substantially stationary on an outer surface of skin 155 of the patient. During an insertion procedure, the handle of placement tool 120 and, thus, placement tool cannula 115 can be rotated by the practitioner, in clockwise and counterclockwise directions, e.g., within a span or range between about 9 o'clock to about 3 o'clock, between about 10 o'clock and about 2 o'clock, or about 11 o'clock to about 1 o'clock, relative to the central longitudinal axis of the pilot-tube on placement guide 100. In some embodiments, the rotation may be between about 10 o'clock to about 2 o'clock. Rotation of the handle portion of placement tool 120 and of the placement tool cannula 115, while placement guide 100 remains substantially stationary on the outer surface of skin 155, provides controlled placement of an implant at a determined depth, such as about 0.5 mm to about 4.5 mm, about 1 mm to about 4 mm (e.g., and in some embodiments, about 1.5 mm to about 3 mm) beneath the surface of skin 155 of the patient. As placement tool cannula 115 is being inserted into tissue in the direction shown (illustrated by the single arrow, from right to left, in FIG. 11A), counter traction may be applied with the practitioner's fingers directly to the outer surface of skin 155. (Counter traction is illustrated by the four smaller arrows, from left to right, in FIG. 11A.)

FIG. 11B further illustrates, in one embodiment, placement of an implant beneath a surface of skin 155 of a patient, until an indicator band 170 on placement tool cannula 115, reaches or approaches insertion point 160 on the surface of skin 155 of the patient. When the indicator band 170 reaches the point of insertion 160 on the surface of skin 155 of the patient, the user/practitioner can see/confirm that the cannula is fully inserted into the tissue and the implant can be dispensed from the cannula.

FIGS. 12A, 12B and 13 show some embodiments of a method for implant removal. FIG. 12A illustrates, in one embodiment, an initial stage in the method for removing an implant, where "tenting" is initiated at both ends of an implant and the nearby skin with implant removal tool 300. Opposing wire form ends 310/320 are each corralled around skin 350 at either end of an implant (shown in broken lines beneath skin 350), causing the implant and nearby skin 350 to form a raised section of skin 360. In some embodiments, connecting structure 335 is a coil that provides tension to counteract force applied by a user upon squeezing together arms 325. In some embodiments, locking device 330 comprises a sliding frictional locking mechanism such as that exemplified. As shown in FIG. 12A, arms 325 are in a relatively open orientation/position and locking device 330 is not fully "engaged;" rather locking device 330 is positioned, on arms 325, relatively close to connecting structure 335 and far from ends 310/320.

FIG. 12B illustrates, in one embodiment, a side view of tents formed around each end of implant 370, beneath a raised section of skin 360, where each end of implant 370, and nearby skin, are corralled by tool ends 310 and 320. A practitioner may make an incision in the corralled skin at either tented end of implant 370.

FIG. 13 illustrates, in one embodiment, a subsequent stage in the method for removing an implant, where the implant is emerging from an incision that was made via scalpel 380 near one tented end in the skin 350 that is corralled by tool end 310. In some embodiments, the incision can be performed "hands-free" with respect to the implant removal tool 300. That is, the tented configuration of the implant is maintained without the removal tool being held or further operated by the user/practitioner during incision and removal steps. As shown in FIG. 13, arms 325 are a closed orientation/position (e.g., the second position), locking device 330 is "engaged," and the implant has begun to emerge from the incision. Locking device 330 is positioned, on arms 325, farther from connecting structure 335 and closer to ends 310/320, than the position of locking device 330 shown in FIG. 12A.

FIG. 14 illustrates, in another embodiment, placement guide 500 illustrating portions of a pilot-tube 505 and a visualization opening 510. Also shown are gussets 540 and raised sides 550 for increasing rigidity of placement guide 500. Gussets 540 are generally oriented in a perpendicular direction, some gussets, near the pilot tube opening 505, span the full width of guide 500, and others span a partial width of guide 500, oriented in a perpendicular direction relative to the central longitudinal axis of the pilot-tube and relative to the length of visualization opening 510. Also shown is an incision opening 590 through which an incision can be made in the patient's skin for insertion of cannula 115. In some embodiments, an adhesive liner 595 is affixed to the underside of placement guide 500; the adhesive liner 595 has adhesive layers on both sides of the liner in order to adhere both to the underside of placement guide 500 and to outer surface of the patient's skin. In some embodiments, the adhesive liner provides counter traction to the skin of the patient upon insertion of the cannula 115 into an incision.

FIG. 15 illustrates, in another embodiment, an implant removal tool 400, where wire form features 410/420 and opposing arms 425, all made from metal wire, such as stainless steel metal wire. Wire form features 410/420 are shown at each end of opposing arms 425 connected by connecting structure 435. In some embodiments, connecting structure 435 is a coil or spring that provides tension. In some embodiments, arms 425, wire form features 410/420 and connecting structure 435 (e.g., configured into a "substantially symmetrical," e.g., circular, coil or spring) are made from a single length, or two or more lengths, of wire or the like.

EXAMPLES

1. Placement Guides: Rigid Vs. Flexible Construction

Implantation depths were compared using Placement Tools with two different Placement Guides, A (rigid) and B (flexible). Specifically, osmotic pumps (approximately 4 mm in diameter×44 mm long) were implanted into a live porcine model using representative Placement Tools and the two different Placement Guides A and B. Placement Guide A, the substantially rigid guide, resembled the guide illustrated in FIG. 5A-E. Placement Guide B (not shown), was a relatively flexible guide. Placement Guide A was made from rigid molded plastic that was nearly twice as thick as the more flexible plastic of Placement Guide B. Placement Guide A was sufficiently rigid that it could not be substantially flexed, warped or bent, length-wise or width-wise, by the practitioner, during the insertion procedure. By contrast, Placement Guide B could readily be flexed and bent, length-wise and width-wise, by the practitioner during the insertion procedure. Placement Guides A and B were approximately the same length (about 86 mm), but Placement Guide B was approximately half as wide as Placement Guide A (about 25 mm wide), and had raised sides that were approximately half as tall as those of Placement Guide A. Placement Guide B lacked the visualization opening and gussets that were present in Placement Guide A.

Use of Placement Guide A consistently resulted in placement of osmotic pumps at depths of about 3 mm or less below the outer surface of skin. Specifically, the depth of each end (i.e., proximal and distal) of the implanted implant was recorded and mean depths were calculated. See, e.g., Table 1 below.

By contrast, use of Placement Guide B resulted in erratic placement of osmotic pumps at various depths below the outer surface of skin, many of which appeared too deep upon visual inspection and upon palpitation. Consequently, guides having a relatively rigid design, such as those resembling Placement Guide A, may be preferred.

2. Placement Guides: Direct Vs. Indirect Counter-Traction

Implantation depths using Placement Tools with two different Placement Guides, A (narrow, about 25 mm) and C (about twice as wide) were compared. Specifically, osmotic pumps (approximately 4 mm in diameter×44 mm long) were implanted into a live porcine model using representative Placement Tools and the two different Placement Guides A and C. Placement Guide A, a relatively narrow guide, resembled the guide illustrated in FIGS. 5A-E. Placement Guide C, a relatively wide guide, resembled the guide illustrated in FIG. 14. Placement Guides A and C exhibited substantially similar rigidity. Both were significantly more rigid than Placement Guide B of Example 1.

A Placement Tool, configured with relatively narrow Placement Guide A, was used to implant osmotic pumps into the live porcine model using direct counter-traction. Specifically, a practitioner grasped the handle of the Placement Tool with their dominant hand and inserted the cannula of the Placement Tool into tissue by rotating the handle of the Placement Tool and, thus, the cannula back and forth, relative to the central longitudinal axis of the pilot-tube on the placement guide. With one or more fingers/thumb from the non-dominant hand, the practitioner applied counter-traction directly to the outer surface of skin on either or both sides of the placement guide. In doing so, the practitioner created an insertion channel within tissue via the cannula, and placed the osmotic pump, while working hands-free with respect to the placement guide.

Use of placement Guide A consistently resulted in placement of osmotic pumps at depths of about 3 mm or less below the outer surface of skin. Specifically, the depth of each end (i.e., proximal and distal) of the implanted implant was recorded and mean depths were calculated. See, e.g., Table 1 below.

A second Placement Tool, configured with the relatively wide Placement Guide C, was used to implant osmotic pumps into the live porcine model using indirect counter-traction. Specifically, a practitioner grasped the handle of the Placement Tool with their dominant hand and inserted the cannula of the Placement Tool into tissue by rotating cannula back and forth, relative to the central longitudinal axis of the pilot-tube on the placement guide. With the non-dominant hand, the practitioner indirectly applied counter-traction, by pressing one or more fingers/thumb directly onto the outer edge of Placement Guide C, and thus pressing the guide itself onto the outer surface of skin over the incision.

Placement Guide C proved problematic during placement procedures because skin near the incision exhibited an "accordion effect" by which it bunched up and rolled back, in the same direction as the inserting cannula, as the practitioner tried to insert the cannula into tissue. In response to this finding, placement procedures were repeated with Placement Tools having a modified version of Placement Guide C, itself having a double-sided adhesive layer (layer 595 in FIG. 14) affixed to its underside which, in turn, affixed Placement Guide C to the outer surface of skin around the insertion site during the insertion/placement procedure. The practitioner again indirectly applied counter-traction, by pressing a finger and thumb directly onto the outer edge of modified Placement Guide C, and thus pressing the guide/adhesive layer onto the outer surface of skin over the incision.

This modified version of Placement Guide C, having an adhesive layer, likewise proved problematic because skin near the incision similarly bunched up and rolled back as the practitioner tried to insert the cannula into tissue.

Accordingly, guides that resembled Placement Guide A were further optimized and tested. These optimized guides were relatively rigid, and sufficiently narrow to allow counter-traction to be applied by a practitioner directly to the outer surface of skin on one or both sides of the incision and placement guide.

3. Measurement of Implantation Depths in a Live Porcine Model

Depth measurements were taken of forty-eight osmotic pumps (approximately 4 mm in diameter, e.g. wide, ×44 mm long) implanted into a live porcine model using representative Placement Tools and Placement Guides described herein. Placement Guides having six different dimensions were used.

The six Placement Guides had designs resembling the guide illustrated in FIGS. 5A-E. Three of the guides had a length of 81 mm; three had a length of 86 mm. The guides had slightly different pilot-tube angles, but all such angles were configured at a slight incline (i.e., greater than 0°). As such, cannula passed through each pilot-tube at a slight incline, or upward cant, relative to the level plane of the underside of the guide. Passage of the cannula at this slight incline caused the tip of the cannula to move closer to the underside of the guide as it proceeded through and past the pilot-tube and towards the distal end of the placement guide.

By contrast, placement guides having pilot-tubes that were parallel (i.e., 0°) to the underside of the guide, or having pilot-tubes angled at a decline (i.e., less than 0°) relative to the underside of the placement guide may guide the cannula more deeply, sometimes too deeply, into tissue beneath the outer surface of skin.

Proper pilot-tube angles, having slight inclines, or upward cants, were confirmed by measuring "offset dimensions" of the placement guide. Offset dimensions were measured by placing a steel rod through the pilot-tube and measuring the average distance between the top of the inserted rod to each of two points along the underside of the guide, for example at 30.0 mm and 76.0 mm from the proximal end of the pilot-tube. Placement guides with proper pilot-tube angles, having an upward cant, have a distance between the top of the inserted rod to the underside of the guide at 30.0 mm that is greater than the corresponding distance measured at 76.0 mm.

Eight different placement sites (L1-L8) on the belly of a live porcine model were used, with six placements (P1-P6) at each site, resulting in the placement of forty-eight osmotic pumps. Additionally, two additional Placement Guides and Placement Tools were selected at random by an experienced user who tried to intentionally place two osmotic pumps deeper than the determined depth (e.g., deeper than about 5 mm below the outer surface of skin). Despite attempts to place these two implants too deeply into tissue, these implants were placed at depths that appeared substantially similar upon visual inspection, and felt substantially similar upon palpitation, to the proper depths of the forty-eight implants reported in Table 1, illustrating that the disclosed placement guides effectively prevent a user/practitioner from being able to deliberately insert an osmotic pump too deep below an outer surface of skin.

After placing the forty-eight osmotic pumps, ultrasound measurements were used to measure and record the depth below the outer surface of skin at which each osmotic pump was placed. Specifically, the depth of each end (i.e., proximal and distal) was recorded and mean depths for the osmotic pumps were calculated and tabulated in Table 1 below.

TABLE 1

| Measured Placement Depths of Implants (as mean depths in mm) | | | | | | |
|---|---|---|---|---|---|---|
| | P1 | P2 | P3 | P4 | P5 | P6 |
| L1 | 1.65 | 2.15 | 1.4 | 1.6 | 2.0 | 1.45 |
| L2 | 1.7 | 2.1 | 1.9 | 1.7 | 1.7 | 2.15 |
| L3 | 1.6 | 2.1 | 1.75 | 1.75 | 1.65 | 2.1 |
| L4 | 1.8 | 3.05 | 1.25 | 1.5 | 1.9 | 1.5 |
| L5 | 1.9 | 1.7 | 1.95 | 2.15 | 2.15 | 1.95 |
| L6 | 1.95 | 1.9 | 2.55 | 1.75 | 2.05 | 1.6 |
| L7 | 1.85 | 1.55 | 1.7 | 1.4 | 1.45 | 2.15 |
| L8 | 1.6 | 1.95 | 1.6 | 2.6 | 1.95 | 1.45 |
| Average | 1.76 | 2.06 | 1.76 | 1.81 | 1.86 | 1.79 |

The average depth for all forty-eight implantations was 1.85 mm below the outer surface of skin. The average proximal depth was 1.87 mm and average distal depth was 1.84 mm. The shallowest implantation was 1.2 mm (at a proximal end, occurring once) and the deepest was 3.2 mm (at a proximal end, also occurring once). All of the inserted osmotic pumps, even the two osmotic pumps that the experienced user tried to place deeper than desired, could be easily removed.

The data of Table 1, and data from the two osmotic pumps that the experienced user tried but failed to place deeper than desired, demonstrate that all six Placement Guides, having lengths of 81 mm or 86 mm, ensured proper placement of an osmotic pump below the outer surface of skin and which could be easily removed.

4. Phase 1 Study Evaluating the Placement of an Osmotic Mini-Pump with Placebo in Healthy Adult Subjects Primary Objective To assess the ability of the clinician to correctly use the disclosed Placement System to consistently deliver placebo osmotic mini-pump "implant" (sometimes referred to herein as a "placebo osmotic mini-pump") into the subdermis of the abdominal wall of a patient at a depth that facilitated easy removal of the implant. The Placement System was used to place (i.e., insert) the osmotic mini-pump beneath the skin in the subject's abdominal wall. The Placement System included a Placement Tool and Placement Guide, both resembling those shown in FIG. 1A. The Placement Guide interfaced with the Placement Tool and was designed to control and confine the placement depth of the placebo osmotic mini-pump.

Primary Endpoint
　　Number and percentage of placebo osmotic mini-pumps that were correctly placed with the Placement System.
Secondary Objectives
　　To assess the ability to remove a placebo osmotic mini-pump placed with the Placement System.
　　To assess the tolerability of the procedure to place the placebo osmotic mini-pump using the Placement System.
　　To assess the ease of use of the Placement System based on the previous experience of the operator with an embodiment of the Placement Tool.
Secondary Endpoints
　　Number and percentage of placebo osmotic mini-pumps placed with the Placement System that were correctly removed.
　　Mean depth of placebo osmotic mini-pump placement (determined immediately after placement on Day 0 and just prior to removal at Week 2).
　　Consistency of the depth of the proximal and distal ends of the inserted placebo osmotic mini-pump as measured in mm.
　　Assessment of the tolerability of the procedure to place the placebo osmotic mini-pump using an embodiment of the Placement System.
　　Assessment of the ease of use of a Placement System described herein.
Additional Assessments
　　Time taken for placement of the inserted placebo osmotic mini-pump.
　　Time taken for removal of the inserted placebo osmotic mini-pump.
Duration of Treatment
　　Approximately 5 weeks: Screening Visit (Visit 1, Week −2 [Day −14 to Day −2]), Placement Visit (Visit 2, Day 0), Removal Visit (Visit 3, Week 2±3 days), Post-Treatment Telephone Follow-Up (Visit 4, Week 3±7 days).
Methodology
　　This was a Phase 1, open-label, single-site study in healthy, normal volunteers. A total of 20 healthy adult subjects (male and female subjects) between the ages of 18 and 60, inclusive, were enrolled. Subjects were required to participate in 3 visits, including 1 Screening Visit, 1 Placement Visit and 1 Removal Visit, followed by 1 Follow up telephone call 1 week after the Removal Session. The total duration of participation for each subject was approximately 5 weeks.
　　Subjects were interviewed at the Screening Visit to review medical history and to verify inclusion and exclusion criteria. Subjects who met screening criteria at Visit 1 (Week −2 [Day −14 to Day −2]) reported to the research facility on Visit 2 (Day 0) for the Placement Visit. Each subject had a placement (i.e., insertion) of the placebo osmotic mini-pump in the left upper abdomen quadrant of the abdominal wall using an embodiment of the Placement System. A trained and certified clinician performed the placement using proper sterile technique. A certified ultrasound technician verified the proximal and distal depths of the placed placebo osmotic mini-pump. The subject was then prepared for discharge by the clinician. Following a 2-week period to allow the incision to heal, the subject returned on Visit 3 (Week 2±3 days) for a second ultrasound reading to confirm the depth of the placebo osmotic mini-pump. Immediately thereafter on Visit 3, the placebo osmotic mini-pump was removed by the clinician.
　　Experienced Clinicians and Novice Clinicians were recruited to perform the device placement and removals. Both had had a minimum of 2 years of professional experience. Novice Clinicians had no prior experience with placement and removal procedures of the osmotic mini-pump. Experienced Clinicians had been trained and certified by Applicant and performed at least 10 placements and removal procedures of the osmotic mini-pump. The Experienced Clinician Group contained 2 clinicians. This group performed 50% of the placements and 50% of the removals of the device. The Novice Clinician Group also contained 2 clinicians. This group likewise performed 50% of the placements and 50% of the removals of the device. The same clinician performed placement and removal procedures in the same subject.
　　The ability of the Placement System to consistently deliver the placebo osmotic mini-pump at proper (e.g., <5 mm) depths that facilitated the easy removal was evaluated by ultrasound at the time of placement and at the time of removal. Ultrasound was done both upon placement and prior to removal since it was possible that the fluid from lidocaine could impair the ability to evaluate the actual depth at the time of initial placement. This fluid from lidocaine generally diminished within two weeks. The ability to remove the placebo osmotic mini-pump initially placed with the Placement System was demonstrated by having subjects return within two weeks after placement in order to have the device removed.
　　The amount of time for the clinician to perform the placement task using the Placement System was recorded, and the location of the placebo osmotic mini-pump was documented.
The Osmotic Mini-Pump of the Study
　　The osmotic mini-pump, described herein, is part of an investigational combination product consisting of exenatide in the osmotic mini-pump that is being developed for the treatment of type 2 diabetes. A placebo osmotic mini-pump was used for this study. The placebo osmotic mini-pump was placed in the abdominal wall by trained and certified medical personnel during a clinic visit using a Placement System.
　　The placebo osmotic mini-pump consisted of a cylindrical titanium alloy reservoir with external dimensions of about 4 mm in diameter (e.g., wide) by about 44 mm in length. The reservoir was capped at one end by a controlled-rate, semi-permeable membrane and capped at the other end by a diffusion moderator through which placebo was released from the drug reservoir. The placebo formulation, piston, and osmotic engine were contained inside the cylinder. The placebo osmotic mini-pump released the placebo at a predetermined rate based on the principle of osmosis. Water from the extracellular space entered the device through the semi-permeable membrane directly into the osmotic engine that expanded to drive the piston at a slow and consistent rate of travel. Movement of the piston forced the placebo to be released through the orifice of the diffusion moderator. The placebo osmotic mini pump did not contain exenatide or any biologically active drug.
Screening Procedure (Visit 1, Day −14 to −2)
　　Subjects reported to the study site for a Screening Visit within 2 to 14 days before the Placement Session. The Screening Visit consisted of obtaining the subject's consent, reviewing the subject's medical history, collection of laboratory specimens, and ensuring that the subject met the inclusion/exclusion criteria. Subjects were assigned to a clinician after eligibility was confirmed by assessments done at the Screening Visit.
Placement Session (Visit 2, Day 0±0 Days)
　　The site staff interviewed the subjects to affirm inclusion criteria restrictions were not violated since screening. Subjects underwent testing in the following order:

A clinician-administered marking and cleaning of the testing area.

Injection of lidocaine and placement of the placebo osmotic mini-pump using the Placement System.

Hemostasis was achieved by applying steady direct pressure to the incision site with sterile gauze for approximately 3 to 5 minutes.

Mastisol® Skin Adhesive was applied to either side of the incision.

The edges of the incision were opposed and closed with Steri-Strips™ and a standard bandage.

The depths of the proximal and distal ends of the placebo osmotic mini pump were verified by an ultrasound technician using an ultrasound machine and probe.

Once proximal and distal depths of the placebo osmotic mini-pump were verified the clinician prepared the subject for discharge. The subject was scheduled to return in 2 weeks for the Removal Session. The clinician was asked scripted questions regarding the clinician's impressions concerning the Placement System, and also asked to complete several questionnaires.

Removal Session (Visit 3, Week 2±3 Days)

Subjects underwent testing in the following order:

A clinician located the placed (i.e., inserted) placebo osmotic mini-pump marked it.

An ultrasound technician verified the depth of the placebo osmotic mini-pump using ultrasound.

The removal site was cleaned with ChloraPrep®, followed by the clinician immobilizing and tenting the tip of the placebo osmotic mini-pump where the incision was to be made.

Lidocaine was injected to the tented tip of the device followed by a small (nick) incision with a scalpel blade down on the device until the clinician felt the blade contacting the metal tip. The device was then removed through the incision.

Hemostasis was achieved by applying steady direct pressure to the incision site with sterile gauze for approximately 3 to 5 minutes.

Once hemostasis was achieved, the incision was closed with Steri-Strips™ and a standard bandage.

After the Removal Session, clinicians were asked questions to obtain subjective impressions regarding their experience of removing the placebo osmotic mini-pump, and they were asked to complete several questionnaires.

Results

Placement and Removal Procedure Summary

The primary endpoint was the same between Experienced and Novice Groups. Both groups properly placed all placebo osmotic mini-pumps (Table 2, n=20, 10 subjects in each group, 100%).

TABLE 2

Primary Endpoint - Number and Percentage of Correctly Placed Placebo Osmotic Mini- Pumps

| | Clinician Category | | |
|---|---|---|---|
| | Experienced Group n = 10 | Novice Group n = 10 | Overall n = 20 |
| Correctly placed placebo osmotic pump | 10 (100%) | 10 (100%) | 20 (100%) |

The secondary endpoint regarding the number and percentage of correctly removed placebo osmotic mini-pumps was similar between Experienced and Novice Groups: 9 subjects (90%) by the Experienced Group (see below) and 10 subjects (100%) by the Novice Group. Secondary endpoints of mean depth and consistency of the depth of the proximal and distal ends of the placebo osmotic mini-pump were similar between clinician groups. See Tables 3 and 4. Data regarding additional endpoints are summarized in Tables 5 and 6.

TABLE 3

Secondary Endpoints at Day 0

| | | Placebo Session (Day 0) Clinician Category | | |
|---|---|---|---|---|
| | | Experienced Group (n = 10) | Novice Group (n = 10) | Overall (n = 20) |
| Correctly removed placebo osmotic mini pump | n (%) | | | |
| Depth of the proximal end of the placebo osmotic mini pump (mm) | N | 10 | 10 | 20 |
| | Mean (Std.) | 4.3 (1.2) | 4.1 (0.4) | 4.2 (0.9) |
| | Median | 4.0 | 4.1 | 4.0 |
| | Min. | 3.2 | 3.3 | 3.2 |
| | Max | 6.9 | 4.7 | 6.9 |
| Depth of the distal end of the placebo osmotic mini pump (mm) | N | 10 | 10 | 20 |
| | Mean (Std.) | 3.7 (0.9) | 4.0 (0.9) | 3.8 (0.9) |
| | Median | 3.5 | 4.3 | 4.0 |
| | Min. | 2.5 | 2.5 | 2.5 |
| | Max | 5.4 | 5.4 | 5.4 |

TABLE 4

Secondary Endpoints at Week 2

| | | Removal Session (Week 2) Clinician Category | | |
|---|---|---|---|---|
| | | Experienced Group (n = 10) | Novice Group (n = 10) | Overall (n = 20) |
| Correctly removed placebo osmotic mini pump | n (%) | 9 (90%) | 10 (100%) | 10 (100%) |
| Depth of the proximal end of the placebo osmotic mini pump (mm) | N | 10 | 10 | 20 |
| | Mean (Std) | 3.6 (1.1) | 3.4 (0.5) | 3.5 (0.9) |
| | Median | 3.1 | 3.5 | 3.4 |
| | Min. | 2.5 | 2.4 | 2.4 |
| | Max | 5.6 | 4.0 | 5.6 |
| Change from day 0 in the depth of the proximal end of the placebo osmotic mini pump (mm) | N | 10 | 10 | 20 |
| | Mean (Std.) | −0.8 (0.5) | −0.7 (0.5) | −0.7 (0.5) |

TABLE 4-continued

Secondary Endpoints at Week 2

| | | Removal Session (Week 2) Clinician Category | | |
|---|---|---|---|---|
| | | Experienced Group (n = 10) | Novice Group (n = 10) | Overall (n = 20) |
| | Median | −0.8 | −0.7 | −0.8 |
| | Min. | −1.4 | −1.3 | −1.4 |
| | Max | 0.3 | 0.2 | 0.3 |
| Depth of the distal end of the placebo osmotic mini pump (mm) | N | 10 | 10 | 20 |
| | Mean (Std) | 2.5 (0.6) | 2.9 (0.6) | 2.7 (0.6) |
| | Median | 2.4 | 2.8 | 2.7 |
| | Min. | 1.7 | 2.1 | 1.7 |
| | Max | 3.3 | 4.2 | 4.2 |
| Change from day 0 in the depth of the distal end of the placebo osmotic mini pump (mm) | N | 10 | 10 | 20 |
| | Mean (Std.) | −1.2 (0.7) | −1.1 (0.7) | −1.1 (0.7) |
| | Median | −1.1 | −1.2 | −1.1 |
| | Min. | −2.3 | −2.1 | −2.3 |
| | Max | 0 | 0.3 | 0.3 |

TABLE 5

Additional Endpoints at Day 0

| | | Placebo Session (Day 0) Clinician Category | | |
|---|---|---|---|---|
| | | Experienced Group (n = 10) | Novice Group (n = 10) | Overall (n = 20) |
| Depth of the center of the placebo osmotic mini pump (mm) | N | 10 | 10 | 20 |
| | Mean (Std.) | 4.0 (0.7) | 4.0 (0.5) | 4.0 (0.6) |
| | Median | 3.9 | 4.0 | 4.0 |
| | Min. | 3.1 | 3.3 | 3.1 |
| | Max | 5.4 | 4.7 | 5.4 |

TABLE 6

Additional Endpoints at Week 2

| | | Removal Session (Week 2) Clinician Category | | |
|---|---|---|---|---|
| | | Experienced Group (n = 10) | Novice Group (n = 10) | Overall (n = 20) |
| Depth of center of the placebo osmotic mini pump (mm) | N | 10 | 10 | 20 |
| | Mean (Std.) | 3.0 (0.7) | 3.1 (0.5) | 3.1 (0.6) |
| | Median | 2.9 | 3.1 | 3.0 |
| | Min. | 2.1 | 2.4 | 2.1 |

TABLE 6-continued

Additional Endpoints at Week 2

| | | Removal Session (Week 2) Clinician Category | | |
|---|---|---|---|---|
| | | Experienced Group (n = 10) | Novice Group (n = 10) | Overall (n = 20) |
| | Max | 4.4 | 4.1 | 4.4 |
| Change from day 0 in the depth of the center of the placebo osmotic mini pump (mm) | N | 10 | 10 | 20 |
| | Mean (Std.) | −1.0 (0.5) | −0.9 (0.5) | −0.9 (0.5) |
| | Median | −0.9 | −1.1 | −1.0 |
| | Min. | −1.9 | −1.6 | −1.9 |
| | Max | −0.4 | 0 | 0 |
| Largest depth of the placebo osmotic mini pump (mm) from both visits | N | 10 | 10 | 20 |
| | Mean (Std.) | 5.5 (1.2) | 4.4 (0.4) | 4.5 (0.9) |
| | Median | 4.2 | 4.4 | 4.3 |
| | Min. | 3.2 | 3.8 | 3.2 |
| | Max | 6.9 | 5.4 | 6.9 |

CONCLUSIONS

There were no clinically significant laboratory or physical examination findings during the study. Placebo osmotic mini-pump placement and removal was well tolerated in subjects during the study. No unexpected safety concerns were identified.

Use of one embodiment of the Placement System described herein resulted in proper placement of the placebo osmotic mini-pump implant at determined depths of less than about 5 mm that allowed convenient and safe removal of the implant from all subjects regardless of the clinician's prior experience with the placement procedure. Certain aspects of the Placement System and implantation techniques were found to optimize placement of the implant within tissue beneath the outer surface of skin:

(i) The ability of the placement cannula to rotate freely within the pilot tube of the placement guide was found to improve the ease and accuracy of insertion of the implants. During insertion of the cannula into an incision, prior to implantation of the implant, the handle portion and cannula of the placement tool were generally rotated back and forth by the dominant hand of the practitioner, in clockwise and counterclockwise directions, e.g., back and forth within a span or range between about 10 o'clock and about 2 o'clock, relative to the central longitudinal axis of the pilot-tube on the placement guide. Rotation in this manner, while the placement guide remained substantially stationary, without rotating, on the surface of the skin of the patient, allowed nimble usage of the placement tool and guide, and promoted smooth and controlled progression of the cannula into various shapes and types of tissue in different patients, with minimal or no harm or bruising.

(ii) Relatively hands-free operation of the placement guide, with the non-dominant hand, was found to optimize the placement procedure. Proper insertions of the implants into tissue of live human subjects, whose tissue is more hydrated than the drier tissues of human cadavers and live porcine models, generally required some degree of counter-traction to prevent an "accordion effect" from occurring, by which the outer surface of skin "bunches-up" or "rolls back" on both sides of the insertion as the cannula advances into tissue. Counter-traction proved particularly troublesome for live human tissue, which is more prone to this effect than drier tissues of human cadavers and live porcine models. It was discovered that such counter-traction was best applied, by use of fingers/thumb from the non-dominant hand, directly to the outer surface of skin on one or both sides of the insertion, as close to the insertion as possible. Thus, guides that were relatively wide (e.g., greater than about 80 mm), or those that were designed to be grasped or pressed with the non-dominant hand onto the outer surface of skin of the patient, proved problematic because they did not prevent the outer surface of skin from bunching-up or rolling back on both sides of the insertion. By contrast, relatively narrow guides (e.g., about 15 mm to about 35 mm), such as that, for example, shown in FIGS. 5A-E, proved superior because they allowed the clinician to apply counter-traction, with fingers/thumb the non-dominant hand, directly to the outer surface of a patient's skin, relatively close to the insertion, on one or both sides of the relatively narrow guide.

(iii) The visualization opening on the placement guide was also found to improve the ease and accuracy of insertion of implants. Guides were preferred that had a visualization opening that was longer than the entire length of the cannula, fully extended, through the pilot-tube beneath the guide. A visualization opening of such length caused the guide to overhang the sharp tip of the fully extended cannula and thus provided some protection from the sharp tip. Further, a visualization opening of this length allowed the clinician to watch and touch the outer surface of skin immediately above the full length of the advancing cannula during insertion. Visualization and palpation, of the entire length of inserted cannula beneath the skin surface, allowed the clinician to monitor and confirm proper insertion of the cannula, and thus proper placement of the implant, during the entire course of the procedure.

Any and all references to publications or other documents, including but not limited to, patents, patent applications, articles, webpages, books, etc., presented in the present application, are herein incorporated by reference in their entirety.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements from any other disclosed methods, systems, and devices, including any and all elements corresponding to target particle separation, focusing/concentration. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure). Correspondingly, some embodiments of the present disclosure may be patentably distinct from one and/or another prior art by specifically lacking one or more elements/features. In other words, claims to certain embodiments may contain negative limitation to specifically exclude one or more elements/features resulting in embodiments which are patentably distinct from the prior art which include such features/elements.

The invention claimed is:

1. A system for placing an implant, comprising:
    a placement tool comprising
        a handle portion, and
        a placement cannula having a length, a proximal end arranged near the handle portion and a distal end opposite the proximal end, the placement cannula configured to deliver the implant within a tissue of a patient via an incision in the skin of the patient at an implantation site; and
    a placement guide comprising
        a first surface having a contact face and an opposite non-contact face, the first surface contact face configured to be disposed in contact with a surface of the skin of the patient at the implantation site, and
        a pilot-tube member projecting from the contact face of the first surface and configured to be disposed in contact with the surface of the skin of the patient at the implantation site, the pilot-tube member defining a tube therethrough, the tube comprising a proximal end configured to receive the distal end of the placement cannula, a distal end spaced apart from the proximal end of the tube at a first distance, and a longitudinal central axis arranged relative to the first surface at either or both of a second distance and an angle;
    wherein the placement guide is configured to guide the placement cannula within the tissue of the patient at the implantation site to effect implantation of the implant at a predetermined placement depth beneath an outer surface of the skin of the patient at the implantation site beneath the first surface contact face such that opposite ends of the implant are placed at equal depths, and
    wherein the placement cannula is movable relative to the placement guide, and wherein the placement cannula is movable either within or adjacent to the pilot-tube member.

2. The system of claim 1, wherein at least one of the first distance, the second distance, and the angle of the longitudinal central axis of the tube relative to the first surface of the placement guide are configured to orient the longitudinal axis in order to guide the placement cannula for the delivery of the implant at the predetermined placement depth.

3. The system of claim 1, wherein the predetermined placement depth is 0.5 mm to 4.5 mm beneath the outer surface of the skin of the patient.

4. The system of claim 1, wherein the placement guide further comprises a visualization window or opening, wherein the visualization window or opening extends along a length and a width of the placement guide and is configured to allow visual observation and/or palpation or touch of an area of an outer surface of skin around the implantation site.

5. The system of claim 1, wherein the placement guide further comprises a visualization opening, wherein the visualization opening extends along a length and a width of the placement guide and is configured to allow visual observation and palpation or touch of an area of an outer surface of skin around the implantation site.

6. The system of claim 1, wherein the implant is an osmotic pump.

7. The system of claim 1, configured to permit clockwise and counterclockwise rotation of the placement cannula within the tube and relative to the longitudinal central axis of the tube.

8. A method for placing an implant, comprising:
providing a placement system according to claim 1.

9. The method of claim 8, further comprising at least one of:
loading the implant into the distal end of the placement cannula;
creating an incision in the skin at an implantation site;
arranging the placement guide at the implantation site, such that the distal end of the tube is aligned with the incision;
inserting the distal end of the loaded placement cannula in the proximal end of the tube;
moving the placement cannula relative to the pilot-tube member until at least a part of the handle portion is proximate the proximal end of the tube such that the distal end of the placement cannula is guided farther into the incision and into the tissue beneath and/or adjacent the incision;
releasing the implant from the placement cannula;
removing the placement cannula from the skin of the patient; and
removing the placement guide from the skin of the patient.

10. The method of claim 9, wherein the placement cannula is guided into the incision and into the tissue with rotation of the handle portion, thereby resulting in rotation of the placement cannula within the pilot-tube member.

11. The method of claim 9, wherein prior to creating the incision, the method further comprises at least one of:
cleaning the skin at the implantation site;
marking the skin for making the incision; and
injecting a local anesthetic in a vicinity of the marked skin.

12. The method of claim 9, wherein after release and/or removal of the placement cannula, and/or removal of the placement guide, the method further comprises at least one of:
cleaning the incision;
applying pressure to the incision;
applying an adhesive to at least one side of the incision; and
closing the incision.

13. The method of claim 9, wherein the implant is released from the placement cannula at the predetermined depth.

14. The method of claim 13, wherein the predetermined depth is between 0.5 mm to 4.5 mm beneath the outer surface of the skin of the patient.

15. The method of claim 14, wherein opposite ends of the implant are placed at equal depths, resulting in a level placement of the implant with respect to the outer surface of the skin of the patient.

16. The method of claim 15, wherein opposite ends of the implant are placed at a predetermined depth that is within 0.3 mm of one another.

17. The system of claim 1, wherein the placement cannula is movable within and relative to the handle portion.

18. A placement guide for use with a placement tool, the placement guide comprising:
a first surface having a contact face and an opposite non-contact face, the first surface contact face configured to be disposed in contact with a surface of the skin of a patient at the implantation site; and
a pilot-tube member projecting from the contact face of the first surface and configured to be disposed in contact with the surface of the skin of the patient at the implantation site, the pilot-tube member defining a tube therethrough, the tube comprising a proximal end configured to receive a distal end of a placement cannula of the placement tool for delivering an implant to tissue, a distal end spaced apart from the proximal end of the tube at a first distance, and a longitudinal axis therethrough from the proximal end to the distal end,
wherein the longitudinal axis is arranged relative to the first surface at either or both of a second distance and an angle,
wherein at least one of the second distance or the angle of the placement guide is configured to orient the longitudinal axis in order to guide the placement cannula of the placement tool within the tissue of the patient at the implantation site to effect implantation of the implant beneath an outer surface of the skin of the patient at the implantation site beneath the first surface contact face such that opposite ends of the implant are placed at equal depths, and
wherein the pilot-tube member is configured to permit rotation of the placement cannula within the pilot-tube member.

19. The placement guide of claim 18, further comprising a visualization window or opening that extends along a length and a width of the first surface and configured to enable visual observation and/or palpation or touch of an area of the outer surface of skin around the implantation site.

20. The placement guide of claim 19, wherein the visualization window or opening has a length that extends beyond a tip of the cannula when the cannula is inserted into, and fully extended through, the tube.

21. The placement guide of claim 18, wherein the predetermined placement depth is from 0.5 mm to 4.5 mm beneath the outer surface of the skin of the patient.

22. The placement guide of claim 18, wherein the pilot-tube member is configured to receive and guide the placement cannula into tissue.

23. The placement guide of claim 18, wherein the placement guide is made from a material that is translucent or clear.

24. The placement guide of claim 18, wherein the tube is configured at an incline relative to a level underside of the placement guide.

25. The placement guide of claim 18, wherein the placement guide cannot readily be flexed or bent, length-wise or width-wise, by a user.

26. The placement guide of claim 18, configured to permit clockwise and counterclockwise rotation of the placement cannula within the tube and relative to the longitudinal central axis of the tube.

* * * * *